(12) United States Patent
Yusibov et al.

(10) Patent No.: US 8,148,608 B2
(45) Date of Patent: Apr. 3, 2012

(54) SYSTEMS AND METHODS FOR CLONAL EXPRESSION IN PLANTS

(75) Inventors: Vidadi Yusibov, Havertown, PA (US); Marina Skarjinskaia, Newark, DE (US)

(73) Assignee: Fraunhofer USA, Inc, Plymouth, MI (US)

( * ) Notice: Subject to any disclaimer, the term of this patent is extended or adjusted under 35 U.S.C. 154(b) by 236 days.

(21) Appl. No.: 11/061,980

(22) Filed: Feb. 18, 2005

(65) Prior Publication Data

US 2006/0085871 A1   Apr. 20, 2006

Related U.S. Application Data

(60) Provisional application No. 60/546,339, filed on Feb. 20, 2004.

(51) Int. Cl.
| | |
|---|---|
| C12N 15/84 | (2006.01) |
| C12N 15/83 | (2006.01) |
| C12N 15/40 | (2006.01) |
| C12N 5/04 | (2006.01) |
| C12N 5/10 | (2006.01) |
| A01H 5/00 | (2006.01) |

(52) U.S. Cl. .... 800/294; 800/288; 435/70.1; 435/91.21; 435/91.33; 435/91.51; 435/320.1; 435/419; 435/469; 435/476

(58) Field of Classification Search .................. None
See application file for complete search history.

(56) References Cited

U.S. PATENT DOCUMENTS

| | | | |
|---|---|---|---|
| 3,747,501 A | 7/1973 | Honda et al. | |
| 4,028,847 A | 6/1977 | Davis et al. | |
| 4,196,265 A | 4/1980 | Koprowski et al. | |
| 4,683,202 A | 7/1987 | Mullis | |
| 4,816,567 A | 3/1989 | Cabilly et al. | |
| 4,935,496 A | 6/1990 | Kudo et al. | |
| 4,956,282 A | 9/1990 | Goodman et al. | 435/69.51 |
| 5,175,102 A | 12/1992 | Baulcombe et al. | 435/172.3 |
| 5,223,409 A | 6/1993 | Ladner et al. | |
| 5,316,931 A | 5/1994 | Donson et al. | 435/172.3 |
| 5,403,484 A | 4/1995 | Ladner et al. | |
| 5,427,908 A | 6/1995 | Dower et al. | |
| 5,447,858 A | 9/1995 | Key et al. | |
| 5,464,763 A | 11/1995 | Schilperoort et al. | |
| 5,491,076 A | 2/1996 | Carrington et al. | |
| 5,500,360 A | 3/1996 | Ahlquist et al. | |
| 5,502,167 A | 3/1996 | Waldmann et al. | |
| 5,530,101 A | 6/1996 | Queen et al. | |
| 5,545,806 A | 8/1996 | Lonberg et al. | |
| 5,545,807 A | 8/1996 | Surani et al. | |
| 5,558,864 A | 9/1996 | Bendig et al. | |
| 5,565,332 A | 10/1996 | Hoogenboom et al. | |
| 5,565,347 A | 10/1996 | Fillatti et al. | |
| 5,569,825 A | 10/1996 | Lonberg et al. | |
| 5,580,717 A | 12/1996 | Dower et al. | |
| 5,585,089 A | 12/1996 | Queen et al. | |
| 5,589,367 A | 12/1996 | Donson et al. | |
| 5,602,242 A | 2/1997 | Ahlquist et al. | |
| 5,625,126 A | 4/1997 | Lonberg et al. | |
| 5,627,060 A | 5/1997 | Ahlquist et al. | |
| 5,633,425 A | 5/1997 | Lonberg et al. | |
| 5,639,641 A | 6/1997 | Pedersen et al. | |
| 5,654,184 A | 8/1997 | Curtiss, III et al. | 435/172.3 |
| 5,658,727 A | 8/1997 | Barbas et al. | |
| 5,661,016 A | 8/1997 | Lonberg et al. | |
| 5,667,988 A | 9/1997 | Barbas et al. | |
| 5,679,880 A | 10/1997 | Curtiss, III et al. | 800/205 |
| 5,686,079 A | 11/1997 | Curtiss, III et al. | 424/234.1 |
| 5,693,493 A | 12/1997 | Robinson et al. | |
| 5,693,761 A | 12/1997 | Queen et al. | |
| 5,693,762 A | 12/1997 | Queen et al. | |
| 5,698,417 A | 12/1997 | Robinson et al. | |
| 5,698,426 A | 12/1997 | Huse | |
| 5,702,892 A | 12/1997 | Mulligan-Kehoe | |
| 5,705,154 A | 1/1998 | Dalie et al. | |
| 5,728,300 A | 3/1998 | Kapulnik et al. | |
| 5,733,743 A | 3/1998 | Johnson et al. | |
| 5,750,078 A | 5/1998 | Shitara et al. | |

(Continued)

FOREIGN PATENT DOCUMENTS

AU        721534        4/1998

(Continued)

OTHER PUBLICATIONS

Glossary of Molecular Biology Terrms and Abbreviations, 2003-2008, http://www.mblogic.net/glossary/default.asp?txtSearch=episome&field=Term&lang=&order=abbr_asc.*
Skarjinskaia et al., Biotech. Bioeng., 2008, vol. 100, pp. 814-819.*
Shadwick and Doran, Biotech. Bioeng., 2007, vol. 96, pp. 570-583.*
Matsuda et al., Bull. Inst. Compr. Agr. Sci. Kinki Univ., 2001, vol. 9, pp. 81-88.*
Callaway, et al., "The Multifunctional Capsid Proteins of Plant RNA Viruses," *Annu. Rev. Phytopathol.* 39: 419-460, 2001.
Chandler and Robertson, "Gene Expression Regulated by Abscisic Acid and its Relation to Stress Tolerance," *Annu. Rev. Plant Physiol. Mol. Biol.*, 45: 113-141, 1994.
Conrad and Fiedler, "Compartment-specific Accumulation of Recombinant Immunoglobulins in Plant Cells: An Essential Tool for Antibody Production and Immunomodulation of Physiological Functions and Pathogen Activity," *Plant Molecular Bio.*, 38: 101-109, 1998.

(Continued)

*Primary Examiner* — David T Fox
(74) *Attorney, Agent, or Firm* — Fish & Richardson P.C.

(57) ABSTRACT

The present invention provides systems and methods for generating clonal root lines, clonal root cell lines, clonal plant cell lines, and clonal plants and for expressing gene products in such cell lines and plants. In some embodiments, a viral vector containing a polynucleotide of interest operably linked to a promoter is introduced into a plant or portion thereof to generate clonal root lines, clonal root cell lines, clonal plant cell lines, and clonal plants. According to certain inventive methods, a viral vector containing a polynucleotide of interest operably linked to a promoter is introduced into cells of a plant cell line that is maintained in culture to generate clonal plant cell lines and clonal plants. The invention provides clonal root lines, clonal root cell lines, clonal plant cell lines, and clonal plants generated using inventive methods.

32 Claims, 18 Drawing Sheets
(5 of 18 Drawing Sheet(s) Filed in Color)

U.S. PATENT DOCUMENTS

| | | | |
|---|---|---|---|
| 5,750,871 A | 5/1998 | Moloney et al. | |
| 5,759,817 A | 6/1998 | Barbas | |
| 5,766,885 A | 6/1998 | Carrington et al. | |
| 5,770,403 A | 6/1998 | Dalie et al. | |
| 5,770,429 A | 6/1998 | Lonberg et al. | |
| 5,811,653 A | 9/1998 | Turpen | |
| 5,846,795 A | 12/1998 | Ahlquist et al. | |
| 5,853,576 A | 12/1998 | Kapulnik et al. | |
| 5,855,866 A | 1/1999 | Thorpe et al. | |
| 5,866,785 A | 2/1999 | Donson et al. | |
| 5,874,087 A | 2/1999 | Lomonossoff et al. | 424/199.1 |
| 5,877,289 A | 3/1999 | Thorpe et al. | |
| 5,888,789 A | 3/1999 | Rodriguez | |
| 5,889,189 A | 3/1999 | Rodriguez | |
| 5,889,190 A | 3/1999 | Donson et al. | |
| 5,889,191 A | 3/1999 | Turpen | |
| 5,917,117 A | 6/1999 | Ensley et al. | |
| 5,922,602 A | 7/1999 | Kumagai et al. | |
| 5,939,541 A | 8/1999 | Vance et al. | |
| 5,965,132 A | 10/1999 | Thorpe et al. | |
| 5,965,794 A | 10/1999 | Turpen | |
| 5,994,628 A | 11/1999 | Rodriguez | |
| 6,004,555 A | 12/1999 | Thorpe et al. | |
| 6,015,692 A | 1/2000 | Gyuris et al. | 435/69.1 |
| 6,042,832 A | 3/2000 | Koprowski et al. | 424/192.1 |
| 6,051,239 A | 4/2000 | Simpson et al. | |
| 6,054,566 A | 4/2000 | Donson et al. | |
| 6,077,992 A | 6/2000 | Yadav | |
| 6,093,399 A | 7/2000 | Thorpe et al. | |
| 6,127,145 A | 10/2000 | Sutliff et al. | |
| 6,261,535 B1 | 7/2001 | Thorpe et al. | |
| 6,288,304 B1 | 9/2001 | Moloney et al. | |
| 6,297,357 B1 | 10/2001 | Giordano | |
| 6,331,415 B1 | 12/2001 | Cabilly et al. | |
| 6,369,296 B1 | 4/2002 | Ratcliff et al. | |
| 6,376,752 B1 | 4/2002 | Kumagai et al. | 800/295 |
| 6,395,962 B1 | 5/2002 | Vance | |
| 6,399,317 B1 | 6/2002 | Weimer | 435/7.2 |
| 6,410,317 B1 | 6/2002 | Farmer | 435/320.1 |
| 6,448,070 B1 | 9/2002 | Koprowski et al. | 435/320.1 |
| 6,500,644 B1 | 12/2002 | Borchert et al. | 435/69.1 |
| 6,531,647 B1 | 3/2003 | Baulcombe et al. | 800/278 |
| 6,596,698 B1 | 7/2003 | Giordano et al. | |
| 6,632,980 B1 * | 10/2003 | Yadav et al. | 800/278 |
| 6,635,805 B1 | 10/2003 | Baulcombe et al. | 800/285 |
| 6,660,500 B2 | 12/2003 | Turpen et al. | 435/69.7 |
| 6,740,740 B2 | 5/2004 | Garger et al. | 530/412 |
| 6,841,659 B2 | 1/2005 | Turpen et al. | 530/427 |
| 6,852,319 B2 | 2/2005 | Hein et al. | |
| 6,858,426 B1 | 2/2005 | Zhu et al. | |
| 7,012,172 B2 | 3/2006 | Yusibov | |
| 2003/0097678 A1 | 5/2003 | Kushinov et al. | |
| 2003/0135882 A1 | 7/2003 | Metzlaff et al. | |
| 2003/0211568 A1 | 11/2003 | Ashkenazi et al. | |
| 2004/0016021 A1 | 1/2004 | Turpen et al. | |
| 2004/0019930 A1 | 1/2004 | Yusibov | |
| 2004/0088757 A1 | 5/2004 | Roberts et al. | |
| 2004/0092470 A1 | 5/2004 | Leonard et al. | |
| 2004/0093643 A1 | 5/2004 | Ensley | |
| 2005/0026291 A1 | 2/2005 | Fedorkin et al. | |
| 2005/0091706 A1 | 4/2005 | Klimyuk et al. | |
| 2005/0114920 A1 | 5/2005 | Yusibov et al. | |
| 2006/0085871 A1 | 4/2006 | Yusibov et al. | |
| 2006/0265787 A1 | 11/2006 | Piruzian et al. | |
| 2006/0277634 A1 | 12/2006 | Yusibov et al. | |
| 2007/0178148 A1 | 8/2007 | Yusibov et al. | |
| 2007/0292862 A1 | 12/2007 | Baulcombe et al. | |
| 2007/0300330 A1 | 12/2007 | Marillonnet et al. | |
| 2008/0241931 A1 | 10/2008 | Fedorkin et al. | |

FOREIGN PATENT DOCUMENTS

| | | |
|---|---|---|
| EP | 0067553 | 12/1982 |
| EP | 1162267 | 12/2001 |
| WO | WO 89/08145 | 9/1989 |
| WO | WO9311161 | 6/1993 |
| WO | WO9321334 | 10/1993 |
| WO | WO 94/20135 | 9/1994 |
| WO | WO9514099 | 5/1995 |
| WO | WO9602555 | 2/1996 |
| WO | WO9612028 | 4/1996 |
| WO | WO9627673 | 9/1996 |
| WO | WO9636701 | 11/1996 |
| WO | WO 96/40229 | 12/1996 |
| WO | WO9713864 | 4/1997 |
| WO | WO9738095 | 10/1997 |
| WO | WO 98/08375 | 3/1998 |
| WO | WO9814595 | 4/1998 |
| WO | WO9845331 | 10/1998 |
| WO | WO 00/23593 | 4/2000 |
| WO | WO0020612 | 4/2000 |
| WO | WO 00/25574 | 5/2000 |
| WO | WO 00/46350 | 8/2000 |
| WO | WO 01/38512 | 5/2001 |
| WO | WO0141559 | 6/2001 |
| WO | WO02068664 | 9/2002 |
| WO | WO2004011614 | 2/2004 |
| WO | WO2004043886 | 5/2004 |
| WO | WO2004044161 | 5/2004 |
| WO | WO2004070016 | 8/2004 |
| WO | WO2005026375 | 3/2005 |
| WO | WO2005049839 | 6/2005 |
| WO | WO2005081905 | 9/2005 |
| WO | WO2007095304 | 8/2007 |
| WO | WO2007117264 | 10/2007 |
| WO | WO2007135480 | 11/2007 |
| WO | WO2007137788 | 12/2007 |

OTHER PUBLICATIONS

Dagan, T., et al., "Ratios of Radical to Conservative Amino Acid Replacement Are Affected by Mutational and Compensational Factors and May Not be Indicative of Positive Darwinian Selection.", *Mol. Biol. Evol.* 19(7): 1022-1025, 2002.

Dawson, W.O., et al., "A Tobacco Mosaic Virus-Hybrid Expresses and Loses an Added Gene.", *Virology* 172: 285-292, 1989.

Donson, et al., "Systemic Expression of a Bacterial Gene by a Tobacco Mosaic Virus-based Vector," *Proc. Natl. Acad. Sci. USA,* 88: 7204-7208, 1991.

English, et al., "Suppression of Virus Accumlation in Transgenic Plsnts Exhibiting Silencing of Nuclear Genes," *The Plant Cell,* 8: 179-188, 1996.

Flores, et al., "Green Roots: Photosynthesis and Photoautotrophy in an Underground Plant Organ," *Plant Physiol.,* 101: 363-371, 1993.

French, R., et al., "Bacterial Gene Inserted in an Engineered RNA Virus: Efficient Expression in Monocotyledonous Plant Cells.", *Science* 231: 1294-1297, 1986.

Gelvin, S.B., "*Agrobacterium*-Mediated Plant Transformation: The Biology Behind the 'Gene-Jockeying' Tool.", *Microbiology and Molecular Biology Reviews* 67(1): 16-37, 2003.

Giri, A. and Narasu, M.L., "Transgenic Hairy Roots: Recent Trends and Applications.", *Biotechnology Advances* 18: 1-22, 2000.

Goldbach and Hohn, "Plant Viruses As Gene Vectors," *Methods in Plant Biochem.,* 10: 103-120, 1997.

Hamamoto, et al., "A New Tobacco Mosaic Virus Vector and its Use for the Systemic Production of Angiotensin-I-Converting Enzyme Inhibitor in Transgenic Tobacco and Tomato," *Biotech.,* 11: 930-932, 1993.

Grantham, R., "Amino Acid Difference Formula to Help Explain Protein Evolution.", *Science* 185:862-864, 1974.

Koprowski and Yusibov, "The Green Revolution: Plants as Heterologous Expression Vectors," *Vaccine,* 19: 2735-2741, 2001.

Ma, et al., "Assembly of Monoclonal Antibodies With IgG1 and IgA Heavy Chain Domains in Transgenic Tobacco Plants," *Eur. J. Immunol.,* 24: 151-158, 1994.

Ma, et al., "Generation and Assembly of Secretory Antibodies in Plants," *Science,* 268: 716-719, 1995.

Mathew, *Plant Viruses Online,* http://images.fs.uidaho.edu/vide/, Feb. 21, 2006.

McGarvey, et al., "Expression of the Rabies Virus Glycoprotein in Transgenic Tomatoes," *Biotech.,* 13: 1484-1487, 1995.

Modelska, et al., "Immunization Against Rabies With Plant-derived Antigen," *Proc. Natl. Acad. Sci. USA,* 95: 2481-2485, 1998.

Moffat, "Exploring Transgenic Plants as a New Vaccine Source," *Science*, 268: 658-660, 1995.

Ow, "Recombinase-directed Plant Transformation for the Post-Genomic Era," *Plant Molecular Bio*. 48: 183-200, 2002.

Peres, et al., "Shoot Regeneration Capacity From Roots and Transgenic Hairy Roots of Tomato Cultivars and Wild Related Species.", *Plant Cell Tissue, and Organ Culture* 65: 37-44, 2001.

Piruzian, et al., "A Reporter System for Prokaryotic and Eukaryotic Cells Based on the Thermostable Lichenase From *Clostridium thermocellum,*" *Mol. Genet. Genomics*, 266: 778-786, 2002.

Rao and Grantham, "Functional Analysis of the Amino-Terminal Arginine-rich Motif and its Role in Encapsidation, Movement, and Pathology," *Virology*, 226: 294-305, 1996.

Rao, S.R. and Ravishankar, G.A., "Plant Cell Cultures: Chemical Factories of Secondary Metabolites.", *Biotechnol. Adv*. 20: 101-153, 2002.

Sanchez-Navarro, et al., "Engineering of *Alfalfa mosaic virus* RNA 3 Into an Expression Vector," *Arch. Virol*. 146: 923-939, 2001.

Schwechheimer, et al., "The Activities of Acidic and Glutamine-rich Transcriptional Activation Domains in Plant Cells: Design of Modular Transcription Factors for High-level Expression," *Plant Molecular Bio*. 36: 195-204, 1998.

Shanks and Morgan, "Plant 'Hairy Root' Culture," *Curr. Op. in Biotech*., 10: 151-155, 1999.

Shivprasad, et al., "Heterologous Sequences Greatly Affect Foreign Gene Expression in Tobacco Mosaic Virus-Based Vectors.", *Virology* 255(2): 312-323, 1999.

Spitsin, et al., "Expression of Alfalfa Mosaic Virus Coat Protein in Tobacco Mosaic Virus (TMV) Deficient in the Production of its Native Coat Protein Supports Long-Distance Movement of a Chimeric TMV,", *Proc. Natl. Acad. Sci. USA* 96(5): 2549-2553, 1999.

Takamatsu, et al., "Expression of Bacterial Chloramphenicol Acetyltransferase Gene in Tobacco Plants Mediated by TMV-RNA.", *EMBO J*. 6(2): 307-311, 1987.

Takamatsu, et al., "Production of Enkephalin in Tobacco Protoplasts Using Tobacco Mosaic Virus RNA Vector.", *FEBS Lett*. 269: 73-76, 1990.

Tanzer, et al., "Characterization of Post-Transcriptionally Suppressed Transgene Expression That Confers Resistance to Tobacco Etch Virus Infection in Tobacco," *The Plant Cell*, 9: 1411-1423, 1997.

Taschner, et al., "Replication of an Incomplete Alfalfa Mosaic Virus Genome in Plants Transformed With Viral Replicase Genes," *Virology*, 181: 445-450, 1991.

Thomma, B.P., et al., "Plant Defensins.", *Planta* 216: 193-202, 2002.

Timmermans, et al., "Geminiviruses and Their Uses as Extrachromosomal Replicons," *Annu. Rev. Plant Physiol. Plant Mol. Biol.*, 45: 79-112, 1994.

van Rossum, et al., "Functional Equivalence of Common and Unique Sequences in the 3' Untranslated Regions of Alfalfa Mosaic Virus RNAs 1, 2, and 3," *J. of Virology*, 71: 3811-3816, 1997.

Verch, et al., "Expression and Assembly of a Full-length Monoclonal Antibody in Plants Using a Plant Virus Vector," *J. Immunological Meth.*, 220: 69-75, 1998.

Voss, et al., "Reduced Virus Infectivity in *N. tabacum* Secreting A TMV-specific Full-size Antibody," *Molecular Breeding*, 1: 39-50, 1995.

Waterhouse, et al., "Gene Silencing as an Adaptive Defence Against Viruses," *Nature*, 411: 834-842, 2001.

Yusibov V. and Loesch-Fries, L.S., "N-Terminal Basic Amino Acids of Alfalfa Mosaic Virus Coat Protein Involved in the Initiation of Infection.", *Virology* 208: 405-407, 1995.

Yusibov V. and Loesch-Fries, L.S., "Functional Significance of Three Basic N-Terminal Amino Acids of Alfalfa Mosaic Virus Coat Protein," *Virology*, 242: 1-5, 1998.

Yusibov, V., et al., "Antigens Produced in Plants by Infection With Chimeric Plant Viruses Immunize Against Rabies Virus and HIV-1.", *Proc. Natl. Acad. Sci. USA* 94: 5784-5788, 1997.

Yusibov, V., et al., "Plant Viral Vectors Based on Tobamoviruses.", *Plant Biotechnology: New Products and Applications*, 81-94, 1999.

Yusibov, V., et al., "Expression in Plants and Immunogenicity of Plant Virus-based Experimental Rabies Vaccine,:" *Vaccine*, 20: 3155-3164, 2002.

Zhang, J., "Rates of Conservative and Radical Nonsynonymous Nucleotide Substitutions in Mammalian Nuclear Genes.", *J. Mol. Evol*. 50: 56-68, 2000.

Zuo, J. and Chua, N-H, "Chemical-Inducible Systems for Regulated Expression of Plant Genes.", *Curr. Op. in Biotechnol*. 11: 146-151, 2000.

Altschul et al., "Gapped BLAST and PSI-BLAST: a new generation of protein database search programs", *Nucleic Acids Res.*, 25:3389-3402 (1997).

Altschul et al., "Basic Local Alignment Search Tool", *J. Mol. Biol.*, 215:403-410, (1990).

An et al., "New Cloning Vehicles for Transformation of Higher Plants", *EMBO J.*, 4:277-284 (1985).

Angell et al., "Consistent Gene Silencing in Transgenic Plants Expressing a Replicating Potato Virus X RNA", *EMBO J.*, , 6(12):3675-3684 (1997).

Arakawa et al., "A Plant-Based Cholera Toxin B Subunit-Insulin Fusion Protein Protects against the Development of Autoimmune Diabetes", *Nat. Biotechnol*. 16: 934-938 (1998).

Ay et al., "Crystal Structures and Properties of De Novo Circularly Permuted 1,3-1, 4-β-glucasnases", *Proteins*, 30(2):155-167 (1998).

Barfield et al., "Gene Tranfer in Plants of *Brassica juncea* using *Agrobacterium tumefaciens*-mediated Transformation", *Pua Plant Cell Reports*, 10(6/7): 308-314 (1991).

Bates, "Genetic Transformation of Plants by Protoplast Electroporation", *Molecular Biotechnol.*, 2(2):135-145 (1994).

Baulcombe, "Fast Forward Genetics Based on Virus-induced Gene Silencing", *Curr. Op. Plant Biol.*, 2:109-113 (1999).

Beachy et al., "A Genetic Map for the Cowpea Strain of TMV", *Virology* 73: 498-507 (1976).

Bedell et al., "The E6-E7 Region of Human Papillomavirus Type 18 is Sufficient for Transformation of NIH 3T3 and Rat-1 Cells", *Journal of Virology*, 61:3635-3640 (1987).

Belanger et al., "Human Respiratory Syncytial Virus Vaccine Antigen Produced in Plants", *FASEB Journal*, 14:2323-2328 (2000).

Bendahmane et al., "Characterization of Mutant Tobacco Mosaic Virus Coat Protein that Interferes with Virus Cell-to-Cell Movement", *Proc. Natl. Acad. Sci.*, USA, 99:3645-3650 (2002).

Bhatnagar et al., "Anthrax Toxin" *Crit. Rev. Microbiol.*, 27(3): 167-200 (2001).

Boehm et al., "Bioproduction of Therapeutic Proteins in the $21^{st}$ Century and the Role of Plants and Plant Cells as Production Platforms", *Ann. N.Y. Acad. Sci.*, 1102:121-134 (2007).

Bol et al., "A Functional Equivalence of Top Component a RNA and Coat Protein in the Initiation of Infection by Alfalfa Mosaic Virus", *Virology* 1971, 46: 73-85.

Bol et al., "Alfalfa Mosaic Virus and Ilarviruses: Involvement of Coat Protein in Multiple Steps of the Replication Cycle", *Journal of General Virology*, 80: 1089-1102 (1999).

Brennan et al., "*Pseudomanas aeruginosa* Outer-Membrane Protein F Epitopes are Highly Immunogenic in Mice when Expressed on a Plant Virus", *Microbiology*, 145:211-220 (1999).

Broothaerts et al., "Gene Transfer to Plants by Diverse Species of Bacteria", *Nature*, 433(7026):629-633 (2005).

Bruening et al., "In Vitro and In Vivo Translation of the Ribonucleic Acids of a Cowpea Strain of Tobacco Mosaic Virus", *Virology*, 71: 498-517 (1976).

Buttery et al., "Designing Meningitis Vaccines", *Journal of the Royal College of Physicians of London*, 34:163-168 (2000).

Caddick et al., "An Ethanol Inducible Gene Switch for Plants used to Manipulate Carbon Metabolism", *Nature Biotechnol*, 16: 177-180 (1998).

Canizares et al., "Use of Viral Vectors for Vaccine Production in Plants", *Immunogy and. Cell Biology.*, 83:263-270 (2005).

Carrillo et al., "Protective Immune Response to Foot-and-Mouth Disease Virus with VP1 Expressed in Transgenic Plants", *Journal of Virology*, 72(2):1688-1690 (1998).

Chen et al., "Molecular Cloning and Expression of *Bacillus subtilis* bg/S Gene in *Saccharomyces Cerevisiae*", *Current Microbiology*, 25:279-282 (1992).

Chen et al., "Sequencing of a 1,3-1,4-β-D-Glucanase (Lichenase) from the Anaerobic Fungus *Orpinomyces* Strain PC-2: Properties of the Enzyme Expressed in *Escherichia coli* and Evidence that the Gene has a Bacterial Origin", *Journal of Bacteriology*, 179(19):6028-6034 (1997).

Chen et al., "Complete Sequence of the Binary Vector pBI121 and its Application in Cloning T-DNA Insertion from Transgenic Plants", *Molecular Breeding*, 11, 287-293 (2003).

Chen et al., "Cloning, Purification, and Characterization of Thermostable Hypoxanthine-guanine Phosphoribosyltransferase from *Thermoanaerobacter tengcongensis*", *Protein Expression Purification*, 32(2):239-245 (2003).

Chen et al., *Acta Botanica Sinica*, 40(8):711-714 (2008).

Chica et al., "Semi-rational Approaches to Engineering Enzyme Activity: Combining the Benefits of Directed Evolution and Rational Design", *Current Opinion Biotechnology*, 16(4):378-384 (2005).

Chichester et al , "Immunogenicity of a Subunit Vaccine against *Bacillus anthracis*", *Vaccine* (2007), 25:3111-3114.

Clemente et al., "Production of the Main Surface Antigen of *Toxoplasma gondii* in Tobacco Leaves and Analysis of its Antigenicity and Immunogenicity", *Mol. Biotechnol.*, 30:41-49 (2005).

Crameri et al., "Improved Green Fluorescent Protein by Molecular Evolution Using DNA Shuffling", *Nature Biotechnol.*, 14(3):315-319 (1996).

Crossway, "Integration of Foreign DNA Following Microinjection of Tobacco Mesophyll Protoplasts", *Mol. Gen. Genet.*, 202:179-185 (1986).

Curtis and Nam, "Transgenic Radish (*Raphanus sativus L. longipinnatus* Bailey) by Floral-dip method—plant development and surfactant are important in optimizing transformation Efficiency", *Transgenic Research*, 10(4):363-371 (2001).

Dawson et al., "cDNA Cloning of the Complete Genome of Tobacco Mosaic Virus and Production of Infectious Transcripts", *Proc. Natl Acad. Sci., USA*, 83:1832-1836 (1986).

Dreau et al., "Human Papilloma Virus in Melanoma Biopsy Specimens and its Relation to Melanoma Progression", *Annals of Surgery*, 231:664-671 (2000).

Eckert et al., "DNA Polymerase Fidelity and the Polymerase Chain Reaction", *PCR Methods and Applications*, 1:17-24 (1991).

Filgueira et al., "Bovine Herpes Virus gD Protein Produced in Plants Using a Recombinant Tobacco Mosaic Virus (TMV) Vector Possesses Authentic Antigenicity", *Vaccine*, 21:4201-4209 (2003).

Fischer R. et al., "Molecular Farming of Pharmaceutical Proteins", *Transgenic Res.*; 9(4-5):279-299 (2000).

Flick-Smith et al., "A Recombinant Carboxy-Terminal Domain of the Protective Antigen of *Bacillus anthracis* Protects Mice Against Anthrax Infection", *Infection and Immunity*, 70:1653-1656, Mar. 2002.

Floss et al., "Production of Vaccines and Therapeutic Antibodies for Veterinary Applications in Transgenic Plants: an overview", *Transgenic Res.*, 16:315-332 (2007).

Fraley et al., "Liposome-mediated Delivery of Tobacco Mosaic Virus RNA into Tobacco Protoplasts: A Sensitive Assay for Monitoring Liposome-protoplast Interactions", *Proc. Natl. Acad. Sci. USA*, 79: 1859-1863 (1982).

Fraley et al., "Expression of Bacterial Genes in Plant Cells", *Proc. Natl. Acad. Sci. USA*, 80: 4803-4807 (1983).

Franconi et al., "Plant-derived Human Papillomavirus 16 E7 Oncoprotein Induces Immune Response and Specific Tumor Protection", *Cancer Research*, 62:3654-3658, Jul. 1, 2002.

Franken et al., "Recombinant Proteins from Transgenic Plants", *Current Opinion in Biotechnology*, 8:411-416 (1997).

Fromm et al., "Expression of Genes Transferred into Monocot and Dicot Plant Cells by Electroporation", *Proc. Natl. Acad. Sci. USA*, 82: 5824-5828 (1985).

Fujiyama et al., "In Planta Production of Immunogenic Poliovirus Peptide Using Tobacco Mosaic Virus-Based Vector System", *Journal of Bioscience and Bioengineering*, 101:398-402 (2006).
Gatz, et al., "Chemical Control of Gene Expression", *Annual Review of Plant Physiology & Plant Molecular Biology*, 48: 89-108 (1997).
Gewolb, "Plant Scientists See Big Potential in Tiny Plastids", *Science*, 295:258-259 (2002).
Gigliotti et al., "Protective Human Hybridoma Antibody to Tetanus Toxin", *J. Clin. Invest*., 70:1306-1309, Dec. 1982.
Gilleland et al. "Chimeric Aminal and Plant Viruses Expressing Epitopes of Outer Membrane Protein F as a Combined Vaccine against *Pseudomanas aeruginosa* Lung Infection", *FEMS Immunology Medical Microbiology*, 27:291-297 (2000).
Gils et al., "High-yield Production of Authentic Human Growth Hormone using a Plant Virus-based Expression System", *Plant Biotechnology Journal*, 3:613-620 (2005).
Gleba et al, *Current Opinion in Plant Biology*, 2004, 7:182-188.
Gleba et al, "Magnification—a new platform for expressing recombinant vaccines in plants", *Vaccine*, 23:2042-2048 (2005).
Gleba et al., "Viral Vectors for the Expression of Proteins in Plants", *Current Opinion Biotechnology*, 18:134-141 (2007).
Goldenkova et al., "A Thermastable *Clostridium thermacellum* Licenase-based Reporter System for Studying the Gene Expression Regulation in Prokaryotic and Eukaryotic Cells", *Molecular Biology*, 36:698-704 (2002).
Golovkin et al., "Smallpox Subunit Vaccine Produced in Planta Confers Protection in Mice", *Proc. Natl. Acad. Sci. USA*, 2007, 104:6864-6869.
Gomord et al, The C-terminal HDEL Sequence is Sufficient for Retention of Secretory Proteins in the Endoplasmic Reticulum (ER) but promotes Vacuolar Targeting of ProTeins that Escape the ER, *The Plant Journal*, 11(2):313-325 (1997).
Grill et al., "Use of Plant Viruses for Production of Plant-Derived Vaccines", *Critical Reviews in Plant Sciences*, 24:309-323 (2005).
Grimsley et al., ""Agroinfection," an Alternative Route for Viral Infection of Plants by using the Ti Plasmid", *Proc. Natl. Acad. Sci., USA*, 83:3282-3286 (1986).
Gu et al., "Protection against Anthrax Toxin by Vaccination with a DNA Plasmid Encoding Anthrax Protective Antigen", *Vaccine*, 17:340-344 (1999).
Hahn et al., "Native-like in vivo folding of a circularly permuted jellyroll Protein Shown by Crystal Structure Analaysis", *Proc. Natl. Acad. Sci., USA*, 91(22):10417-10421 (1994).
Hansen et al., "Attachment of Antibodies to Sterically Stabilized Liposomes: Evaluation, Comparison and Optimization of Coupling Procedures", *Biochim, Biophys. Acta*., 1239(2):133-144 (1995).
Haq et al., "Oral Immunization with a Recombinant Bacterial Antigen Produced in Transgenic Plants", *Science*, 268:714-716 (1995).
Haseloff et al., "Removal of a Cryptic Intron and Subcellular Localization of Green Flourescent Protein are required to mark Transgenic *Arabidopsis* Plants Brightly", *Proc. Natl. Acad. Sci., USA*, 94(6):2122-2127 (1997).
Hatanaka et al., "A Mutant Phospholipase D with enhanced thermostability from *Streptomyces* sp.", *Biochimica et Biophysica Acta*., 1696(1):75-82 (2004).
Hayes et al., "Gene Amplification and Expression in Plants by a Replicating Geminivirus Vector", *Nature*, 1988, 334:179-182.
Heffernan et al., "Effects of Oral Administration of a Synthetic Fragment of Human Growth Hormone on Lipid Metabolism", *Am. J. Physiol. Endocrinal. Metab*., 2000, 279:E501-E507.
Hellens et al., "pGreen: a versatile and flexible binary Ti vector for *Agrobacterium*-mediated plant transformation", *Plant Molecular Biology* 2000, 42: 819-832.
Henne et al., "The Genome Sequence of the Extremem Thermophile *Thermus thermophilus*", *Nature Biotechnology*, Apr. 4, 2004, 22(5:)547-553.
Hinchee et al., "Production of Transgenic Soybean Plants using *Agrobacterium*-Mediated DNA Transfer", *Bio/Technology*, 1988, 6:915-922.
Hobson et al., "The Role of Serum Haemagglutination-inhibiting antibody in protection against challenge infection with influenza A2 and B viruses", *J. Hyg*., 1972, 70:767-777.
Huang et al., "Virus-like Particle Expression and Assembly in Plants: Hepatitis B and Norwalk Viruses", *Vaccine*, 2005, 23:1851-1858.
Hull et al., "Human-derived, plant-produced Monoclonal Antibody for the Treatment of Anthrax", *Vaccine*, 2005, 23:2082-2086.
Hunter et al., "Messenger RNA for the Coat Protein of Tobacco Mosaic Virus", *Nature* 1976, 260: 759-764.
Iqbal et al., "Kinetics of Enhanced Thermostability of an Extracellular Glucoamylase from *Arachniotus* sp.", *Biotechnol. Lett*., 2003, 25 19 :1667-1670.

Ishida et al., "A Combinatorial Approach to Producing Sterically Stabilized (Stealth) Immunoliposomal Drugs", *FEBS Lett.*, 1999, 460(1):129-133.
Ishikawa et al., "In Vitro Mutagenesis of the Putative Replicase Genes of Tobacco Mosaic Virus", *Nucleic Acids Res.* 1986, 14: 8291-8305.
Jacobson et al., "The Pneumococcal Conjugate Vaccine", *Minerva Peditr.*, 2002, 54:295-303.
Jaspars et al., "Plant Viruses with a Multipartite Genome", *Virus Res.* 1974, 19: 37-149.
Jefferson et al., "GUS fusions: β-glucuronidase as a sensitive and versatile gene fusion marker in higher plants", *EMBO J.*, 1987, 6:3901-3907.
Johnson et al., "Respiratory Syncytial Vaccine (RSV) G Glycoprotein is not Necessary for Vaccine-Enhanced Disease Induced by Immunization with Formalin-Inactivated RSV", *J. Virol.*, 2004, 78(11):6024-6032.
Joshi, et al., "Context Sequences of Translation Initiation Codon in Plants", *Plant Molecular Biology* 1997, 35(6): 993-1001.
Kao et al., "A Method for High-Frequency Intergeneric Fusion of Plant Protoplasts", *Planta*, 1974, 115:355-367.
Kapila et al., "An *Agrobacterium*-mediated Transient Gene Expression System for Intact Leaves", *Plant Sci.*, 1997, 122:101-108.
Kapusta et al., "A Plant-derived Edible Vaccine Against Hepatitis B Virus", *FASEB J.*, 1999, 13:1796-1799.
Karlin and Altschul, "Methods for Assessing the Statistical Significance of Molecular Sequence Features by Using General Scoring Schemes", *Proc. Natl. Acad. Sci., USA*, 1990, 87:2264-2268.
Karlin and Altschul, "Applications and Statistics for Multiple High-scoring Segments in Molecular Sequences", *Proc. Natl. Acad. Sci., USA*, 1993, 90:5873-5877.
Kelly et al., "*Haemophilus influenzae* Type B Conjugate Vaccines", *Immunology*, 2000, 113:163-174.
Khandelwal et al., "Systemic and Oral Immunogenicity of Hemagglutinin Protein of Rinderpest Virus Expressed by Transgenic Peanut Plants in a Mouse Model", *Virology*, 2004, 323:284-291.
Kikkert et al., "Biological Prjectiles (Phage, Yeast, Bacteria) for Genetic Transformation of Plants", *In Vitro Cell. Dev. Bio.—Plant*, 1999, 35(1):43-50.
Kiyosue et al., "LKP1 (LOV kelch protein 1): a factor involved in the regulation of flowering time in *Arabidopsis*", *The Plant Journal*, 2000, 23:807-815.
Kjemtrup et al, "Gene Silencing from Plant DNA carried by a Geminivirus", *The Plant Journal*, 1998, 14(1):91-100.
Klein et al., "High-velocity Microprojectiles for Delivering Nucleic Acids into Living Cells", *Nature*, 327:70-73 (1987).
Klimpel, et al., "Anthrax Toxin Lethal Factor Contains a Zinc Metalloprotease Consensus Sequence which is required for Lethal Toxin Activity", *Mol. Microbiol* 1994, 13: 1093-1100.
Knapp et al., "Conundrum of the Lack of Defective RNAs (Drnas) Associated with Tobamovirus Infections: dRNAs That Can Move are Not Replicated by the Wild-type Virus; dRNAs That are Replicated by the Wild-Type Virus Do Not Move", *Journal of Virology*, 2001, 75:5518-5525.
Knudsen and Muller, "Transformation of the Developming Barley Endosperm by Particle Bombardment", *Planta*, 1991, 185:330-336.
Koev and Miller, "A Positive-Stand RNA Virus with Three Very Different Subgenomic RNA Promoters", *Journal of Virology*, 2000, 74(13):5988-5996.
Kohl et al., "Plant-Produced Cottontail Rabbit Papillomavirus L1 Protein Protects against Tumor Challenge: a Proof-of-Concept Study", *Clin. Vaccine Immunol.*, 2006, 13:845-853.
Kohler and Milstein, "Continuous Cultures of Fused Cells Secreting Antibody of Predefined Specificity", *Nature*, 1975, 256:495-497.
Koo et al., "Protective Immunity against Murine Hepatitis Virus (MHV) induced by Intranasal or Subcutaneous Administration of Hybrids of Tobacco Mosaic Virus that Carries an MHV Epitope", *Proc. Natl. Acad. Sci., USA*, 1999, 96:7774-7779.
Koya et al., "Plant-Based Vaccine: Mice Immunized with Chloroplast-Dirived Anthrax Protective Antigen Survive Anthrax Lethal Toxin Challenge", *Infection and Immunity*, 2005, 73:8266-8274.
Krens et al., "In Vitro Transformation of Plant Protoplasts with Ti-plasmid DNA", *Nature*, 1982, 296:72-74.
Kumagai, et al., "Rapid, high-level Expression of Glycosylated Rice α-amylase in Transfected Plants by an RNA Viral Vector", *Gene* 2000, 245: 169-174.
Kumar et al. "Expression of Hepatitis B Surface Antigen in Tobacco Cell Suspension Cultures", *Protein Expr Purif.*, 2003, 32:10-17.
Lama et al., "Purification and Characterization of Thermostable Xylanase and α-xylosidase by the Terhmaphilic *Bacterium Bacillus thermantarcticus*", *Research in Microbiology*, 2004, 155(4):283-289.
Lambkin et al., "Strong Local and Systemic Protective Immunity Induced in the Ferret Model by an Intranasal Virosome-formulated Influenza Subnit Vaccine", *Vaccine*, 2004, 22:4390-4396.
Langeveld et al., "Inactivated Recombinant Plant Virus Protects Dogs from a Lethal Challenge with Canine Parvobvirus", *Vaccine*, 2001, 19:3661-3670.
Lawton et al., "Expression of a Soybean β-conclycinin Gene under the Control of the Cauliflower Mosaic Virus 35S and 19S Promoters in Transformed Petunia Tissues", *Plant Molecular Biology*, 1987, 9: 315-324.
Lee et al., "Characterization of a Thermostable L-Arabinose (D-Galactose) Isomerase from the Hyperthermophilic *Eubacterium Thermotoga maritima*", *Applied and Environmental Microbiology*, 2004, 70(3):1397-1404.
Leite et al., *Molecular Breeding*, 2000, vol. 6, pp. 47-53.
Leslie et al., "AUtoantigens IA-2 and GAD in Type I (insulin-dependent) diabetes", *Diabetologia*, 1999, 42:3-14.
Lewandowski and Dawson, "Deletion of Internal Sequences Results in Tobacco Mosaic Virus Defective RNAs that Accumulate to High Levels without Interfering with Replication of the Helper Virus", *Virology*, 1998, 251:427-437.
Li et al., "Expression of a Human Lactoferrin N-lobe in *Nicotianna benthmiana* with Potato Virus X-based Agroinfection", *Biotechnology Letters*, 2004, 26:953-957.
Liljeqvist et al., "Fusion to the Cholera Toxin B Subunit: Influence on Pentamerization and GM1 Binding", Journal Immunology Methods, 1997, 210:125-135.
Lim et al., "An Anthrax Lethal Factor-Neutralizing Monoclonal Antibody Protects Rats before and after Challenge with Anthrax Toxin", *Infection and Immunity*, 2005, 73:6547-6551.
Little et al., "Passive Protection by Polyclonal Antibodies against *Bacillus anthracis* Infection in Guinea Pigs", Infection and Immunity, Dec. 1997, 65:5171-5175.
Loesch-Fries, et al., *Virology* 1985, 146: 177-187.
Lorence and Verpoorte, "Gene Tranfer and Expression in Plants", *Methods Mol. Biol.*, 2004, 267:329-350.
Luo et al., "FLP-mediated Recombination for Use in Hybrid Plant Production", The Plant Journal, 2000, 23:423-430.
Ma et al., "Transgenic Plants Expressing Autoantigens Fed to Mice to Induce Oral Immune Tolerance", *Nature Medicine*, vol. 3, No. 7, pp. 793-796, Jul. 1997.
Maassab et al., "Evaluation of a Cold-Recombinant Influenze Virus Vaccine in Ferrets", The Journal of Infection Diseases, vol. 146, No. 6, pp. 780-790, Dec. 1982.
MacFarlane et al., "Efficient Expression of Foreign Proteins in Roots from Tobravirus Vectors", *Virology*, 2000, 267:29-35.
Maliga et al., "Transient Cycloheximide Resistance in a Tobacco Cell Line", *Mol. Gen. Genet.*, 1976, 149, 267-271.
Mallory et al., "The Amplicon-plus System for High-Level Expression of Transgenes in Plants", *Nature Biotech.*, 2002, 20:622-625.
Marillionnet et al., "In Planta Engineering of Viral RNA Replicons: Efficient assembly by Recombination of DNA Modules Delivered by *Agrobacterium*" *Proc. Natl. Acad. Sci., USA*, May 4, 2004, 101, No. 18, pp. 6852-6857.
Marillionnet et al., "Systemic *Agrobacterium tumefaciens*-Mediated Transfection of Viral Replicons for Efficient Transient Expression in Plants", *Nature Biotechnology*, 2005, 23:718-723.
Massa et al., "Anti-Cancer Activity of Plant-Produced HPV16 E7 Vaccine", *Vaccine*, 2007, 25:3018-3021.
Matsuhara et al., "Heat-shock Tagging: a Simple Method for Expression and Isolation of Plant Genome DNA Flanked by T-DNA Insertions", *The Plant Journal*, 2000, 22(1):79-86.

Mattila et al., *Nucleic Acids Res.*, 1991, 19:4967-4978.
McCormick et al., "Rapid Production of Specific Vaccines for Lymphoma by Expression of the Tumor-derived Single-Chain Fv Epitopes in Tobacco Plants", *Proc. Natl. Acad. Sci. USA*, Jan. 1999, 96: 703-708.
Mellin et al., "Human Papillomavirus (HPV) DNA in Tonsillar Cancer: Correlates, Rick of Relapse, and Survival", *International Journal of Cancer*, 2000, 89:300-304.
Menczel et al. "Streptomycin Resistant and Sensitive Somatic Hybrids of *Nicotiana tabacum* + *Nicotiana*: Correlation of Resistance to *N. tabacum* Plastids", *Theor. Appl. Genet.*, 1981, 59, 191-195.
Meshi et al., "Function of the 30 KD Protein of Tobacco Mosaic Virus: Involvement in Cell-to-Cell Movement and Dispensability for Replication", *The EMBO Journal*, 1987, vol. 6; No. 9; pp. 2557-2563.
Mett et al., "A Plant-produced Plague Vaccine Candidate Confers Protection to Monkeys", *Vaccine*, 2007, 25(16):3014-3017.
Microbiology & Immunology: BS335: Plant Viruses, http://www-micro.msb.le.ac.uk/335/Plant.html; downloaded May 18, 2002.
Moayeri et al., "The Roles of Anthrax Toxin in Pathogenesis", Current Opinion in Microbiology, 2004, 7(1):19-24.
Molina et al., "Induction of Neutralizing Antibodies by a Tobacco Chloroplast-derived Vaccine Based on a B Cell Epitope from Canine Parvovirus", *Virology*, 2005, 342:266-275.
Moloney et al., "High Efficiency Transformation of *Brassica napus* using *Agrobacterium* Vectors", *Plant Cell Report*, 1989, 8:238-242.
Moreira et al., "A Thermostable Maltose-tolerant α-amylase from *Aspergillus tamarii*", *J. Basic Microbiology*, 2004, 44:29-35.
Mori et al., "Inducible High-Level mRNA amplification system by Viral Replicase in Transgenic Plants", *Plant Journal*, 2001, 27(1):79-86.
Musiychuk et al., "Preparation and Properties of *Clostribium thermocellum* Licheenase Deletion Variants and Their Use for construction of Bifunctional Hybrid Proteins", *Biochemistry (Mosc)*, 2000, 65(12):1397-1402.
Musiychuk et al., "A Launch Vector for the Production of Vaccine Antigens in Plants", *Influenza and Other Respiratory Viruses*, 2007, 1:(1):19-25.
Nashar et al., "Current Progress in the Development of the B Subunits of Cholera Toxin and *Escherichia coli* Heat-labile Enterotoxin as Carriers for the Oral Delivery of Heterologous Antigens and Epitopes", *Vaccine*, 1993, 11:235.
Nass, "Anthrax Vaccine Model of a Response to the Biologic Warfare Threat", *Infect. Dis. Clin. North Am.*, 1999, 13,187-208.
Neeleman et al., "Role of Alfalfa Mosaic Virus Coat Protein Gene in Symptom Formation", *Virology* 1991, 181: 687-693.
Neeleman et al., "Infection of Tobacco with Alfalfa Mosaic Virus cDNAs Sheds Light on the Early Function of the Coat Protein", *Virology* 1993, 196: 883-887.
Nemchinov et al., "Development of a Plant-derived Subunit Vaccine Candidate against Hepatitis C Virus", *Arch. Virol.*, 2000, 145:2557-2573.
Okada, "Historical Overview of Research on the Tobacco Mosaic Virus Genome: Genome Organization, Infectivity and Gene Manipulation", *Philosophical Transactions of the Royal Society Lond. B*, 1999, 354:569-582.
Palmer et al., "Protection of Rabbits against Cutaneous Papillomavirus Infection using Recombinant Tobacco Mosaic Virus containing L2 Capsid Epitopes", *Vaccine*, 2006, 24:5516-5525.
Park et al., "Molecular Biology of Cervical Cancer and Its Precursors", *Cancer*, 1995, 76:1902-1903.
Park et al., "Heterologous Gene Expression in *Thermus thermophilus*: β-galactosidase, dibenzothiophene Monooxygenase, PNB Carboxy Esterase, 2-aminobiphenyl-2,3-diol dioxygenase, and chloramphenicol acetyl transferase", *J. Ind. Microbiol. Biotechnol.*, 2004, 31(4):189-97.
Parmenter D.L., "Production of Biologically Active Hirudin in Plant Seeds using Oleosin Partitioning", *Plant Mol Biol*. Dec. 1995, 29(6):1167-1180.
Petosa et al., "Crystal Structure of the Anthrax Toxin Protective Antigen", *Nature*, 1997, 385:833-838.

Pew Initiative on Food and Biotechnology, (Feb. 28, 2003), "Biopharming Could Reap Benefits but Must be Tightly Regulated," www.pewagbiotech.org.
Pfitzner et al., "Isolation and Characterization of cDNA Clones encoding Pathogenesis-related Proteins from Tobacco Mosaic Virus infected Tobacco Plants", *Nucleic Acids Res.*, 1987, 15:4449-4465.
Pilon-Smits et al., "Overexpression of ATP Sulfurylase in Indian Mustard Leads to Increased Selenate Updake, Reduction, and Tolerance", *Plant Physiology*, 1999, 119(1): 123-132.
Piruzian et al., "The Use of a Thermostable β-glucanase Gene from *Clostridium thermocellum* as a Reporter Gene in Plants", *Mol. Gen. Genet.*, 1998, 257(5):561-567.
Pitson et al., "Noncellulolytic Fungal β-glucanases: Their Physiology and Regulation", *Enzyme and Microbial Technol.*, 1993, 15(3):178-192.
Pogue et al., "Making an Ally from an Enemy: Plant Virology and the New Agriculture", *Annu. Rev. Phytopathol.*, 2002, 40:45-74.
Pogue et al., "Tobamovirus Transient Expression Vectors: Tools for Plant Biology and High-Level Expression of Foreign Proteins in Plants", *Plant Molecular Biology Manual*. 1998, L4, 1-27.
Porta et al., "Use of Viral Replicons for the Expression of Genes in Plants", *Molecular Biotechnology*. Jun. 1996; 5(3):209-21.
Potrykus et al., "Molecular and General Genetics of a Hybrid Foreign Gene Introduced into Tobacco by Direct Gene Transfer", *Mol. Gen. Genet.*, 1985, 199:169-177.
Potter et al., "Immunity to Influenza in Ferrets", *Br. J. Exp. Pathol.*, 1972, 53:168-179.
Potter et al , "Immunity to Influenza in Ferrets", *Arch. Gesamte Virusforsch.*, 1973, 42:285-296.
Potter et al , "Immunity to Influenza in Ferrets", *J. Hyq. Lond.*, 1973, 71:97-106.
Qing et al., "Transformation of Pakchoi (*Brassica rapa* L. ssp. *chinensis*) by *Agrobacterium* Infiltration", *Molecular Breeding*, 2000, 1:67-72.
Rennermalm et al., "Antibodies against a Truncated *Staphylococcus aureus* Fibronectin-binding Protein Protect against Dissemination of Infection in the Rat", *Vaccine*, 2001, 19:3376-3383.
Richter et al., "Production of Hepatitis B Surface Antifen in Transgenic Plants for Oral Immunization", *Nature Biotechnology*, Nov. 2000, 18:1167-1171.
Riggs and Bates, "Stable Transformation of Tobacco by Electoporation: Evidence for Plasmid Concateration", *Proc. Natl. Acad. Sci., USA*, Aug. 1986, 83:5602-5606.
Riva et al., "*Agrobacterium tumefaciens*: a Natural Tool for Plant Transformation", *EJB Electronic J. Biotech.*, 1998, 1(3), 118-133.
Saejung et al., "Production of Dengue 2 Envelope Domain III in Plant using TMV-based Vector System", *Vaccine*, 2007, 25:6646-6654.
Saito, et al., "Long-Distance Movement and Viral Assembly of Tobacco Mosaic Visus Mutants", *Virology* 1990, 176: 329-336.
Sanford, "The Biolistic Process", *Trends in Biotech.*, 1988, 6:299-302.
Santi et al., "Protection conferred by Recombinant *Yersinia pestis* Antigens Produced by a Rapid and Highly Scalable Plant Expression System", *Proc. Natl. Acad. Sci., USA*, 2006, 103(4):861-866.
Schell et al., "Transgenic Plants as Tools to Study the Molecular Organization of Plant Genes", *Science* 1987, 237: 1176-1183.
Schillberg et al., "Opportunities for Recombinant Antigen and Antibody Expression in Transgenic Plants-technology assessment", *Vaccine*, 2005, 23:1764-1769.
Schimming et al., "Structure of the *Clostribium thermocellum* Gene licB and the encoded β-1,3-1,4-glucanase", *Eur. J. Biochem.*, 1992, 204(1):13-19.
Schob et al., "Silencing of Transgenes Introduced into Leaves by Agroinfiltration: a Simple, Rapid Method for Investigating Sequence Requirements for Gene Silencing", *Mol. Gen. Genet.*, 1997, 256:581-585.
Scholthof and Scholthof, "Plant Virus Gene Vectors for Transient Expression of Foreign Proteins in Plants", *Ann. Rev. Phytopathol.*, 1996, 34:299-323.
Seedorf et al., "Human Papillomavirus Type 16 DNA Sequence", *Virology*, 1985, 145:181-185.

Shima et al., "Hyperthermophilic and Salt-dependent Formyltransferase from *Methanopyrus kandleri*", Biochemical Society Transaction, 2004, vol. 32, Pt.2, pp. 269-272.

Singh et al., "The Chymotrypsin-sensitive Site, FFD[315], in Anthrax Toxin Protective Antigen is Required for Translocation of Lethal Factor", *The Journal of Biological Chemisty*,. Nov. 18, 1994, vol. 269, No. 48: 29039-29046.

Singh et al., "Study of Immunization against Anthrax with the Purified Recombinant Protective Antigen of *Bacillus anthracis*", *Infection and Immunity*, Jul. 1998, vol. 66, No. 7, 3447-3448.

Sit et al., "A Single Amino Acid Mutation in the Carnation Ringspot Virus Capsid Protein Allows Virion Formation but Prevents Systemic Infection", *Virology*, 2001, 75:9538-9542.

Smith et al., "Modified Tobacco Mosaic Virus Particles as Scaffolds for Display of Protein Antigens for Vaccine Applications", *Virology*, 2006, 348:475-488.

Soini et al., "Presence of Human Papillomavirus DNA and Abnormal p53 Protein Accumulation in Lung Carcinoma", *Thorax*, 1996, 51:887-893.

Srivastava, "Properties of Thermostable Hemicellulolytic Enzymes from Thellnomonospora Strain 29 Grown in Solid State Fermentation on Coffee Processing Solid Waste", *Biotechnol. Adv.*, 1993, 11(3):441-465.

Staczek et al, "Immunization with a Chimeric Tobacco Mosaic Virus Containing an Epitope of Outer Membrane Protein F of *Pseudomonas aeruginosa* Provides Protection Against Challenge with *P. aeruginosa*", *Vaccine*, 2000, 18:2266-2274.

Stahl et al., "Immunogenicity of Peptide Fusions to Hepatitis B Virus Core Antigen" *Proc. Natl. Acad. Sci., USA*, Aug. 1989, 86:6283-6287.

Sweet et al., "Pathogenicity of Influenza Virus", *Microbiological Review*, 1980, 44:303-330.

Tacket et al., "Human Immune Responses to a Noval Norwalk Virus Vaccine Delivered in Transgenic Potatoes", *J. Infect. Dis.*, 2000, 182:302-305.

Thanavala et al., "Immunogenicity in Humans of an Edible Vaccine for Hepatitis B", *Proc. Natl. Acad. Sci., USA*, 2005, vol. 102, No. 9, pp. 3378-3381.

Thomas et al., "HPV-18 E6 Mediated Inhibition of p53 DNA Binding Activity is Independent of E6 Induced Degradation", *Oncogene*, 1995, 10:261-268.

Thomas et al., "Size Constraints for Targeting Post-Transcriptional Gene Silencing and for PNA-directed Methylation in *Nicotiana benthamiana* using a Potato Virus X Vector", The Plant Journal, 2001, 25(4):417-425.

Tobamoviruses, http://opbs.okstate.edu/virevol/tobamo.html; downloaded May 18, 2002.

Tomme et al., "Comparison of a Fungal (Family I) and Bacterial (Family II) Cellulose-Binding Domain", Journal of Bacteriology, Aug. 1995, 177:4356-4363.

Torchilin et al., (ρ-Nitrophenylcarbonyl-PEG-PE-liposomes: Fash and Simple Attachment of Specific Ligards, including Monoclonal Antibodies, to Distal Ends of PEG Chains via ρ-Nitrophenylcarbonyl Groups, *Biochimica et Biophysica Acta* 2001, 1511(2):397-411.

Tregoning et al., "New Advances in the Production of Edible Plant Vaccines: Chloroplast Expression of a Tetanus Vaccine Antigen, TetC", *Phytochemistry*, 2004, 65:989-994.

Tsai et al., "Crystal Structure of a Natural Circularly Permuted Jellyroll Protein: 1,3-1,4-β-D-Glucanase from *Fibrobacter succinogenes*", *J. Mol. Biol.*, 2003, 330(3):607-620.

Tuboly et al , "Immunogenicity of Procine Tranmissible Gastroenteritis Virus Spike Protein Expressed in Plants", *Vaccine* 2000, 18:2023-2028.

Turpen et al., "Transfection of Whole Plants from Wounds Inoculated with *Agrobacterium tumefaciens* Containing cDNA of Tobacco Mosaic Virus", *Journal of Virological Methods*, 1993, 42:227-240.

Turpen et al., "Malarial Epitopes Expressed on the Surface of Recobinant Tobacco Mosaic Virus", *Biotechnology*, 1995, 13:53-57.

Turpen, "Tobacco Mosaic Virus and the Virescence of Biotechnology", *Phil. Trans. R. Soc. Lond. B.*, 1999, 354:665-673.

Ulrich et al., "Core Particles of Hepatitis B Virus as Carrier for Foreign Epitopes", *Advances in Virus Research*, 1998, 50:141-182.

Usha et al., "Expression of an Animal Virus Antigenic Site on the Surface of a Plant Virus Particle", *Virology*, Nov. 1993; 197(1):366-374.

Van Der Kuyl et al., "Complementation and Recobination between Alfalfa Mosaic Virus RNA3 Mutants in Tobacco Plants", *Virology*, 1991, 183:731-738.

Van Der Kuyl et al., "Role of Alfalfa Mosaic Virus Coat Protein in Regulation of the Balance between Viral Plus and Minus Strand RNA Synthesis", *Virology*, 1991, 185:496-499.

Van Der Vossen, et al., "Early and Late Functions of Alfalfa Mosaic Virus Coat Protein can be Mutated Separately", *Virology* 1994, 202:891-903.

Volten-Doting, Plant Viruses Online (http://image.fs.uidaho.edu/vide/descr009.htm) (downloaded May 18, 2002).

Wang et al., "Structural Basis for Thermostability of β-Glycosidase from the Thermophilic *Eubacterium thermus nonproteolyticus* HG102", *Journal of Bacteriology*, 2003, 185(14):4248-4255.

Ward and Moo-Young, "Thermostable Enzymes", *Biotechnol. Adv.*, 1988, 6(1):39-69.

Wei et al., (2002), *Journal of Northeast Forestry University*, 30:56-59 (English translation of specific passage referred to by Examiner in First Office Action of Chinese Application No. 03822979.X (national phase of PCT/US2003/023520). (The First Office Action and translation of the same are attached to the aforementioned reference.).

Weismuller et al., "Peptide Vaccines and Peptide Libraries", *Biol. Chem.*, 2001, 382(4):571-579.

Wigdorovitz et al., "Introduction of a Protective Antibody Response to Foot and Mouth Disease Virus in Mice Following Oral or Paranteral Immunization with Alfalfa Transgenic Plants Expressing the Viral Structural Protein VP1", *Virology*, 1999, 255:347-353.

Wilson et al., "Structure of the Haemagglutinin Membrane Glycoprotein of Influenze Virus at 3A Resolution", *Nature*, 1981, 289:366-373.

Wu et al., "Expression of a foot-and mouth Disease Virus Epitopes in Tobacco by a Tobacco Mosaic Virus-based Vector", *Vaccine*, 2003, 21:4390-4398.

Yang et al., "Introduction of Protective Immunity in Swine by Recombinant Bamboo Mosaic Virus Expressing Foot-and-mouth Disease Virus Epitopes", *BMC Biotechnology*, 2007, 7:62-72.

Yano and Poulos, "New Understandings of Thermostable and Peizostable Enzymes", *Current Opinion in Biotechnology*, 2003, 14(4):360-365.

Yusibov et al. "The Potential of Plant Virus Vectors for Vaccine Production", *Drugs R&D*, 2006, 7:203-217.

Yusibov et al., "Purification, Characterization, Assembly and Crystallization of Assembled Alfalfa Moaic Virus Coat Protein Expressed in *Escherichia coli*", *J. Gen. Virol.*, 1996, 77:567-573.

Yusibov et at., "Peptide-based Candidate Vaccine against Respiratory Syncytial Virus", *Vaccine*, 2005, 23:2261-2265.

Zaitlin, Plant Viruses Online (http://image.fs.uidaho.edu/vide/descr803.htm); downloaded Jul. 16, 2009.

Zhang et al., "Suppression of Diabetes in Nonobese Diabetic Mice by Oral Administration of Porcine Insulin", *Proc. Natl. Acad. Sci., USA*, 1991, 88:10252-10256.

Zumbach et al., "Antibodies against Oncoproteins E6 and E7 of Human Papillomavirus Types 16 and 18 in Patients with Head-and-Neck Squamous-Cell Carcinoma", *International Journal of Cancer*, 2000, 85:815-818.

Communication dated Jul. 22, 2008 for European Appln. No. 03 781 904.2.

Communication dated Jun. 16, 2008 for European Appln. No. 04 707 807.6.

Examiner's Report dated Aug. 1, 2008 for Australian Appln. No. 2004209660.

Examiner's Report dated Jan. 20, 2009 for Australian Appln. No. 2005216133.

Office Action (Final) dated Jul. 28, 2008 for U.S. Appl. No. 10/294,314.

Office Action (Non-final) dated Jul. 27, 2007 for U.S. Appl. No. 10/294,314.

Office Action (Final) dated Jul. 20, 2006 for U.S. Appl. No. 10/294,314.

Office Action (Non-final) dated Oct. 14, 2005 for U.S. Appl. No. 10/294,314.
Office Action (Non-final) dated Sep. 11, 2006 for U.S. Appl. No. 10/770,600.
Office Action (first) for Chinese Appln. No. 200580005502.2, dated Apr. 11, 2008.
Office Action (second) for Chinese Appln. No. 200580005502.2, dated May 8, 2009.
Supplementary Search Report dated Dec. 12, 2006 for European Appln. No. 04776107.7.
Supplementary Search Report dated Jul. 2, 2007 for European Appln. No. 04707807.6.
Supplementary Search Report dated Nov. 2, 2007 for European Appln. No. 03781904.2.
Supplementary Search Report dated Jul. 16, 2007 for European Appln. No. 03771957.2.
Supplementary Search Report dated Jul. 26, 2007 for European Appln. No. 03781869.7.
U.S. Appl. No. 10/558,109; Yusibov et al; filed May 8, 2007(U.S. National Phase of WO05/26375).
Arazi et al., "Engineering zucchini yellow mosaic potyvirus as a non-pathogenic vector for expression of heterologous proteins in cucurbits," *J. Biotechnol.*, 87(1):67-82, 2001.
Choi et al., "A plant virus vector for systemic expression of foreign genes in cereals," *Plant J.*, 23(4):547-555, 2000.
Christey et al., "Regeneration of transgenic kale (*Brassica oleracea* var. acephala), rape (*B. napus*) and turnip (*B. campestris* var. rapifera) plants via *Agrobacterium rhizogenes* mediated transformation," *Plant Sci.*, 87(2):161-169, 1992.
Cui et al., "Efficient shoot regeneration from hairy roots of *Antirrhinum majus L.* transformed by the rol type MAT vector system," *Plant Cell Reports*, 20(1):55-59, 2001.
Communication with Supplementary European Search Report dated Jul. 16, 2010 for European Appln. No. EP05723389 (6 pgs.).

* cited by examiner

Clonal Root Line Technology (CRLT) for Obtaining Target Producer Lines

Western blot analysis of GFP production in *clonal root line*

Clonal Root Lines Producing hGH and GFP

Screening and Selection of hGH Producing *Clonal Root Lines* by Western Blot Analysis → Indicates selected lines
3d subculture

Western Blot Analysis of hGH Production in Selected *Clonal Root Lines*

Screening and Selection of GCSF Producing *Clonal Root Lines* by Western Blot Analysis

**Western Blot Analysis of GCSF Production in Selected *Clonal Root Lines***

Clonal Cell Line Technology (CCLT) for Obtaining Target Producer Lines

Western blot analysis of GCSF production in *cell lines*

Clonal cell lines producing GFP

Enriched clones under UV light
(3 month after infection)

Regeneration of clonal plant lines from clonal root lines

SYSTEMS AND METHODS FOR CLONAL EXPRESSION IN PLANTS

CROSS-REFERENCE TO RELATED APPLICATION

This application claims priority to and the benefit of U.S. Provisional Patent Application No. 60/546,339 filed Feb. 20, 2004, which is incorporated herein by reference.

BACKGROUND OF THE INVENTION

Research to identify molecules with potential for preventative and therapeutic use (antibodies, enzymes, hormones and vaccine antigens) is of paramount importance to health and medicine. Historically, many of these molecules were recovered from human or animal sources. However, low quantities of target product in the source material coupled with immense costs, and more importantly, safety, have limited the availability of therapeutics and vaccines for prevention and treatment of many diseases around the world.

In the mid-1970s recombinant DNA technology revolutionized the process and made possible the production of target molecules predominantly in bacterial expression systems. Although prokaryotic expression systems continue to be a widely utilized method for recombinant protein production, this platform has its limitations because, for example, of the absence of eukaryotic posttranslational modifications and improper folding of many complex human proteins. During the last three decades many research laboratories have focused their interests on developing alternative systems for expressing recombinant proteins that could overcome the shortcomings of bacterial systems. Emerging out of these studies were animal and insect cell culture systems. Although a number of products such as monoclonal antibodies, vaccines and therapeutics have been produced using these systems, but the high cost of production combined with the requirement of highly sophisticated manufacturing facilities for each target protein motivated the search for different production systems.

In recent years, plants have been increasingly used as a host system for the expression of recombinant proteins. Such expression can be accomplished, for example, either by integrating the gene of interest into a plant genome, to create a transgenic plant that stably expresses the desired protein, or by introducing the gene of interest into a plant vector that can be introduced into, and transiently maintained in, plant cells. Viral vector systems have proven to be particularly useful.

However, there remains a need for developing improved systems for expression of a molecule of interest in plants. For example, viruses may infect non-target plants, potentially posing significant environmental risks. Also, many available engineered plant viruses do not express inserted genes at desired levels, and/or in desired target plants or tissues. In addition, one disadvantage with various existing viral vector systems is that virus stability can be problematic. In general, there is a need in the art for plant expression systems that would allow for greater flexibility and control.

SUMMARY OF THE INVENTION

The present invention encompasses the recognition that the availability of clonal expression systems for plants would offer a number of significant advantages. The invention provides methods and reagents for generating a variety of clonal entities derived from plants. These clonal entities include clonal root lines, clonal root cell lines, clonal plant cell lines, and clonal plants. The invention further provides methods and reagents for expression of polynucleotide and polypeptide products in clonal cell lines derived from various plant tissues (e.g., roots, leaves), and in whole plants derived from single cells (clonal plants). The methods are based on the use of plant viral vectors of various types.

For example, in one aspect, the invention provides a method of obtaining a clonal root line that expresses a polynucleotide of interest comprising steps of: (i) introducing a viral vector that comprises a polynucleotide of interest into a plant or portion thereof; and (ii) generating one or more clonal root lines from the plant. The clonal root lines may be generated, for example, by infecting the plant or plant portion (e.g., a harvested piece of leaf) with an *Agrobacterium* (e.g., *A. rhizogenes*) that causes formation of hairy roots. Clonal root lines can be screened in various ways to identify lines that maintain the virus, lines that express the polynucleotide of interest at high levels, etc. The invention further provides clonal root lines, e.g., clonal root lines produced according to the inventive methods and further encompasses methods of expressing polynucleotides and producing polypeptides of interest using the clonal root lines.

The invention further provides a method of generating a clonal root cell line that expresses a polynucleotide of interest comprising steps of: (i) generating a clonal root line, cells of which contain a viral vector whose genome comprises a polynucleotide of interest; (ii) releasing individual cells from the clonal root line; and (iii) maintaining the cells under conditions suitable for root cell proliferation. The invention provides clonal root cell lines and methods of expressing polynucleotides and producing polypeptides using the clonal root cell lines.

In another aspect, the invention provides a method of generating a clonal plant cell line that expresses a polynucleotide of interest comprising steps of: (i) generating a clonal root line, cells of which contain a viral vector whose genome comprises a polynucleotide of interest; (ii) releasing individual cells from the clonal root line; and (iii) maintaining the cells in culture under conditions appropriate for plant cell proliferation. The invention further provides a method of generating a clonal plant cell line that expresses a polynucleotide of interest comprising steps of: (i) introducing a viral vector that comprises a polynucleotide of interest into cells of a plant cell line maintained in culture; and (ii) enriching for cells that contain the viral vector. Enrichment may be performed, for example, by (i) removing a portion of the cells from the culture; (ii) diluting the removed cells so as to reduce the cell concentration; (iii) allowing the diluted cells to proliferate; and (iv) screening for cells that contain the viral vector. Clonal plant cell lines may be used for production of a polypeptide of interest.

The invention features a number of methods for generating clonal plants, cells of which contain a viral vector that comprises a polynucleotide of interest. For example, the invention provides a method of generating a clonal plant that expresses a polynucleotide of interest comprising steps of: (i) generating a clonal root line, cells of which contain a viral vector whose genome comprises a polynucleotide of interest; (ii) releasing individual cells from the clonal root line; and (iii) maintaining the cells under conditions appropriate for formation of a plant. The invention further provides a method of generating a clonal plant that expresses a polynucleotide of interest comprising steps of: (i) generating a clonal plant cell line, cells of which contain a viral vector whose genome comprises a polynucleotide of interest; and (ii) maintaining the cells under conditions appropriate for formation of a plant. In general, the clonal plants can express any polynucleotide of interest. The clonal plants can be used for production of a polypeptide of interest.

This application refers to various patents, patent applications, and publications. The contents of all of these are incorporated herein by reference. In addition, the following publications are incorporated herein by reference: *Current Protocols in Molecular Biology, Current Protocols in Immunology, Current Protocols in Protein Science*, and *Current Protocols in Cell Biology*, all John Wiley & Sons, N.Y., edition as of July 2002; Sambrook, Russell, and Sambrook, *Molecular Cloning: A Laboratory Manual*, 3$^{rd}$ ed., Cold Spring Harbor Laboratory Press, Cold Spring Harbor, 2001; Slater, A., Scott, N. W., and Fowler, M. R., *Plant Biotechnology*, Oxford University Press, 2003. In the event of a conflict between the instant specification and an incorporated reference the specification shall control.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 6A is a schematic representation of a viral vector useful for generating clonal root lines. FIG. 6B shows a plant into which a viral vector (depicted schematically in FIG. 6A) has been introduced. FIG. 6C shows leaf portions after harvesting from a virus-infected plant. FIG. 6D shows hairy roots generated by individual cells in leaf portions infected with *A. rhizogenes*. FIG. 6E shows clonal root lines. FIG. 6F shows clonal root lines at a higher level of magnification. FIG. 6G shows GFP expression in a clonal root line, cells of which contain a viral vector that encodes GFP.

FIG. 7A shows GFP expression in the clonal root lines after 30 days of propagation in culture (i.e., 30 days after separation of the root from the leaf from which it was derived). FIG. 7B shows GFP expression in the clonal root lines after 60 days of propagation in culture (i.e., 60 days after separation of the root from the leaf from which it was derived). C− represents control lanes containing no protein. MWM represents molecular weight markers. GFP-R represents samples from clonal root lines. GFP-P represents GFP isolated from leaf tissue of a plant infected with the same construct used for generation of the clonal root lines. FIG. 7C is a control showing that the anti-GFP antibodies recognize commercially available GFP protein.

FIG. 8A shows a photograph of two clonal root lines taken under normal light conditions. The plate on the left shows a clonal root line derived from a plant cell into which a viral vector whose genome contains a gene that encodes human growth hormone (hGH) under control of the TMV CP promoter was introduced. The plate on the right shows a clonal root line derived from a plant cell into which a viral vector whose genome contains a gene that encodes green fluorescent protein (GFP) under control of the TMV CP promoter was introduced. FIG. 8B shows a photograph of the same clonal root lines as shown in FIG. 8A taken under UV light, demonstrating expression of GFP.

FIG. 13A shows a viral vector in which a polynucleotide of interest is inserted under control of the TMV CP promoter. FIG. 13B shows a protoplast suspension into which the vector was introduced (left plate) or a control protoplast suspension into which a vector lacking a GFP-encoding polynucleotide was introduced (right plate). The picture was taken under UV light and shows expression of GFP in the protoplasts containing the GFP-encoding expression vector. FIG. 13C shows a protoplast suspension into which the GFP-encoding vector was introduced. The photo was taken under UV light. The inset (FIG. 13D) shows a higher magnification of GFP-expressing cells, also taken under UV light. FIG. 13E is a photograph showing enrichment for plant cell lines that express GFP. The photo was taken under normal light. of individual plant cell lines derived from the protoplast suspension shown in FIG. 13C. FIG. 13F is a photograph of the same plates as shown in FIG. 13C, taken under UV light. Cultures enriched for cell lines expressing GFP are evident as green fluorescing spots.

FIG. 14A shows a Western blot performed 48 hours after introduction of the vector. FIG. 14B shows a Western blot performed using the same cell lines as shown in FIG. 14A performed 57 days after inoculation. GCSF-COM indicates a lane in which recombinant GCSF protein was loaded as a positive control. MWM indicates molecular weight markers. C− indicates a lane in which plant extract made from plants not expressing GCSF was loaded.

FIG. 15 (left) shows enrichment for plant cell lines that express GFP. FIG. 15 (right) shows a callus derived from a clonal plant cell line into which a similar viral vector, not encoding GFP, was introduced. The photographs were taken 3 months after the vector was introduced into the cells from which the clones in FIG. 15 (left) were derived. Both photographs were taken under UV light.

DEFINITIONS

Figure 1:
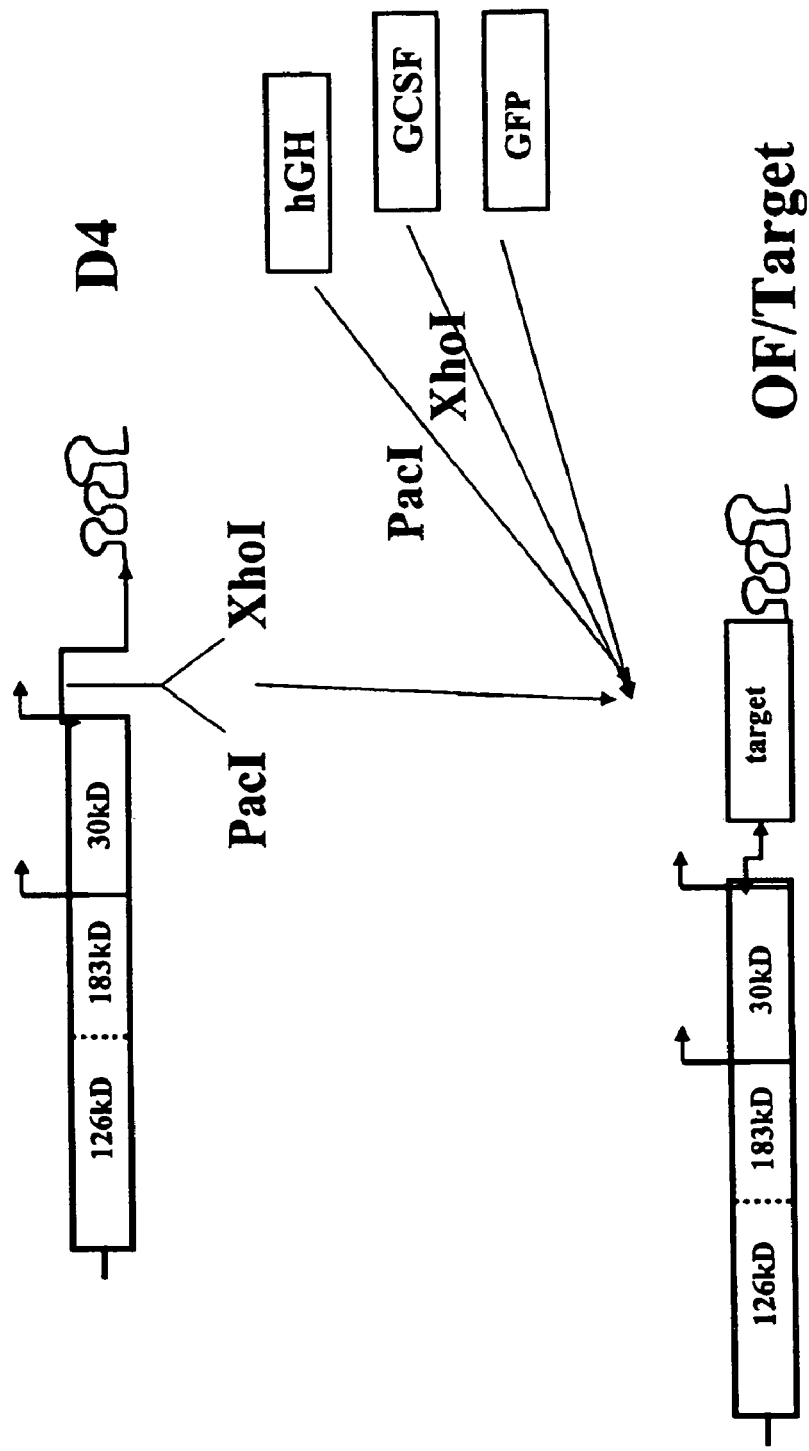
FIG. 1 presents a schematic diagram of the engineering of a TMV based viral construct containing a polynucleotide of interest. The upper portion of the figure shows a diagram of the genomic organization of a TMV based virus construct, D4, and the lower portion shows the same construct following insertion of a polynucleotide of interest (e.g., a gene encoding hGH, GCSF, GFP, etc., indicated as "target"). The 126/183 kDa protein is required for replication of the virus. The 30 kD protein is the movement protein (MP) that mediates cell-to-cell movement. Arrows indicate positions of the subgenomic promoters. Transcription of the inserted polynucleotide is under control of the TMV CP subgenomic promoter. The 3' portion of the construct includes TMV coat protein sequences and untranslated regions. These portions are optional.

Approximately: Approximately" in reference to a number includes numbers that fall within a range of 5% in either direction (greater than or less than) the number unless otherwise stated or otherwise evident from the context (except where such number would exceed 100% of a possible value). Where ranges are stated, the endpoints are included within the range unless otherwise stated or otherwise evident from the context.

Clonal: For the purpose of the present invention, the term clonal as applied, e.g., to a plant or plant tissue such as a root, leaf, stem, etc., means that the plant or plant tissue was derived from a single ancestral cell. In general, the cells or a clonal plant or plant tissue will be genetically identical with the exception of somatic mutations or other genetic alterations that may arise in descendant cells (e.g., through either natural or artificial introduction of a new gene into a descendant cell, telomere shortening, etc.). Typically the genome of the cells will be at least 95% identical, at least 98% identical, at least 99% identical, at least 99.5% identical, at least 99.9% identical.

Gene: For the purposes of the present invention, the term gene has its meaning as understood in the art. In general, a gene is taken to include gene regulatory sequences (e.g., promoters, enhancers, etc.) and/or intron sequences, in addition to coding sequences (open reading frames). It will further be appreciated that the definition of gene can include nucleic acids that do not encode proteins but rather provide templates for transcription of functional RNA molecules such as tRNAs, rRNAs, microRNAs (mRNAs), short hairpin RNAs (shRNAs), short interfering RNAs, (siRNAs), etc. For the purpose of clarity we note that, as used in the present application, the term "gene" generally refers to a nucleic acid that includes a portion that encodes a protein; the term may optionally encompass regulatory sequences such as promoters, enhancers, terminators, etc. This definition is not intended to exclude application of the term "gene" to non-protein coding expression units but rather to clarify that, in most cases, the term as used in this document refers to a protein coding nucleic acid.

Gene product or expression product: A gene product or expression product is, in general, an RNA transcribed from a gene or polynucleotide, or a polypeptide encoded by an RNA transcribed from the gene or polynucleotide. Expression of a gene or a polynucleotide refers to (i) transcription of RNA from the gene or polynucleotide; (ii) translation of RNA transcribed from the gene or polynucleotide, or both (i) and (ii). Other steps such as processing, translocation, etc., may also take place in the course of expression or thereafter.

Isolated: As used herein, the term "isolated" refers to a compound or entity that is 1) separated from at least some of the components with which it is normally associated (e.g., purified); 2) synthesized in vitro; and/or 3) produced or prepared by a process that involves the hand of man.

Naturally: The term "naturally" or "naturally-occurring", as used herein, refers to processes, events, or things that occur in their relevant form in nature. By contrast, "not-naturally-occurring", "artificial", or "synthetic" refers to processes, events, or things whose existence or form involves the hand of man.

Operably linked: As used herein, operably linked refers to a relationship between two nucleic acids or two polypeptides wherein the expression of one of the nucleic acids or polypeptides is controlled by, regulated by, modulated by, etc., the other nucleic acid or polypeptide. For example, the transcription of a nucleic acid sequence is directed by an operably linked promoter sequence; post-transcriptional processing of a nucleic acid is directed by an operably linked processing sequence; the translation of a nucleic acid sequence is directed by an operably linked translational regulatory sequence; the transport or localization of a nucleic acid or polypeptide is directed by an operably linked transport or localization sequence; and the post-translational processing of a polypeptide is directed by an operably linked processing sequence. Preferably a nucleic acid or polypeptide sequence that is operably linked to a second nucleic acid or polypeptide sequence is covalently linked, either directly or indirectly, to such a sequence, although any effective three-dimensional association is acceptable. It is noted that a single nucleic acid or polypeptide sequence can be operably linked to multiple other sequences. For example, a single promoter can direct transcription of multiple RNA species.

Percent (%) identity: In reference to polynucleotides, "percent (%) identity" is defined as the percentage of nucleotide residues in a polynucleotide sequence that are identical with the nucleotide residues in the specific nucleic acid sequence with which comparison is being made, after aligning the sequences and introducing gaps, as needed, to achieve the maximum percent sequence identity. In reference to polypeptides, "percent (%) identity" is defined as the percentage of amino acid residues in a polypeptide sequence that are identical with the amino acid residues in the specific polypeptide sequence with which comparison is being made, after aligning the sequences and introducing gaps, as needed, to achieve the maximum percent sequence identity.

Alignment can be performed in various ways known to those of skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. US Publication No. 20030211568 describes a number of suitable methods.

Polynucleotide of interest: As used herein, the term "polynucleotide of interest" refers to any target nucleic acid sequence to be expressed in plant cells, as described herein. In many embodiments, the polynucleotide of interest will be a protein-coding polynucleotide (in which case the encoded polypeptide may be referred to as a polypeptide or protein of interest) but may also be a sequence that provides a template for transcription of a structural RNA or an active RNA such as a ribozyme, interfering RNA strand, etc. Often, the polynucleotide will be a gene that is not expressed in nature in the relevant type of plant cell, or is not expressed at the level that the polynucleotide is expressed when expression is achieved by intervention of the hand of man, as described herein. In certain embodiments of the invention, the polynucleotide comprises gene sequences that are not naturally found in the relevant plant cell at all; often including gene sequences that are naturally found in other cell types or organisms. Alternatively or additionally, a polynucleotide of interest is one that is not naturally associated with the vector sequences with which it is associated according to the present invention. The word polynucleotide is used interchangeably with "nucleic acid" or "nucleic acid molecule" herein.

Purified: As used herein, "purified" means separated from one or more compounds or entities, e.g., one or more compounds or entities with which it is naturally found. A compound or entity may be partially purified, substantially purified, or pure, where it is pure when it is removed from substantially all other compounds or entities, i.e., is preferably at least about 90%, more preferably at least about 91%, 92%, 93%, 94%, 95%, 96%, 97%, 98%, 99%, or greater than 99% pure. In the context of a preparation of a nucleic acid molecule, a preparation may be considered substantially pure if the nucleic acid represents at least 50% of all nucleic acid molecules in the preparation, preferably at least 75%, yet more preferably at least 90%, or greater, as listed above, on a molecule per molecule basis, a w/w basis, or both. In the context of a preparation of a polypeptide, a preparation may be considered substantially pure if the polypeptide represents at least 50% of all polypeptides in the preparation, preferably at least 75%, yet more preferably at least 90%, or greater, as listed above, on a molecule per molecule basis, a w/w basis, or both. A partially or substantially purified nucleic acid or polypeptide may be removed from at least 50%, at least 60%, at least 70%, or at least 80%, at least 90%, etc., of the material with which it is naturally found, e.g., cellular material such as other cellular proteins and/or nucleic acids.

Recombinant: A "recombinant" molecule refers to a molecule that has been altered by the hand of man or that is derived from (e.g., copied from) such a molecule. A recombinant polynucleotide typically contains sequences that are not found joined together in nature and/or that differ from a naturally occurring sequence. An amplified or assembled recombinant polynucleotide may be included in a suitable vector, and the vector can be used to transform a suitable cell, which may be referred to as a "recombinant cell". The nucleotide may then be expressed in the recombinant cell to produce, e.g., a "recombinant polypeptide". A recombinant polynucleotide may serve a non-coding function (e.g., promoter, origin of replication, ribosome-binding site, etc.) as well. A recombinant nucleic acid, e.g., a recombinant viral nucleic acid may be a viral nucleic acid in which one or more sequences present in the naturally occurring form has been deleted or replaced by a different sequence or into which a non-native sequence has been inserted. A "recombinant polypeptide" typically contains sequences that are not found joined together in nature and/or that differ from a naturally occurring sequence. One example of a recombinant polypeptide is a fusion protein, e.g., a protein containing two or more different proteins or peptides (which may be natural or synthetic and may be portions of a naturally occurring or synthetic polypeptide). A recombinant polynucleotide that encodes a fusion protein may be created by removing the stop codon from the polynucleotide that encodes the first protein or peptide and appending a polynucleotide that encodes the second protein or peptide in frame, so that the resulting recombinant polynucleotide encodes a single recombinant polypeptide comprising the two proteins or peptides.

The term "regulatory element" or "regulatory sequence" in reference to a nucleic acid is generally used herein to describe a portion of nucleic acid that directs or increases one or more steps in the expression (particularly transcription, but in some cases other events such as splicing or other processing) of nucleic acid sequence(s) with which it is operatively linked. The term includes promoters and can also refer to enhancers and other transcriptional control elements. Promoters are regions of nucleic acid that include a site to which RNA polymerase binds before initiating transcription and that are typically necessary for even basal levels of transcription to occur. Generally such elements comprise a TATA box. Enhancers are regions of nucleic acid that encompass binding sites for protein(s) that elevate transcriptional activity of a nearby or distantly located promoter, typically above some basal level of expression that would exist in the absence of the enhancer. In some embodiments of the invention, regulatory sequences may direct constitutive expression of a nucleotide sequence (e.g., expression in most or all cell types under typical physiological conditions in culture or in an organism); in other embodiments, regulatory sequences may direct cell or tissue-specific and/or inducible expression. For example, expression may be induced by the presence or addition of an inducing agent such as a hormone or other small molecule, by an increase in temperature, etc. Regulatory elements may also inhibit or decrease expression of an operatively linked nucleic acid.

In general, the level of expression may be determined using standard techniques for measuring mRNA or protein. Such methods include Northern blotting, in situ hybridization, RT-PCR, sequencing, immunological methods such as immunoblotting, immunodetection, or fluorescence detection following staining with fluorescently labeled antibodies, oligonucleotide or cDNA microarray or membrane array, protein array analysis, mass spectrometry, etc. A convenient way to determine expression level is to place a nucleic acid that encodes a readily detectable marker (e.g., a fluorescent or luminescent protein such as green fluorescent protein or luciferase, an enzyme such as alkaline phosphatase, etc.) in operable association with the regulatory element in an expression vector, introduce the vector into a cell type of interest or into an organism, maintain the cell or organism for a period of time, and then measure expression of the readily detectable marker, taking advantage of whatever property renders it readily detectable (e.g., fluorescence, luminescence, alteration of optical property of a substrate, etc.). Comparing expression in the absence and presence of the regulatory element indicates the degree to which the regulatory element affects expression of an operatively linked sequence.

Self-replicate: As used herein, "self-replicate" refers to the ability of a vector to copy itself inside a host cell. A vector that can "self-replicate" carries sufficient information in its own genetic elements that it does not rely on other genetic elements (e.g., those utilized by the host cell to replicate its own genome) for its replication. In general, a vector that can self-replicate is one that includes at least one replicase gene such as an RNA polymerase and possibly additional replicase genes such as a helicase, methyltransferase, etc. In certain instances additional sequences, present in cis (i.e., as part of the vector sequence) are required or can facilitate self-replication. It will be understood that a self-replicating vector will typically utilize host cell components such as nucleotides, amino acids, etc., and may be dependent on certain functions and/or enzymes of the host cell that supply such components.

Vector: "Vector" refers to a nucleic acid molecule capable of transporting another nucleic acid to which it has been linked and can include a plasmid, cosmid or viral vector. The vector may be capable of autonomous replication. Alternatively or additionally, a vector may provide one or more components necessary or sufficient for self-replication, or for replication or integration of another piece of nucleic acid. Vectors are typically nucleic acids, and may comprise DNA and/or RNA. Preferred vectors are maintained extrachromosomally.

Viral nucleic acid: The term "viral nucleic acid" refers to the genome of a virus, or a portion thereof (or, in the case of viruses whose genome comprises multiple segments, any of the segments or a portion of such a segment). The term encompasses both RNA and DNA forms of such nucleic acids and molecules having complementary sequences. DNA molecules identical to or complementary to viral RNA nucleic acids are considered viral nucleic acids, and RNA molecules identical to or complementary to viral DNA nucleic acids are considered viral nucleic acids, it being understood that DNA and RNA will contain T and U, respectively, at corresponding positions.

A viral nucleic acid may include one or more portions of non-viral origin (e.g., part or all of a naturally occurring gene, an entirely artificial sequence, or a combination of naturally occurring and artificial sequences) and may include portion(s) from multiple different virus types.

Viral replicon: The term "viral replicon" refers to a nucleic acid molecule comprising a portion or portions (cis sequences) sufficient for replication of the nucleic acid by viral replicase genes. Typically such sequences include a recognition site for a viral polymerase, e.g., a viral RNA polymerase in the case of viral replicons based on RNA viruses.

Detailed Description of Certain Embodiments of the Invention

I. Clonal Plant and Plant Tissue Expression Systems

As noted above, the present invention provides systems for expressing a polynucleotide or polynucleotides of interest in clonal root lines, clonal root cell lines, clonal plant cell lines (e.g., cell lines derived from leaf, stem, etc.), and in clonal plants. The polynucleotide of interest is introduced into an ancestral plant cell using a plant viral vector whose genome includes the polynucleotide of interest operably linked to (i.e., under control of) a promoter. A clonal root line or clonal plant cell line is established from the cell containing the virus according to any of several techniques further described below. The plant virus vector or portions thereof can be introduced into the plant cell by infection, by inoculation with a viral transcript or infectious cDNA clone, by electroporation, by T-DNA mediated gene transfer, etc.

The following sections describe plant viruses, plant viral vector, and methods for creating plant viral vectors for use in the present invention. The inventive methods for generating clonal root lines, clonal root cell lines, clonal plant cell lines, and clonal plants that express a polynucleotide of interest are then described. A "root line" is distinguished from a "root cell line" in that a root line produces actual rootlike structures or roots while a root cell line consists of root cells that do not form rootlike structures. The use of the term "line" is intended to indicate that cells of the line can proliferate and pass genetic information on to progeny cells. Cells of a cell line typically proliferate in culture without being part of an organized structure such as those found in an intact plant. The use of the term "root line" is intended to indicate that cells in the root structure can proliferate without being part of a complete plant. It is noted that the term "plant cell" encompasses root cells. However, to distinguish the inventive methods for generating root lines and root cell lines from those used to directly generate plant cell lines from non-root tissue (as opposed to generating clonal plant cell lines from clonal root lines or clonal plants derived from clonal root lines), the terms "plant cell" and "plant cell line" as used herein generally refer to cells and cell lines that consist of non-root plant tissue. The plant cells can be, for example, leaf, stem, shoot, flower part, etc. It is noted that seeds can be derived from the clonal plants generated as derived herein. Such seeds will also contain the viral vector as will plants obtained from such seeds. Methods for obtaining seed stocks are well known in the art. See, e.g., U.S. Ser. No. 10/294,314.

A. Plant Viruses and Plant Viral Vectors

Figure 17:
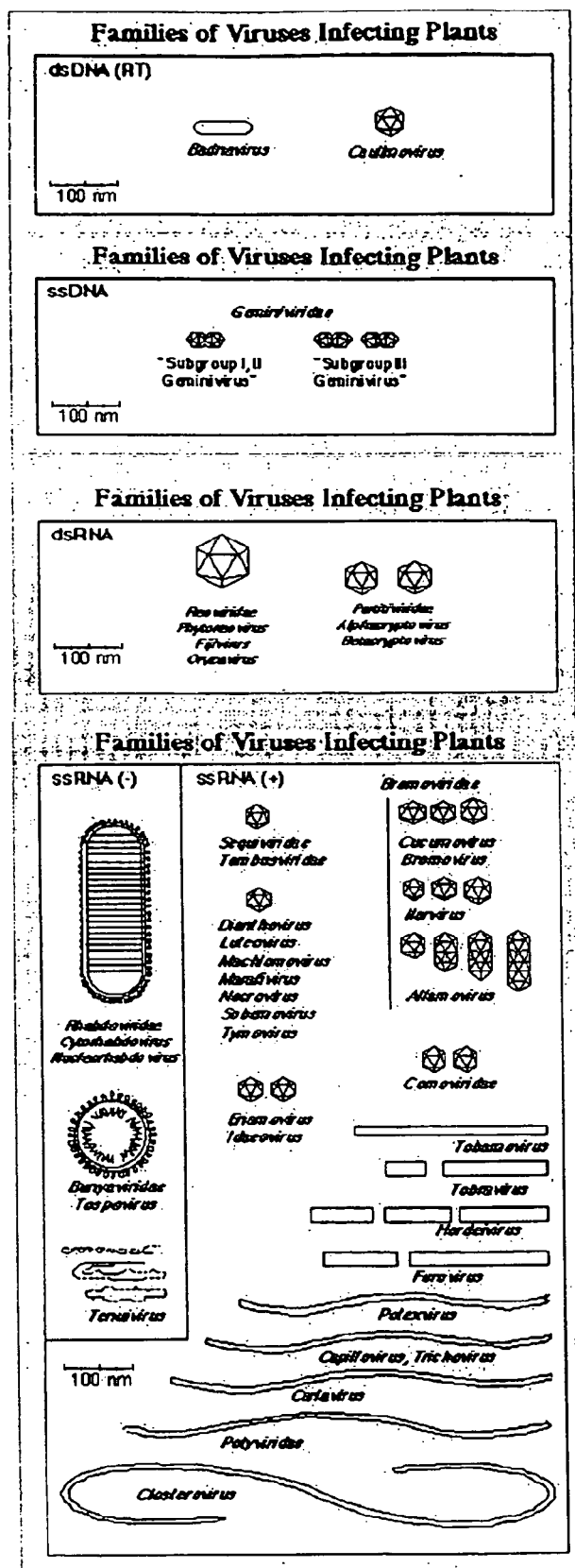
FIG. 17 presents a schematic representation of certain families of viruses that infect plants.

A wide variety of viruses are known that infect various plant species, and can be employed for polynucleotide expression according to the present invention. FIG. 17 presents a schematic representation of certain families of viruses that infect plants. Appendix A provides a representative list of plant virus families, based on the type of nucleic acid (e.g., dsDNA, ssDNA, ssRNA, dsRNA, or unassigned) that makes up the viral genome. Additional information can be found, for example, in *The Classification and Nomenclature of Viruses*", Sixth Report of the International Committee on Taxonomy of Viruses" (Ed. Murphy et al.), Springer Verlag: New York, 1995, the entire contents of which are incorporated herein by reference (see also, Grierson et al., *Plant Molecular Biology*, Blackie, London, pp. 126-146, 1984; Gluzman et al., *Communications in Molecular Biology: Viral Vectors*, Cold Spring Harbor Laboratory, NY, pp. 172-189, 1988; Mathew, *Plant Viruses Online*.

In nature, in order to enter and infect a plant cell, plant viruses need to cross the cell wall, in addition to protective layers of waxes and pectins. Most or all plant viruses are thought to rely on mechanical breach of the cell wall, rather than on cell-wall-surface receptors, to enter a cell. Such a breach can be caused, for example, by physical damage to the cell, by an organism such as a bacterium, a fungus, a nematode, an insect, or a mite that can deliver the virus. In the laboratory, viruses are typically administered to plant cells simply by rubbing the virus on the plant.

Some plant viruses have segmented genomes, in which two or more physically separate pieces of nucleic acid together make up the plant genome. For example, many RNA plant virus genomes can be classified as mono-, bi-, or tri-partite, i.e., they may consist of 1, 2, or 3 nucleic acids respectively. In some cases, these separate pieces are packaged together in the same viral capsid; in others (i.e., those with multipartite genomes), each genome segment is packaged into its own viral particle. Infection can typically be accomplished by delivery either of plant viral nucleic acid (e.g., RNA) or capsid containing such nucleic acid.

Once the virus has entered (infected) a cell, it typically replicates within the infected cell and then spreads locally (i.e., from cell to cell within leaves that were infected initially). Following local spread, the virus may move into uninfected leaves, e.g., upper leaves of the plant, which is referred to as systemic infection or systemic spread. In general, cell-to-cell spread of many plant viruses requires a functional movement protein (which allows movement of viral transcripts) while systemic spread requires a functional coat protein (and, generally, also a functional movement protein), which allows the formation of viral particles.

In addition to functional movement and coat protein encoding components, the viral genome may contain additional components that are required for local (e.g., cell-to-cell) or long distance (e.g., systemic) spread or facilitate such spread. These cis-acting components may be either coding or non-coding components. For example, they may correspond to portions of a 3' untranslated region (UTR, also referred to as NTR) of a viral transcript (i.e., they may provide a template for transcription of a 3' untranslated region of a viral transcript). Thus important viral components can be either coding or noncoding regions of a viral genome and include a variety of regulatory regions. Such regions may function in replication and/or processing or expression of mRNA. By "functional protein encoding component" is meant a polynucleotide comprising a coding portion that encodes a functionally active protein, operably linked to sufficient regulatory elements such as a promoter, so that expression is achieved.

In order to successfully establish either a local (intraleaf) or systemic infection a virus must be able to replicate. Many viruses contain genes encoding one or more proteins that participate in the replication process (referred to herein as replication proteins or replicase proteins). For example, many RNA plant viruses encode an RNA polymerase. Additional proteins may also be required, e.g., helicase or methyltransferase protein(s). The viral genome or segment may contain various sequence components, e.g., cis-acting sequences, in addition to functional genes encoding replication proteins, which are also required for or facilitate replication. Viral genomes or segments may also contain cis-acting sequences that contribute to high levels of transcript and/or expression. It is noted that nucleic acids encoding various viral proteins, e.g., replicase proteins, movement protein, coat protein, may be present within different viral nucleic acid molecules, which may complement each other in trans. (See, e.g., WO 00/25574 and U.S. National application Ser. No. 10/770,600, entitled "SYSTEM FOR EXPRESSION OF GENES IN PLANTS", filed Feb. 3, 2004, now U.S. Pat. No. 7,491,509.

Thus in certain embodiments of the invention rather than delivering a single viral vector to a plant cell, multiple different vectors are delivered which, together, allow for replication (and, optionally cell-to-cell and/or long distance movement) of the viral vector(s). Some or all of the proteins may be encoded by the genome of transgenic plants.

Viral vectors based on any virus that infects plants may be used to generate a clonal root line, clonal plant cell line or clonal plant that expresses a polynucleotide of interest in accordance with the present invention. Particularly preferred viruses are ssRNA viruses, most desirably with a (+)-stranded genome. Techniques and reagents for manipulating the genetic material present in such viruses are well known in the art. Typically, for example, a DNA copy of the viral genome is prepared and cloned into a microbial vector, particularly a bacterial vector. Certain ssDNA viruses, including particularly geminiviruses, may also be used. It will be appreciated that in general plant viral vectors and viral nucleic acids such as viral genomes may exist in RNA or DNA form. In addition, where reference is made to a feature such as a genome or portion thereof of an RNA virus, which is present within a DNA vector, it is to be understood that the feature is present as the DNA copy of the RNA form.

Preferred vectors are based on viruses such as members of the Bromoviridae (e.g., bromoviruses, alfamoviruses, ilarviruses) and Tobamoviridae. Certain preferred virus species include, for example, Alfalfa Mosaic Virus (AlMV), Apple Chlorotic Leaf Spot Virus, Apple Stem Grooving Virus, Barley Stripe Mosiac Virus, Barley Yellow Dwarf Virus, Beet Yellow Virus, Broad Bean Mottle Virus, Broad Bean Wilt Virus, Brome Mosaic Virus (BMV), Carnation Latent Virus, Carnation Mottle Virus, Carnation Ringspot Virus, Carrot Mottle Virus, Cassaya Latent Virus (CLV), Cowpea Chlorotic Mottle Virus, Cowpea Mosaic Virus (CPMV), Cucumber Green Mottle Mosaic Virus, Cucumber Mosaic Virus, Lettuce Infectious Yellow Virus, Maize Chlorotic Mottle Virus, Maize Rayado Fino Virus, Maize Streak Virus (MSV), Parsnip Yellow Fleck Virus, Pea Enation Mosaic Virus, Potato Virus X, Potato Virus Y, Raspberry Bushy Dwarf Virus, Rice Necrosis Virus (RNV), Rice Stripe Virus, Rice Tungro Spherical Virus, Ryegrass Mosaic Virus, Soil-borne Wheat Mosaic Virus, Southern Bean Mosaic Virus, Tobacco Etch Virus (TEV), Tobacco Mosaic Virus (TMV), Tobacco Necrosis Virus, Tobacco Rattle Virus, Tobacco Ring Spot Virus, Tomato Bushy Stunt Virus, Tomato Golden Mosaic Virus (TGMV), and Turnip Yellow Mosaic Virus (TYMV).

Figure 18:
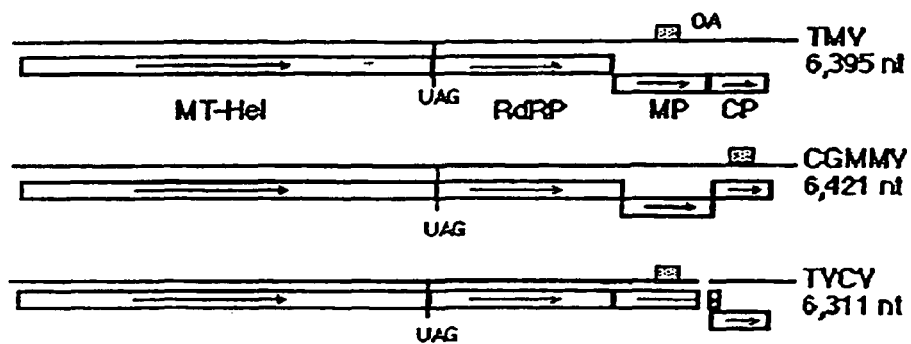
FIG. 18 shows representative examples of tobamovirus genomes.

In certain embodiments of the invention a TMV-based viral vector (viral nucleic acid) is used. TMV is the type member of the tobamovirus group. Tobamoviruses have single-(+)-stranded RNA genomes, and produce rod-shaped virions consisting of the RNA genome and coat protein (CP) polypeptides. Tobamovirus genomes encode 4-5 polypeptides. Two of the polypeptides are translated from the same 5'-proximal initiation codon and function in viral replication. These polypeptides include an RNA-dependent RNA polymerase. In addition, polypeptides having methyltransferase and RNA helicase activity are typically encoded. The other encoded proteins typically include a movement protein and the coat protein, each of which is translated from a separate subgenomic RNA. Representative examples of tobamovirus genomes are depicted in FIG. 18. Tobamoviruses other than TMV can be used in various embodiments of the invention.

The TMV genome is 6395 nucleotides long and is encapsidated with a 17.5 kD CP, which produces 300 nm-long rods. In addition to CP, TMV has three nonstructural proteins: 183 and 126 kD proteins are translated from genomic RNA and are required for viral replication. The 30 kD movement protein provides for the transfer of viral RNA from cell-to-cell. Plant species susceptible to infection with TMV include *Beta vulgaris, Capsicum frutescens, Chenopodium amaranticolor, Chenopodium hybridum, Chenopodium quinoa, Cucumis melo, Cucumis sativus, Cucurbita pepo, Datura stramonium, Lactuca sativa, Lucopersicon esculentum, Lycopersicon pimpinellifolium, Nicotiana benthamiana, Nicotiana bigelovii, Nicotiana clevelandii, Nicotiana debneyi, Nicotiana glutinosa, Nicotiana rustica, Nicotiana sylvestris, Nicotiana tabacum, Papaver nudicaule, Phaseolus vulgaris, Physalis floridana, Physalis peruviana*, and *Solanum tuberosum*.

In various other embodiments of the invention an AlMV-based viral vector (viral nucleic acid) is used. AlMV is an Alfamovirus, closely related to the Ilarvirus group and is a member of the Bromoviridae family. The genome of AlMV consists of three positive-sense RNAs (RNAs 1-3). RNAs 1 and 2 encode replicase proteins P1 and P2, respectively; RNA3 encodes the cell-to-cell movement protein P3. A subgenomic RNA, RNA4, is synthesized from RNA3. This subgenomic RNA4 encodes the viral coat protein (CP). CP participates in viral genome activation to initiate infection, RNA replication, viral assembly, viral RNA stability, long-distance movement of viral RNA, and symptom formation. AlMV depends on a functional P3 protein for cell-to-cell movement, and requires the CP protein throughout infection. Depending on the size of the CP-encapsidated viral RNA, virions of AlMV can vary significantly in size (e.g., 30- to 60-nm in length and 18 nm in diameter) and form (e.g., spherical, ellipsoidal, or bacilliform).

The host range of AlMV is remarkably wide and includes the agriculturally valuable crops alfalfa (*Medicago sativa*), tomato (*Lycopersicon esculentum*), lettuce (*Lactuca sativa*), common bean (*Phaseolus vulgaris*), potato (*Solanum tuberosum*), white clover (*Trifolium repens*) and soybean (*Glycine max*). Particular susceptible host species include, for example, *Abelmoschus esculentus, Ageratum conyzoides, Amaranthus caudatus, Amaranthus retroflexus, Antirrhinum majus, Apium graveolens, Apium graveolens* var. *rapaceum, Arachis hypogaea, Astragalus glycyphyllos, Beta vulgaris, Brassica campestris* ssp. *rapa, Calendula officinalis, Capsicum annuum, Capsicum frutescens, Caryopteris incana, Catharanthus roseus, Celosia argentea, Cheiranthus cheiri, Chenopodium album, Chenopodium amaranticolor, Chenopodium murale, Chenopodium quinoa, Cicer arietinum, Cichorium endiva, Coriandrum sativum, Crotalaria spectabilis, Cucumis melo, Cucumis sativus, Cucurbita pepo, Cyamopsis tetragonoloba, Daucus carota* (var. *sativa*), *Dianthus barbatus, Dianthus caryophyllus, Emilia sagittata, Fagopyrum esculentum, Gomphrena globosa, Helianthus annuus, Lablab purpureus, Lathyrus odoratus, Lens culinaris, Linum usitatissimum, Lupinus albus, Macroptilium lathyroides, Malva parviflora, Matthiola incana, Medicago hispida, Melilotus albus, Nicotiana bigelovii, Nicotiana clevelandii, Nicotiana debneyi, Nicotiana glutinosa, Nicotiana megalosiphon, Nicotiana rustica, Nicotiana sylvestris, Nicotiana tabacum, Ocimum basilicum, Petuniaxhybrida, Phaseolus lunatus, Philadelphus, Physalisfloridana, Physalis peruviana, Phytolacca americana, Pisum sativum, Solanum demissum, Solanum melongena, Solanum nigrum, Solanum nodiflorum, Solanum rostratum, Sonchus oleraceus, Spinacia oleracea, Stellaria media, Tetragonia tetragonioides, Trifolium dubium, Trifolium hybridum, Trifolium incarnatum, Trifolium pratense, Trifolium subterraneum, Tropaeolum majus, Viburnum opulus, Vicia faba, Vigna radiata, Vigna unguiculata, Vigna unguiculata* ssp. *sesquipedalis*, and *Zinnia elegans*. While AlMV is a preferred viral vector, other alfamoviruses can also be used in various embodiments of the invention. Related viruses, such as ilarviruses can also be used.

B. Creation of Plant Viral Expression Vectors

Elements of these plant viruses are genetically engineered according to known techniques (see, for example, (see, for example, Sambrook et al., *Molecular Cloning*, 2nd Edition, Cold Spring Harbor Press, NY, 1989; Clover et al., *Molecular Cloning*, IRL Press, Oxford, 1985; Dason et al., *Virology*, 172:285-292, 1989; Takamatsu et al., *EMBO J.* 6:307-311, 1987; French et al., *Science* 231: 1294-1297, 1986; Takamatsu et al., *FEBS Lett.* 269:73-76, 1990; Yusibov and Loesch-Fries, Virology, 208(1): 405-7, 1995. Spitsin et al., Proc Natl Acad Sci USA, 96(5): 2549-53, 1999, etc.) to generate viral vectors for use in accordance with the present invention. In general, a viral vector is a viral nucleic acid. Typically the viral vector is the genome, or a majority thereof (i.e., at least 50% of the genome), of a virus, or a nucleic acid molecule complementary in base sequence to such a nucleic acid molecule. In the case of segmented viruses, the viral vector may be a genome segment, or a majority thereof. The viral vector may be in RNA or DNA form.

Preferably the viral vector comprises a portion sufficient to support replication of the viral vector in the presence of the appropriate viral replicase proteins, i.e., constitutes a viral replicon. The ability of any particular portion of a viral genome to support replication of a nucleic acid that includes the portion, in the presence of viral replicase proteins, can readily be tested using methods known in the art, e.g., by making deletion mutants, by transferring the portion into a nucleic acid that does not support replication and determining whether replication occurs, etc. The replicase proteins may be encoded by the vector, by another vector, or by a plant into which the vector is introduced. In certain preferred embodiments of the invention the vector is capable of self-replication, i.e., it encodes the necessary viral proteins for replication of the virus within an appropriate plant host. In certain embodiments of the invention the vector comprises a MP gene. In certain embodiments of the invention the vector comprises a CP gene. However, in certain embodiments of the invention neither an MP gene nor a CP gene is present in the vector. Since the clonal root lines, clonal plant lines, and clonal plants are derived from single ancestral cells into which the vector has been introduced, it is not necessary for the viral vector to have cell-to-cell or long distance movement capability. In particular, clonal plants can express the polynucleotide of interest throughout the plant even though the viral transcript does not move, since each cell is derived from a single ancestral cell that contains the viral vector.

In general, a polynucleotide of interest is inserted into a viral vector under control of (i.e., operably linked to), a promoter that directs transcription of the polynucleotide in a plant cell of interest. In certain preferred embodiments of the invention a plant viral promoter is used, e.g., a promoter for coat protein, movement protein, etc. The polynucleotide of interest may be inserted in place of the endogenous MP or CP coding sequence. For example, as described in more detail in the Examples, a TMV-based vector in which the TMV CP coding sequence has been replaced by a polynucleotide of interest, under control of the TMV CP promoter can be used. Alternately, the inserted polynucleotide may include its own promoter, which may be identical or similar to one of the naturally occurring viral promoters, may be from a different virus (e.g., the cauliflower mosaic virus), may be a non-viral promoter such as a promoter for a plant gene, or a synthetic promoter. In certain embodiments of the invention an inducible promoter is used. A variety of inducible promoters are known that function in plants. See, e.g., Zuo, J. and Chua, N-H., "Chemical-inducible systems for regulated expression of plant genes", *Curr. Op. in Biotechnol.*, 11:146-51, 2000. For example, promoters inducible by metals such as copper, or responsive to hormones such as estrogen, or systems responsive to other small molecules such as tetracycline can be used. Other stimuli such as heat, light, etc., can be used. See U.S. Ser. No. 10/294,314.

In certain embodiments of the invention in any of its aspects, trans-activation is used to induce or increase expression of a polynucleotide of interest. For example, the expression cassette comprising the polynucleotide can be an inactive expression cassette that comprises an inactive or silenced foreign nucleic acid sequence, which is capable of directing expression of a polynucleotide of interest upon its activation. In certain embodiments of the invention trans-activation is accomplished by introducing a factor for activating or facilitating the expression of an inactive or silenced polynucleotide sequence into cells of the clonal entity. A promoter that can be activated in trans in such a manner is referred to as being "trans-activatable". See U.S. Ser. No. 10/832,603, entitled "Expression of Foreign Sequences in Plants Using Trans-Activation System", which is incorporated herein by reference, for further details of certain suitable methods. Such methods include techniques based on recombination (e.g., using a Lox/Cre or Flp/Frt recombinase system) and techniques based on proteins comprising a DNA binding domain such as GAL4 and a transcriptional activation domain such as VP16. A variety of other methods may be used for achieving trans-activation.

In certain embodiments of the invention the polynucleotide is inserted to create an independent open reading frame, while in other embodiments of the invention the polynucleotide is inserted to create an open reading frame in which a polynucleotide lacking a stop codon is inserted in frame with sequences encoding part or all of a viral protein such as CP, so that a fusion protein is produced upon translation. Multiple polynucleotides can be inserted. In certain preferred embodiments of the invention the TMV vector retains part or all of its 3' UTR and/or all or part of the CP coding sequence. In certain embodiments of the invention the polynucleotide of interest or a viral vector into which the polynucleotide of interest is inserted comprises a portion encoding a targeting sequence, e.g., a sequence that targets an encoded polypeptide to a particular intracellular organelle or compartment. For example, it may be desirable to target a polypeptide of interest to the endoplasmic reticulum, which may ultimately result in secretion of the polypeptide. The secreted polypeptide can then be harvested from culture medium or from interstitial fluid of a plant tissue.

FIGS. 1-5 show examples of engineering various plant virus vectors suitable for use in the present invention. FIG. 1 shows a TMV based virus construct, D4, and the same construct following insertion of a polynucleotide of interest (e.g., a gene encoding hGH, GCSF, GFP, etc., indicated as "target") whose transcription is under control of the TMV CP subgenomic promoter. Details regarding the creation of such vectors are given in Example 1.

Figure 2:
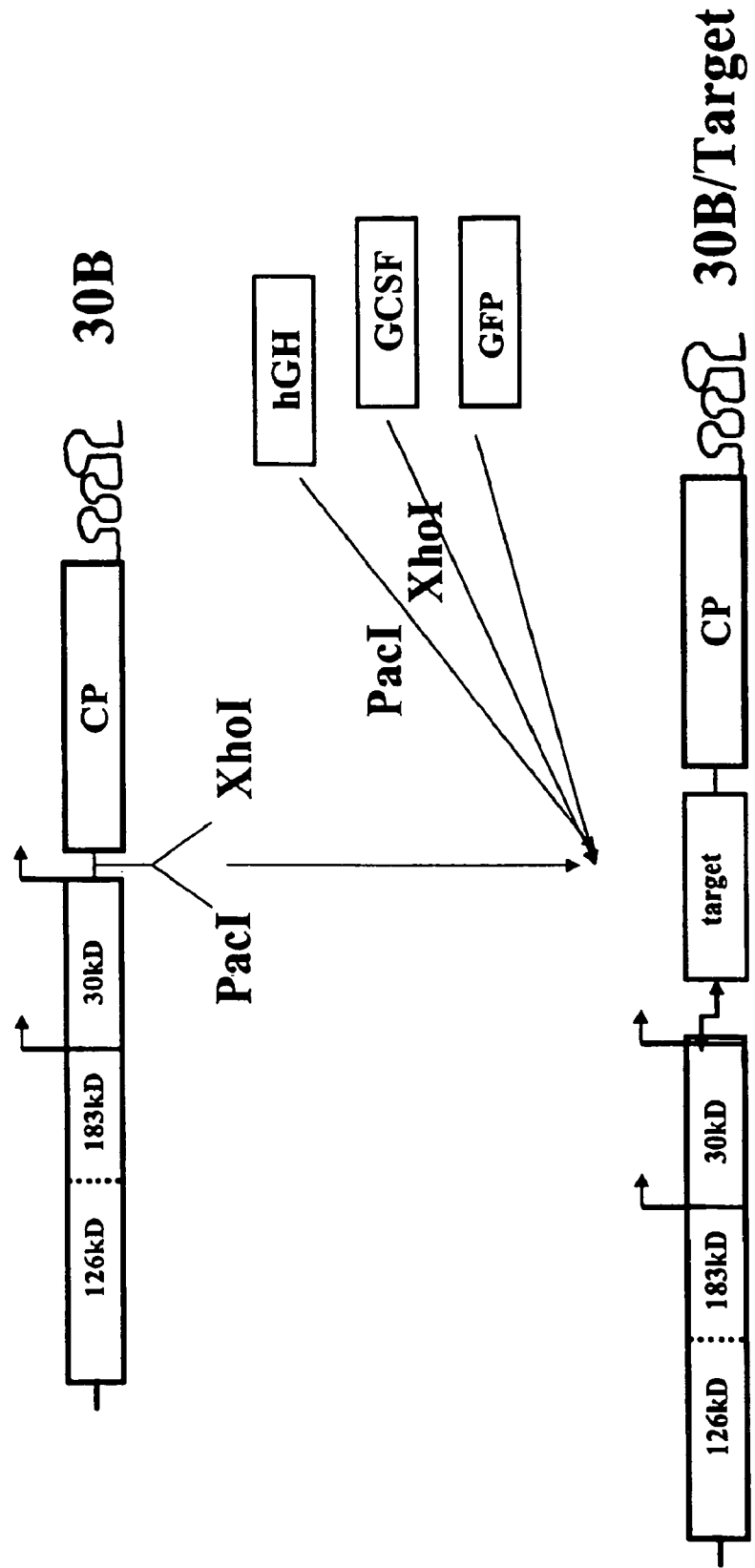
FIG. 2 presents a schematic diagram of the engineering of a TMV based viral construct containing a polynucleotide of interest. The upper portion of the figure shows a schematic diagram of the genomic organization of a TMV based virus construct, 30B. The lower portion shows the same construct following insertion of a polynucleotide of interest (e.g., a gene encoding hGH, GCSF, GFP, etc., indicated as "target"). The 126/183 kDa protein is required for replication of the virus. The 30 kD protein is the movement protein (MP) that mediates cell-to-cell movement. CP is the coat protein that mediates systemic spread. Arrows indicate positions of the subgenomic promoters. Transcription of the inserted polynucleotide is under control of an introduced promoter. CP expression is under control of the endogenous CP promoter. The 3' portion of the construct includes TMV coat protein sequences and untranslated regions. These portions are optional.

FIG. 2 presents a schematic diagram of the engineering of a TMV based viral construct containing a polynucleotide of interest. The upper portion of the figure shows the genomic organization of a TMV based virus construct, 30B (Yusibov, V., Shivprasad, S., Turpen, T. H., Dawson, W., and Koprowski, H., "Plant viral vectors based on tobamoviruses", in *Plant Biotechnology: New Products and Applications* (Eds. J. Hammond, P. McGarvey, and V. Yusibov), pp. 81-94, Springer-Verlag, 1999). The lower portion shows the same construct following insertion of a polynucleotide of interest (e.g., a gene encoding hGH, GCSF, GFP, etc., indicated as "target"). The 126/183 kDa protein is required for replication of the virus. The 30 kD protein is the movement protein (MP) that mediates cell-to-cell movement. CP is the coat protein that mediates systemic spread. Arrows indicate positions of the subgenomic promoters in certain embodiments of the invention. Transcription of the inserted polynucleotide is under control of an introduced promoter. CP expression is under control of the endogenous CP promoter in the construct shown in FIG. 2.

Similar vectors in which polynucleotide of interest is in frame with the CP coding sequence so as to encode a fusion protein can also be used. In general, polynucleotides of interest (and their encoded proteins) can be expressed as independent open reading frames (see, e.g., Pogue, G. P., Lindbo, J. A., Dawson, W. O., and Turpen, T. H. "Tobamovirus transient expression vectors: tools for plant biology and high-level expression of foreign proteins in plants", *Pl. Mol. Biol. Manual. L*4, 1-27., 1998) or as fusions with coat protein (Yusibov, V., Modelska, A., Steplewski, K., Agadjanyan, M., Weiner, D., Hooper, C. and Koprowski, H., "Antigens produced in plants by infection with chimeric plant viruses immunize against rabies virus and HIV-1", *Proc. Natl. Acad. Sci. USA* 94, 5784-5788, 1997). In the vector described in the latter, target sequences are replicated from a second subgenomic promoter. In general, transcription of a polynucleotide of interest and/or an endogenous gene such as MP or CP can be driven by endogenous promoters or inserted promoters (which may be identical to naturally occurring vectors from the same or a different virus or may be synthetic, or a combination of natural and synthetic sequences.

The 3' portion of the construct preferably includes the TMV 3' UTR, which may form stem-loop structure(s) as shown. The 3' portion of the construct may also include TMV coat protein sequences that contain a cis element that may be required for optimal replication. This sequence is optional.

Figure 3:
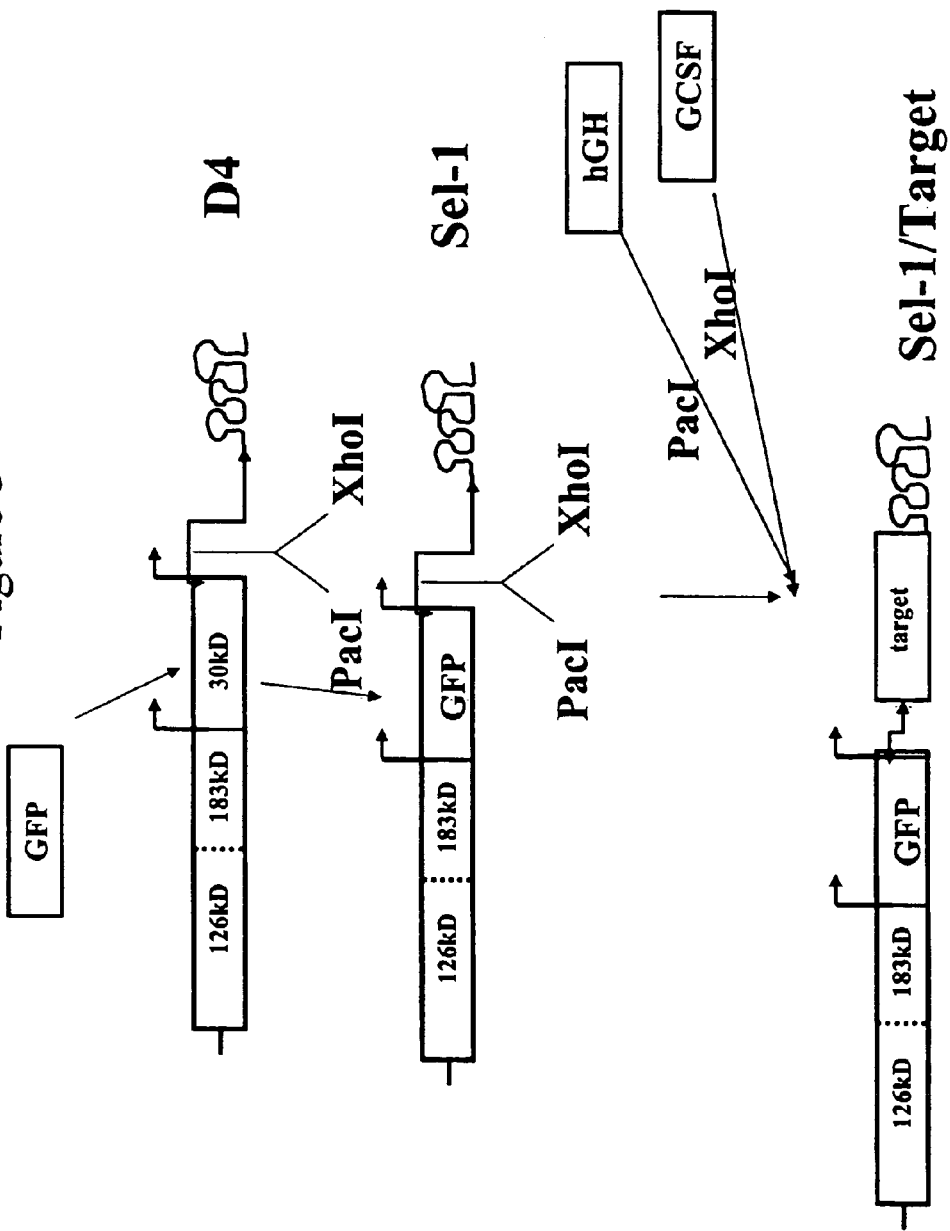
FIG. 3 presents a schematic diagram of the engineering of a TMV based viral construct containing a polynucleotide of interest and a gene encoding a marker for detection and/or selection. The upper portion of the figure shows the genomic organization of a TMV based virus construct, D4. The middle portion of the figure shows the same construct after insertion of a gene encoding a detectable marker (GFP) replacing the MP coding sequence. The lower portion of the figure shows the same construct following insertion of a polynucleotide of interest (e.g., a gene encoding hGH, GCSF, GFP, etc., indicated as "target"). The 126/183 kDa protein is required for replication of the virus. Arrows indicate positions of the subgenomic promoters. Transcription of the detectable marker is under control of the MP subgenomic promoter. Transcription of the inserted polynucleotide of interest is under control of the TMV CP subgenomic promoter. The 3' portion of the construct includes TMV coat protein sequences and untranslated regions. These portions are optional.

FIG. 3 presents a schematic diagram of the engineering of a TMV based viral construct containing a polynucleotide of interest and a gene encoding a marker, e.g., a marker that allows for detection and/or selection. The upper portion of the figure shows the genomic organization of a TMV based virus construct, D4. The middle portion of the figure shows the same construct after insertion of a gene encoding a detectable marker (GFP) replacing the MP coding sequence. The lower portion of the figure shows the same construct following insertion of a polynucleotide of interest (e.g., a gene encoding hGH, GCSF, GFP, etc., indicated as "target"). The 126/183 kDa protein is required for replication of the virus. Arrows indicate positions of the subgenomic promoters. Transcription of the detectable marker is under control of the MP subgenomic promoter. Transcription of the inserted polynucleotide of interest is under control of the TMV CP subgenomic promoter. However, other promoters could be used as described above. The 3' portion of the construct includes TMV coat protein sequences that contain a cis element that may be required for optimal replication and that may form stem-loop structure(s) as shown.

Figure 4:
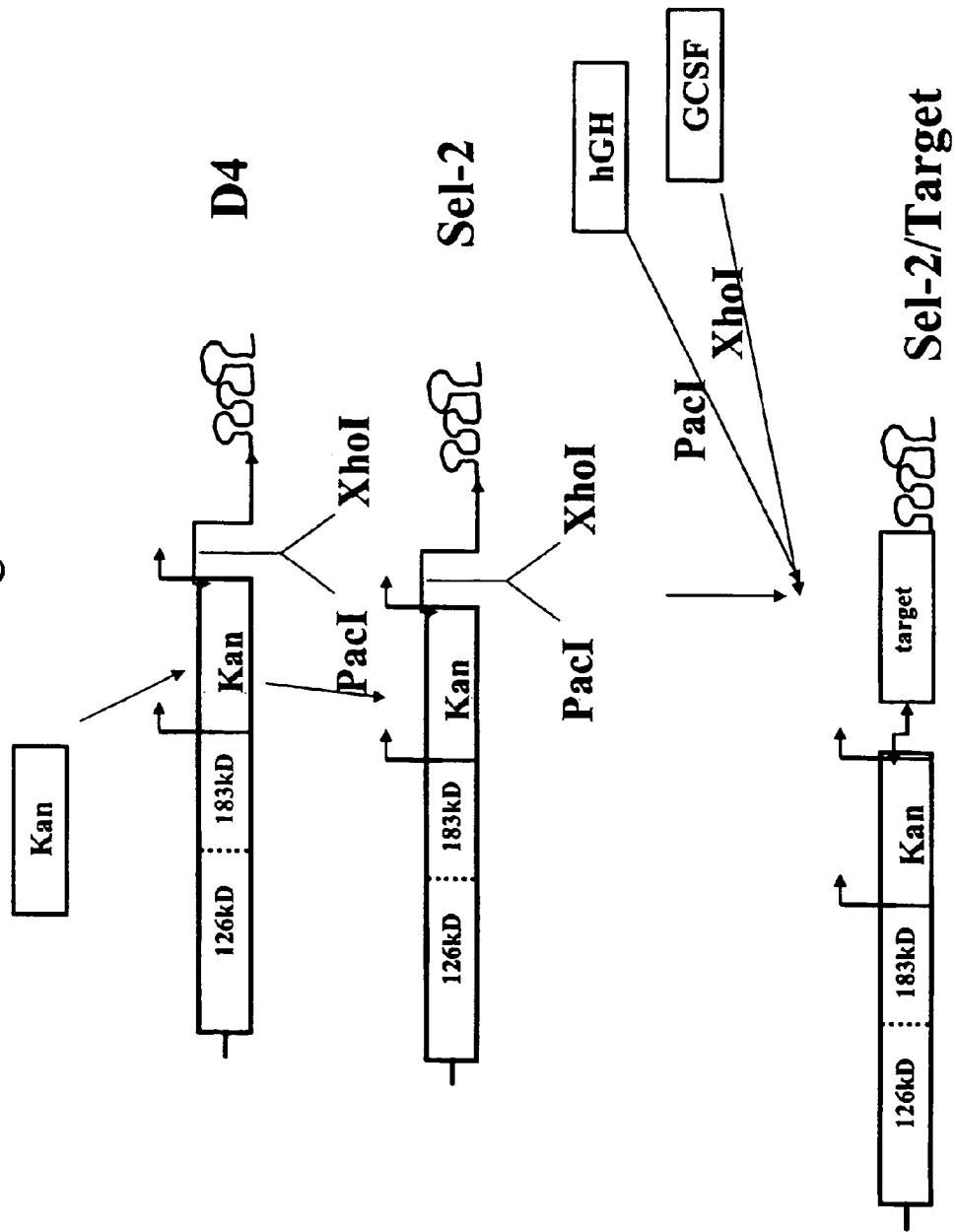
FIG. 4 presents a schematic diagram of the engineering of a TMV based viral construct containing a polynucleotide of interest and a gene encoding a marker for detection and/or selection. The upper portion of the figure shows the genomic organization of a TMV based virus construct, D4. The middle portion of the figure shows the same construct after insertion of a gene encoding a selectable marker (gene encoding resistance to kanamycin) replacing the MP coding sequence. The lower portion of the figure shows the same construct following insertion of a polynucleotide of interest (e.g., a gene encoding hGH, GCSF, GFP, etc., indicated as "target"). The 126/183 kDa protein is required for replication of the virus. Arrows indicate positions of the subgenomic promoters. Transcription of the selectable marker is under control of the TMV MP subgenomic promoter. Transcription of the inserted polynucleotide of interest is under control of the TMV CP subgenomic promoter. The 3' portion of the construct includes TMV coat protein sequences and untranslated regions. These portions are optional.

FIG. 4 shows a vector similar to that shown in FIG. 3 except that a selectable marker (a gene encoding a protein that confers resistance to kanamycin) is inserted instead of a gene encoding GFP. Including a gene that encodes a detectable or selectable marker in addition to a polynucleotide of interest is useful in the identification of clonal root lines and clonal plant cell lines that contain the vector and/or for identifying those lines that exhibit high and/or stable levels of expression.

In general, a wide variety of different markers can be used in accordance with the present invention. In general, a suitable marker for use in the invention is a detectable marker or a selectable marker. It is noted that in accordance with the practice in the art, the term "marker" can refer either to a nucleotide sequence, e.g., a gene, that encodes a product (protein) that allows for detection or selection, or can be used to refer to the protein itself. The term "selectable marker" is used herein as it is generally understood in the art and refers to a marker whose presence within a cell or organism confers a significant growth or survival advantage or disadvantage on the cell or organism under certain defined culture conditions (selective conditions). For example, the conditions may be the presence or absence of a particular compound or a particular environmental condition such as increased temperature, increased radiation, presence of a compound that is toxic in the absence of the marker, etc. The presence or absence of such compound(s) or environmental condition(s) is referred to as a "selective condition" or "selective conditions". By "growth advantage" is meant either enhanced viability (e.g., cells or organisms with the growth advantage have an increased life span, on average, relative to otherwise identical cells), increased rate of proliferation (also referred to herein as "growth rate") relative to otherwise identical cells or organisms, or both. In general, a population of cells having a growth advantage will exhibit fewer dead or nonviable cells and/or a greater rate of cell proliferation that a population of otherwise identical cells lacking the growth advantage. Although typically a selectable marker will confer a growth advantage on a cell, certain selectable markers confer a growth disadvantage on a cell, e.g., they make the cell more susceptible to the deleterious effects of certain compounds or environmental conditions than otherwise identical cells not expressing the marker.

Antibiotic resistance markers are a non-limiting example of a class of selectable marker that can be used to select cells that express the marker. In the presence of an appropriate concentration of antibiotic (selective conditions), such a marker confers a growth advantage on a cell that expresses the marker. Thus cells that express the antibiotic resistance marker are able to survive and/or proliferate in the presence of the antibiotic while cells that do not express the antibiotic resistance marker are not able to survive and/or are unable to proliferate in the presence of the antibiotic. For example, a selectable marker of this type that is commonly used in plant cells is the NPTII protein, which encodes a protein that provides resistance against the antibiotic kanamycin. Additional selectable markers include proteins that confer resistance against carbenecillin (e.g., β-lactamases), proteins that confer resistance against gentamicin, hygronycin, etc.)

A second non-limiting class of selectable markers are nutritional markers. Such markers are generally enzymes that function in a biosynthetic pathway to produce a compound that is needed for cell growth or survival. In general, under nonselective conditions the required compound is present in the environment or is produced by an alternative pathway in the cell. Under selective conditions, functioning of the biosynthetic pathway in which the marker is involved is needed to produce the compound.

In general, a detectable marker is a marker whose presence within a cell can be detected through means other than subjecting the cell to a selective condition or directly measuring the level of the marker itself. Thus in general, the expression of a detectable marker within a cell results in the production of a signal that can be detected and/or measured. The process of detection or measurement may involve the use of additional reagents and may involve processing of the cell. For example, where the detectable marker is an enzyme, detection or measurement of the marker will typically involve providing a substrate for the enzyme. Preferably the signal is a readily detectable signal such as light, fluorescence, luminescence, bioluminescence, chemiluminescence, enzymatic reaction products, stainable products, or color. Thus preferred detectable markers for use in the present invention include fluorescent proteins such as green fluorescent protein (GFP) and variants thereof. Other suitable markers include luciferase, yellow fluorescent protein (YFP), lichenase, β-galactosidase, alkaline phosphatase, etc. Preferably the detectable marker is one that can be detected in intact, living root and/or plant cells.

Figure 5:
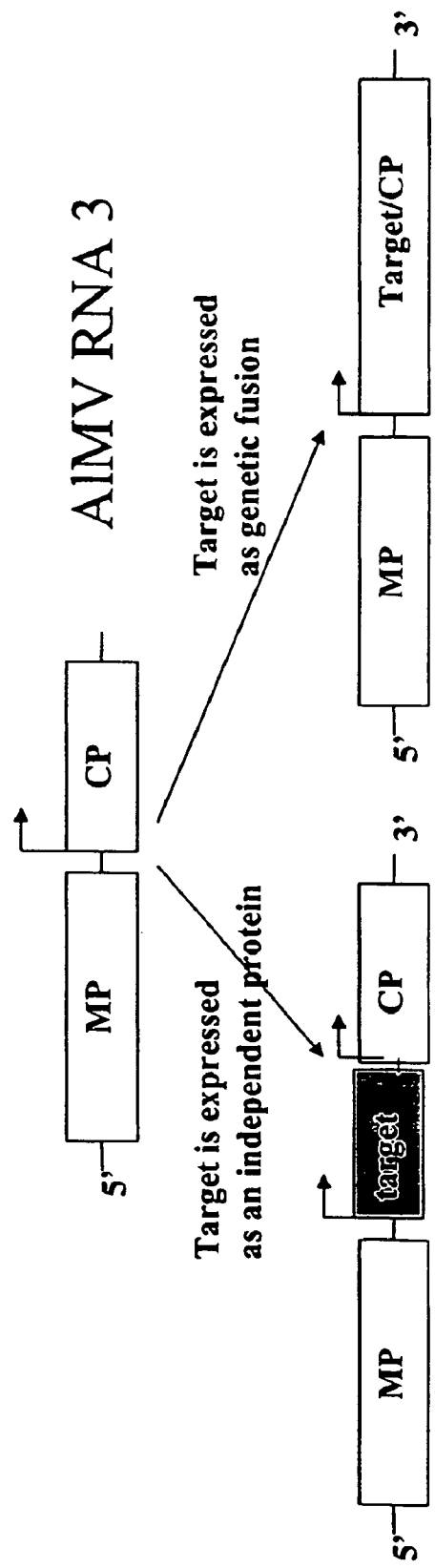
FIG. 5 presents a schematic diagram of the engineering of AlMV based viral constructs containing a polynucleotide of interest either as an independent open reading frame or as a genetic fusion with AlMV CP coding sequences. The upper portion of the figure shows the genomic organization of RNA3 of AlMV, which includes genes encoding CP and MP as well as containing 5' and 3' UTRs and a subgenomic promoter. The left side of the figure shows a construct in which transcription of an mRNA containing separate open reading frames that encode a polypeptide of interest (indicated as "target") and the AlMV CP is under control of the AlMV subgenomic promoter. The right side of the figure shows a construct in which transcription of an mRNA containing a single open reading frame containing a polynucleotide of interest and CP coding sequences is under control of the AlMV CP subgenomic promoter. The open reading frame encodes a fusion protein in which a polypeptide of interest is fused to CP.

Another example of a preferred viral vector for use in the present invention is an AlMV vector in which a polynucleotide of interest is inserted, as shown in FIG. 5. For example, the polynucleotide of interest may replace the native AlMV CP encoding component in RNA3 of AlMV. Transcription of the polynucleotide of interest may be placed under control of the AlMV CP promoter. Alternately, the polynucleotide may replace the AlMV MP encoding component, and its transcription may be placed under control of the AlMV MP promoter. In other embodiments the inserted polynucleotide does not replace endogenous viral sequences. The polynucleotide of interest may be inserted in frame with CP coding sequences (complete or partial), so that a fusion protein is produced. In certain embodiments of the invention the fusion protein comprises a cleavage site between the CP portion and the remainder, so that the fusion protein can be cleaved to yield a protein of interest free of CP sequences (or containing only a small number of such sequences). In certain embodiments of the invention the fusion protein assembles into particles, which can facilitate purification and/or antigen presentation (see, e.g., U.S. Pat. Nos. 6,042,832 and 6,448,070).

Yet another example of a vector useful in the practice of the present invention is a cauliflower mosaic virus (CMV) viral vector in which a polynucleotide of interest is inserted under control of the CMV CP promoter, replacing the CMV CP encoding component found in the genome of naturally occurring CMV.

In certain embodiments of the invention it is desirable to insert a portion of coding or noncoding sequence from a viral vector of one virus type into a viral vector of another type. For example, certain sequences may enhance replication or expression, etc. Such sequences may comprise, for example, part or all of a viral transcript 5' or 3' UTR.

Generally, in order to preserve viral function and also simply for ease of genetic manipulation, viral vectors will be prepared by altering an existing plant virus genome, for example by removing particular genes and/or by disrupting or substituting particular sequences so as to inactivate or replace them. In such circumstances, the vectors will show very high sequence identity with natural viral genomes. Of course, completely novel vectors may also be prepared, for example, by separately isolating individual desired genetic elements and linking them together, optionally with the inclusion of additional elements. It is noted that when a plant virus vector is said to affirmatively express a particular protein or activity needed for viral replication, movement, or some other viral function, it is not necessary that the relevant gene be identical to the corresponding gene found in nature. So long as the protein is functional, it may be used in accordance with the present invention. Very high sequence identity with the natural protein, however, is generally preferred. For instance, large deletions (e.g., greater than about 25 amino acids) should generally be avoided according to certain embodiments of the invention. Typically, viral proteins expressed in accordance with the present invention will show at least 50%, preferably 60%, 70%, 80%, 85%, 90%, 91%, 92%, 93%, 94%, 95%, 96%, 97%, 98%, or 99% sequence identity with the corresponding natural viral protein. More particularly, the inventive viral protein should typically show 100% identity with critical functional portions (typically of at least several amino acids, often of at least 10, 20, 30, 40, 50 or more amino acids) of the relevant natural viral protein.

It is noted that in the case of many proteins a number of amino acid changes can be made without significantly affecting the functional activity and/or various other properties of the protein such as stability, etc. In particular, many proteins tolerate conservative amino acid changes, i.e., the substitution of an amino acid with a different amino acid having similar properties (conservative substitution) at many positions without significant reduction in activity. Conservative amino acid substitution is well known in the art and represents one approach to obtaining a polypeptide having similar or substantially similar properties to those of a given polypeptide while altering the amino acid sequence. In general, amino acids have been classified and divided into groups according to (1) charge (positive, negative, or uncharged); (2) volume and polarity; (3) Grantham's physico-chemical distance; and combinations of these. See, e.g., Zhang, J., *J. Mol. Evol.,* 50: 56-68, 2000; Grantham R., *Science,* 85: 862-864, 1974; Dagan, T., et al., *Mol. Biol. Evol.,* 19(7), 1022-1025, 2002; *Biochemistry,* 4th Ed., Stryer, L., et al., W. Freeman and Co., 1995; and U.S. Pat. No. 6,015,692. For example, amino acids may be divided into the following 6 categories based on volume and polarity: special (C); neutral and small (A, G, P, S, T); polar and relatively small (N, D, Q, E); polar and relatively large (R, H, K); nonpolar and relatively small (I, L, M, V), and nonpolar and relatively large (F, W, Y). A conservative amino acid substitution may be defined as one that replaces one amino acid with an amino acid in the same group. Thus a variety of functionally equivalent proteins can be derived by making one or more amino acid substitutions, e.g., conservative amino acid substitutions, in a given viral protein.

C. Clonal Root Lines

Figure 6:
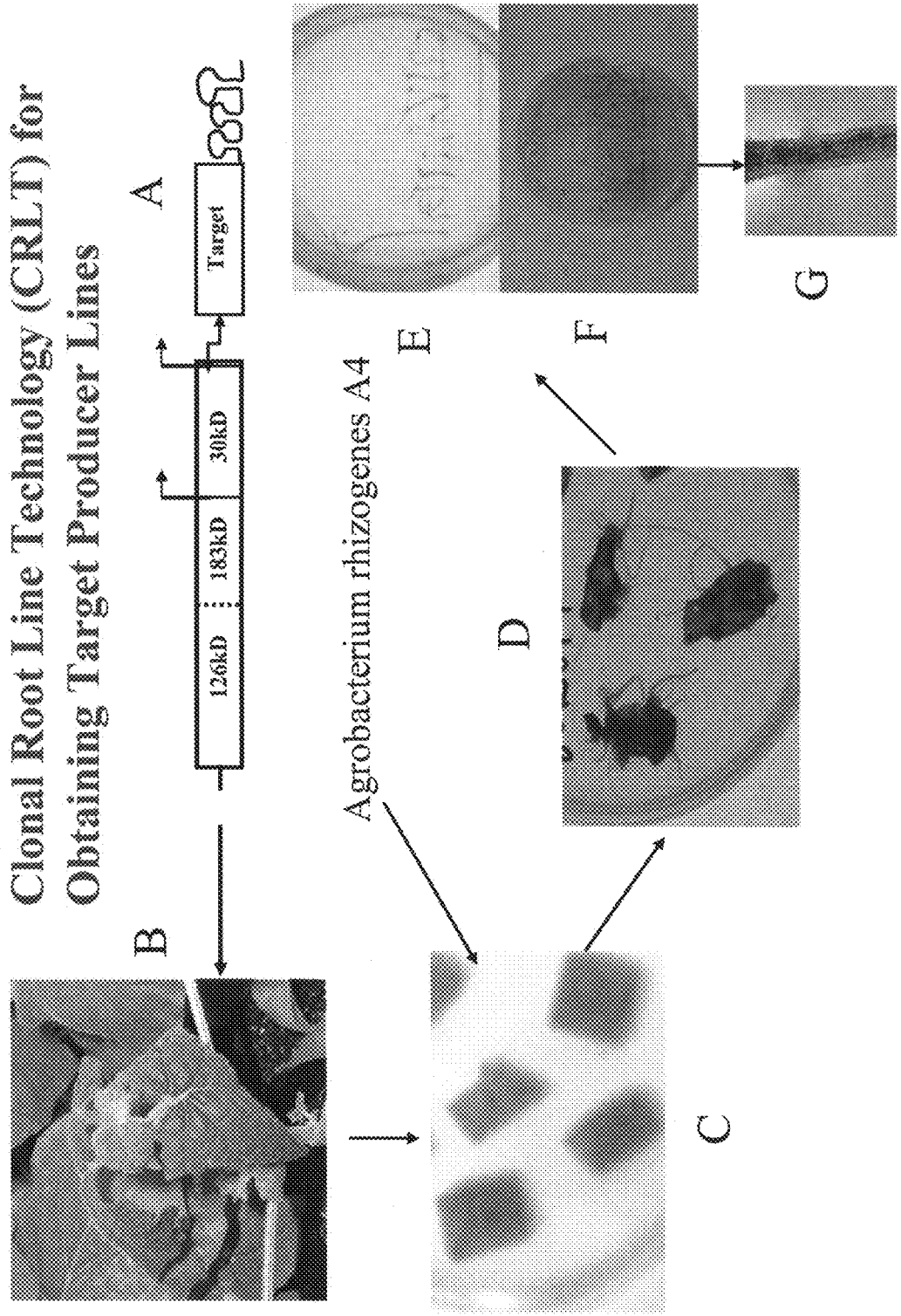
FIGS. 6A-6G illustrate steps in a method for generating clonal root lines for expression of a polynucleotide of interest (indicated as "target" in the figure) and clonal root lines generated using the method.

The present invention provides methods for generating a clonal root line in which a plant viral vector is used to direct expression of a polynucleotide of interest. FIGS. 6A-6E show steps in the method according to certain embodiments of the invention. As shown in FIG. 6, one or more viral expression vector(s) including a polynucleotide of interest operably linked to a promoter is introduced into a plant or a portion thereof according to any of a variety of known methods. For example, as described in Example 2, plant leaves can be inoculated with viral transcripts. The vectors themselves may be directly applied to plants (e.g., via abrasive inoculations, mechanized spray inoculations, vacuum infiltration, particle bombardment, or electroporation). Alternatively, virions may be prepared (e.g., from already infected plants), and may be applied to other plants according to known techniques.

Where infection is to be accomplished by direct application of a viral genome to a plant, any available technique may be used to prepare the genome. For example, many viruses that are usefully employed in accordance with the present invention have ssRNA genomes. ssRNA may be prepared by transcription of a DNA copy of the genome, or by replication of an RNA copy, either in vivo or in vitro. Given the readily availability of easy-to-use in vitro transcription systems (e.g., SP6, T7, reticulocyte lysate, etc.), and also the convenience of maintaining a DNA copy of an RNA vector, it is expected that inventive ssRNA vectors will often be prepared by in vitro transcription, particularly with T7 or SP6 polymerase. Infectious cDNA clones can also be used. Agrobacterially mediated gene transfer can also be used to transfer viral nucleic acids such as viral vectors (either entire viral genomes or portions thereof) to plant cells using, e.g., agroinfiltration, according to methods known in the art.

Preferably the plant or plant portion is then maintained (e.g., cultured or grown) under conditions suitable for replication of the viral transcript. In certain embodiments of the invention the virus spreads beyond the initially inoculated cell, e.g., locally from cell to cell and/or systemically from an initially inoculated leaf into additional leaves. However, in other embodiments of the invention the virus does not spread. Thus the viral vector may contain genes encoding functional MP and/or CP, but may be lacking one or both of such genes. In general, the viral vector is introduced into (infects) multiple cells in the plant or portion thereof. FIG. 6B shows a plant into which a viral vector (depicted schematically in FIG. 6A) has been introduced.

Following introduction of the viral vector into the plant, leaves are harvested. FIG. 6C shows leaf portions after harvesting from a virus-infected plant. In general, leaves may be harvested at any time following introduction of the viral vector. However, it may be preferable to maintain the plant for a period of time following introduction of the viral vector into the plant, e.g., a period of time sufficient for viral replication and, optionally, spread of the virus from the cells into which it was initially introduced. A clonal root culture (or multiple cultures) is prepared, e.g., by known methods further described below and in Example 2.

In general, any available method may be used to prepare a clonal root culture from a plant or plant tissue into which a viral vector has been introduced. One such method employs genes that exist in certain bacterial plasmids. These plasmids are found in various species of *Agrobacterium* that infect and transfer DNA to a wide variety of organisms. As a genus, *Agrobacteria* can transfer DNA to a large and diverse set of plant types including numerous dicot and monocot angiosperm species and gymnosperms (See, Gelvin, S. B., "*Agrobacterium*-Mediated Plant Transformation: the Biology behind the "Gene-Jockeying" Tool", *Microbiology and Molecular Biology Reviews*, 67(1): 16-37 (2003) and references therein, all of which are incorporated herein by reference). The molecular basis of genetic transformation of plant cells is transfer from the bacterium and integration into the plant nuclear genome of a region of a large tumor-inducing (Ti) or rhizogenic (Ri) plasmid that resides within various Agrobacterial species. This region is referred to as the T-region when present in the plasmid and as T-DNA when excised from the plasmid. Generally, a single-stranded T-DNA molecule is transferred to the plant cell in naturally occurring Agrobacterial infection and is ultimately incorporated (in double-stranded form) into the genome. Systems based on Ti plasmids are widely used for introduction of foreign genetic material into plants and for production of transgenic plants.

Infection of plants with various Agrobacterial species and transfer of the T-DNA has a number of effects. For example, *A. tumefaciens* causes crown gall disease while *A. rhizogenes* causes development of hairy roots at the site of infection, a condition known as "hairy root disease". Each root arises from a single genetically transformed cell. Thus root cells in the roots are clonal, and each root represents a clonal population of cells. The roots produced by *A. rhizogenes* infection are characterized by a high growth rate and genetic stability. (Giri, A. and Narasu, M. L., *Biotechnology Advances*, 18: 1-22 (2000) and references therein, all of which are incorporated herein by reference). In addition, such roots are able to regenerate genetically stable plants (Giri 2000).

In general, the present invention encompasses the use of any strain of *Agrobacteria*, particularly *A. rhizogenes* strains, that is capable of inducing formation of roots from plant cells. As mentioned above, a portion of the Ri plasmid (Ri T-DNA) is responsible for causing hairy root disease. While transfer of this portion of the Ri plasmid to plant cells can conveniently be accomplished by infection with *Agrobacteria* harboring the Ri plasmid, the invention also encompasses the use of alternative methods of introducing the relevant region into a plant cell. Such methods include any available method of introducing genetic material into plant cells including, but not limited to, biolistics, electroporation, PEG-mediated DNA uptake, Ti-based vectors, etc. The relevant portions of the Ri T-DNA can also be introduced into plant cells by use of a viral vector. The Ri genes can be included in the same vector that contains the polynucleotide of interest or in a different viral vector, which can be the same or a different type to that of the vector that contains the polynucleotide of interest. It is noted that the entire Ri T-DNA may not be required for production of hairy roots, and the invention encompasses the use of portions of the Ri T-DNA, provided that such portions contain sufficient genetic material to induce root formation, as known in the art. Additional genetic material, e.g., genes present within the Ri plasmid but not within the T-DNA, may also be transferred to the plant cell in accordance with the invention, particularly genes whose expression products facilitate integration of the T-DNA into the plant cell DNA.

In order to prepare a clonal root line in accordance with certain embodiments of the invention, the harvested leaf portions are contacted with *A. rhizogenes* under conditions suitable for infection and transformation. Example 2 describes one method for generating root lines from leaves into which a viral vector has been introduced. The leaf portions are maintained in culture to allow development of hairy roots. FIG. 6D shows hairy roots generated by individual cells in leaf portions infected with *A. rhizogenes*. Each root is clonal, i.e., cells in the root are derived from a single ancestral cell into which the Ri T-DNA was transferred. In accordance with the invention, a portion of such ancestral cells will also contain the viral vector. Thus cells in a root derived from such an ancestral cell will also contain the viral vector since it will be replicated and will be transmitted during cell division. Thus a high proportion, preferably at least 50%, more preferably at least 75%, at least 80%, at least 90%, at least 95%, or all (100%) or substantially all (at least 98%) of the cells will contain the viral vector. It is noted that since the viral vector is inherited by daughter cells within the clonal root, movement of the viral vector within the root is not necessary to maintain the viral vector throughout the root.

Individual clonal hairy roots may be removed from the leaf portion and further cultured, as shown in FIGS. 6E and 6F. Such roots are also referred to herein as root lines. FIG. 6E shows individual clonal roots placed in a line in a Petri dish. FIG. 6F shows the same root lines at higher magnification. The roots continue to grow. These roots were derived from plants into which a viral vector containing a GFP gene had been introduced. FIG. 6G shows a photograph of single root taken under UV light. Expression of GFP throughout the root is evident.

As described in Examples 2-4, a variety of different clonal root lines have been generated using the inventive methods. These root lines were generated using viral vectors containing polynucleotides of interest encoding GFP, hGH, and GCSF. The root lines were tested by Western blot. Root lines displayed a variety of different expression levels of the various polypeptides. Root lines displaying high expression were selected and further cultured. These root lines were subsequently tested again and shown to maintain high levels of expression over extended periods of time, indicating stability. The level of expression was comparable to or greater than expression in intact plants infected with the same viral vector used to generate the clonal root lines. In addition, the stability of expression of the root lines was superior to that obtained in plants infected with the same viral vector. Up to 80% of such virus-infected plants reverted to wild type after 2-3 passages. (Such passages involved inoculating plants with transcripts, allowing the infection (local or systemic) to become established, taking a leaf sample, and inoculating fresh plants that are subsequently tested for expression.)

The root lines may be cultured on a large scale for production of polypeptides of interest as discussed further below. It is noted that the clonal root lines (and cell lines derived from the clonal root lines) can generally be maintained in medium that does not include various compounds, e.g., plant growth hormones such as auxins, cytokinins, etc., that are typically employed in the culture of root and plant cells. This feature greatly reduces the expense associated with tissue culture, and the inventors expect that it will contribute significantly to the economic feasibility of protein production using plants.

Any of a variety of methods may be used to select clonal roots that express a polynucleotide of interest. Western blots, ELISA assays, etc., can be used to detect an encoded polypeptide. In the case of detectable markers such as GFP, alternative methods such as visual screens can be performed. If a viral vector that contains a polynucleotide that encodes a selectable marker is used, an appropriate selection can be imposed (e.g., the leaf material and/or roots derived therefrom can be cultured in the presence of an appropriate antibiotic or nutritional condition and surviving roots identified and isolated). Certain viral vectors contain two or more polynucleotides of interest, e.g., two or more polynucleotides encoding different polypeptides. If one of these is a selectable or detectable marker, clonal roots that are selected or detected by selecting for or detecting expression of the marker will have a high probability of also expressing the second polynucleotide. Screening for root lines that contain particular polynucleotides can also be performed using PCR and other nucleic acid detection methods.

Alternatively, clonal root lines can also be screened for presence of the virus by inoculating host plants that will form local lesions as a result of virus infection (e.g., hypersensitive host plants). For example, 5 mg of root tissue can be homogenized in 50 ul of phosphate buffer and used to inoculate a single leaf of a tobacco plant. If the virus is present in root cultures, within two to three days characteristic lesions will appear on the infected leaves. This means that the root line contains recombinant virus that carries the polynucleotide of interest (target gene). If no local lesions are formed, there is no virus, and the root line is rejected as negative. This method is highly time and cost efficient. After initially screening for the presence of virus, roots that contain the virus are subjected to secondary screening, e.g., by Western blot or ELISA to select high expressers. Additional screens, e.g., screens for rapid growth, growth in particular media or under particular environmental conditions, etc., can also be applied. These screening methods may, in general, be applied in the development of any of the clonal root lines, clonal root cell lines, clonal plant cell lines, and/or clonal plants described herein.

As will be evident to one of ordinary skill in the art, a variety of modifications may be made to the above description of the inventive methods for generating clonal root lines that contain a viral vector. Such modifications are within the scope of the invention. For example, while it is generally preferred to introduce the viral vector into an intact plant or portion thereof prior to introduction of the Ri T-DNA genes, in certain embodiments of the invention the Ri-DNA is introduced prior to introducing the viral vector. In addition, it is also possible to contact intact plants with *A. rhizogenes* rather than harvesting leaf portions and then exposing them to the bacterium.

Other methods of generating clonal root lines from single cells of the plant or portion thereof that harbor the viral vector can also be used (i.e., methods not using *A. rhizogenes* or genetic material from the Ri plasmid). For example, treatment with certain plant hormones or combinations of plant hormones is known to result in generation of roots from plant tissue.

In certain embodiments of the invention rather than introducing a single viral vector type into the plant, multiple different viral vectors are introduced. Such vectors may, for example, trans-complement each other with respect to functions such as replication, cell-to-cell movement, and/or long distance movement. The vectors may contain different polynucleotides of interest, e.g., polynucleotides that encode individual polypeptides that associate to form a single protein complex such as antibodies, etc., or polynucleotides that encode different enzymes in a biosynthetic pathway. Selection for roots that express multiple polypeptides of interest may be performed as described above for single polynucleotides or polypeptides.

D. Clonal Cell Lines Derived from Clonal Root Lines

As described above, the invention provides methods for generating clonal root lines, wherein cells in the root lines contain a viral vector. As is well known in the art, a variety of different cell lines can be generated from roots. For example, root cell lines can be generated from individual root cells obtained from the root using a variety of known methods. Such root cell lines may be obtained from various different root cell types within the root. In general, root material is harvested and dissociated (e.g., physically and/or enzymatically digested) to release individual root cells, which are then further cultured. Complete protoplast formation is generally not necessary. If desired, root cells can be plated at very dilute cell concentrations, so as to obtain root cell lines from single root cells. Root cell lines derived in this manner are clonal root cell lines contain the viral vector. Such root cell lines therefore exhibit stable expression of the polynucleotide of interest. Clonal plant cell lines can also be obtained in a similar manner from the clonal roots, e.g., by culturing dissociated root cells in the presence of the appropriate plant hormones. Screens and successive rounds of enrichment can be used to identify cell lines that express the polynucleotide of interest at high levels. However, if the clonal root line from which the cell line is derived already expresses at high levels, such additional screens may be unnecessary.

As in the case of the clonal root lines, cells of a clonal root cell line are derived from a single ancestral cell that contains the viral vector and will, therefore, also contain the viral vector since it will be replicated and will be transmitted during cell division. Thus a high proportion, preferably at least 50%, more preferably at least 75%, at least 80%, at least 90%, at least 95%, or all (100%) or substantially all (at least 98%) of the cells will contain the viral vector. It is noted that since the viral vector is inherited by daughter cells within the clonal root cell line, movement of the viral vector among the cells is not necessary to maintain the viral vector. The clonal root cell lines can be used for production of a polynucleotide of interest as described below.

E. Clonal Plant Cell Lines

The present invention provides methods for generating a clonal plant cell line in which a plant viral vector is used to direct expression of a polynucleotide of interest. According to the inventive method, one or more viral expression vector(s) including a polynucleotide of interest operably linked to a promoter is introduced into cells of a plant cell line that is maintained in cell culture. A number of plant cell lines from various plant types are known in the art, any of which can be used. Newly derived cell lines can also be generated according to known methods for use in practicing the invention. A viral vector is introduced into cells of the plant cell line according to any of a number of methods. For example, as described in Example 5, protoplasts can be made and viral transcripts then electroporated into the cells. Other methods of introducing a plant viral vector into cells of a plant cell line can also be used.

Figure 13:
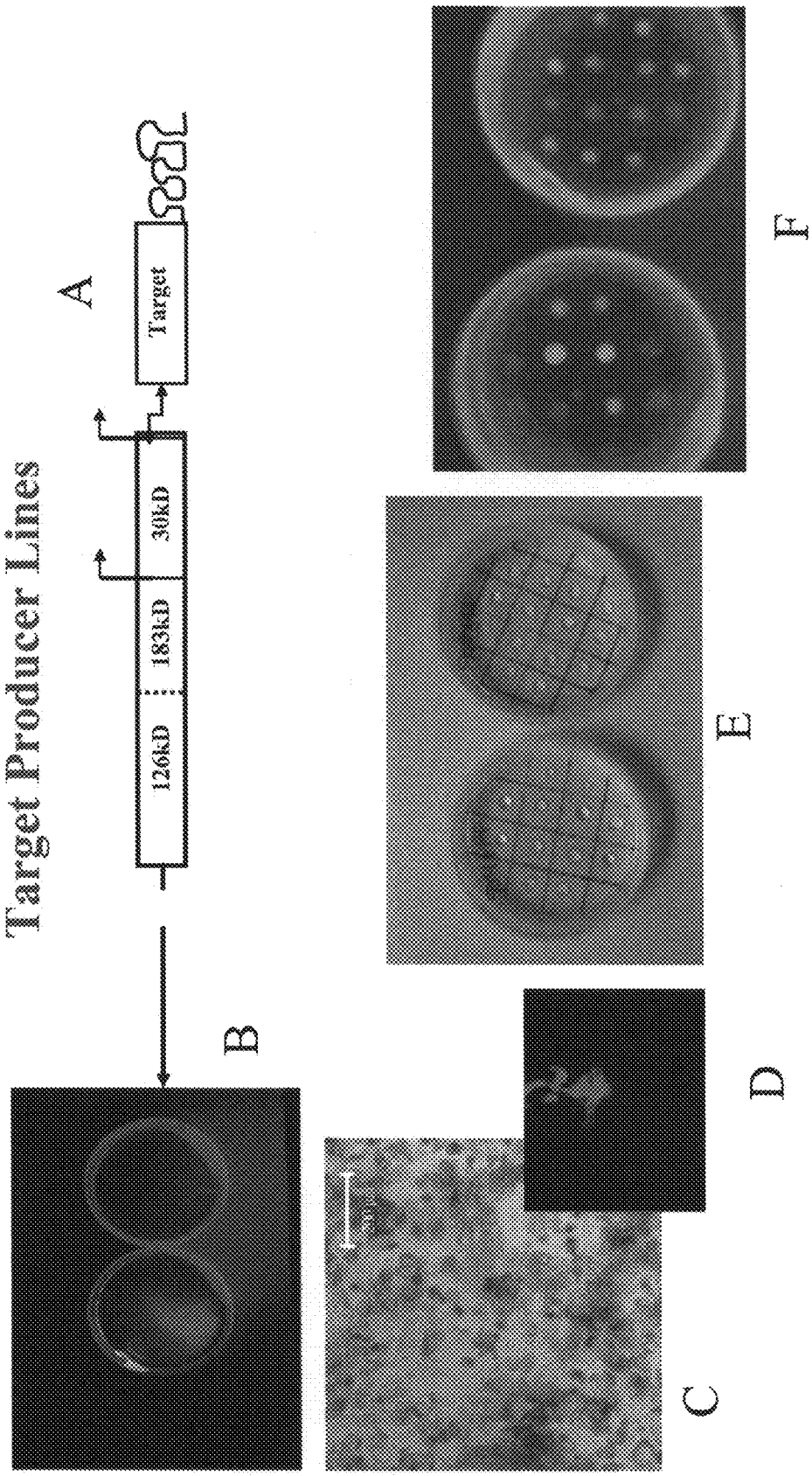
FIG. 13 illustrates steps in a method for generating clonal plant cell lines for expression of a polynucleotide of interest and identifying cell lines that display expression.

FIG. 13 shows steps in a method for generating clonal plant cell lines in accordance with the invention. FIG. 13A shows a viral vector suitable for introduction into plant cells (e.g., protoplasts). Following introduction of the viral vector, the plant cell line may be maintained in tissue culture, e.g., as shown in FIGS. 13B and 13C. During this time the viral vector may replicate, and polynucleotides of interest may be expressed. Clonal plant cell lines are derived from the culture, e.g., by a process of successive enrichment. For example, as shown in FIG. 13E, samples may be removed from the culture, optionally with dilution so that the concentration of cells is low, and plated in Petri dishes in individual droplets. The droplets are then maintained to allow cell division.

It will be appreciated that the droplets may contain a variable number of cells, depending on the initial density of the culture and the amount of dilution. The cells can be diluted such that most droplets contain either 0 or 1 cell if it is desired to obtain clonal cell lines expressing the polynucleotide of interest after only a single round of enrichment. However, it can be more efficient to select a concentration such that multiple cells are present in each droplet and then screen the droplets to identify those that contain expressing cells. In general, any appropriate screening procedure can be employed. For example, selection or detection of a detectable marker such as GFP can be used. FIG. 13F is a photograph taken under UV light and showing individual droplets in which cell lines expressing GFP from a viral vector are present. Western blots or ELISA assays can also be used. Individual droplets (100 ul) contain more than enough cells for performance of these assays. Multiple rounds of enrichment are performed to isolate successively higher expressing cell lines. Single clonal plant cell lines (i.e, populations derived from a single ancestral cell) can be generated by further limiting dilution using standard methods for single cell cloning. However, it is not necessary to isolate individual clonal lines. A population containing multiple clonal cell lines can also be used for expression of a polynucleotide of interest.

In general, certain considerations described above for generation of clonal root lines also apply to the generation of clonal plant cell lines. For example, a diversity of viral vectors containing one or more polynucleotides of interest can be used as can combinations of multiple different vectors. Similar screening methods can also be used. As in the case of the clonal root lines and clonal root cell lines, cells of a clonal plant cell line are derived from a single ancestral cell that contains the viral vector and will, therefore, also contain the viral vector since it will be replicated and will be transmitted during cell division. Thus a high proportion, preferably at least 50%, more preferably at least 75%, at least 80%, at least 90%, at least 95%, or all (100%) or substantially all (at least 98%) of the cells will contain the viral vector. It is noted that since the viral vector is inherited by daughter cells within the clonal plant cell line, movement of the viral vector among the cells is not necessary to maintain the viral vector. The clonal plant cell line can be used for production of a polypeptide of interest as described below.

F. Clonal Plants

Clonal plants can be generated from the clonal roots, clonal root cell lines, and/or clonal plant cell lines produced according to the various methods described above. Methods for the generation of plants from roots, root cell lines, and plant cell lines such as the clonal root lines, clonal root cell lines, and clonal plant cell lines described herein are well known in the art (See, e.g., Peres et al., *Plant Cell, Tissue, and Organ Culture* 65, 37-44, 2001 and standard reference works on plant molecular biology and biotechnology cited elsewhere herein. The invention therefore provides a method of generating a clonal plant comprising steps of (i) generating a clonal root line, clonal root cell line, or clonal plant cell line according to any of the inventive methods described above; and (ii) generating a whole plant from the clonal root line, clonal root cell line, or clonal plant. The clonal plants may be propagated and grown according to standard methods. Example 7 describes generation of a clonal plant from a clonal root line containing a viral vector that encodes human growth hormone.

As in the case of the clonal root lines, clonal root cell lines, and clonal plant cell lines, the cells of a clonal plant are derived from a single ancestral cell that contains the viral vector and will, therefore, also contain the viral vector since it will be replicated and will be transmitted during cell division. Thus a high proportion, preferably at least 50%, more preferably at least 75%, at least 80%, at least 90%, at least 95%, or all (100%) or substantially all (at least 98%) of the cells will contain the viral vector. It is noted that since the viral vector is inherited by daughter cells within the clonal plant, movement of the viral vector is not necessary to maintain the viral vector.

II. Plant Species

Any plant susceptible to viral infection may be utilized in accordance with the present invention. In general, it will often be desirable to utilize plants that are amenable to growth under defined conditions, for example in a greenhouse and/or in aqueous systems. It may also be desirable to select plants that are not typically consumed by human beings or domesticated animals and/or are not typically part of the human food chain, so that they may be grown outside without concern that the expressed polynucleotide may be undesirably ingested. In other embodiments, however, it will be desirable to employ edible plants.

Often, certain desirable plant characteristics will be determined by the particular polynucleotide to be expressed. To give but a few examples, when the polynucleotide encodes a protein to be produced in high yield (as will often be the case, for example, when therapeutic proteins are to be expressed), it will often be desirable to select plants with relatively high biomass (e.g., tobacco, which has the additional advantages that it is highly susceptible to viral infection, has a short growth period, and is not in the human food chain). Where the polynucleotide encodes a protein whose full activity requires (or is inhibited by) a particular post-translational modification, the ability (or inability) of certain plant species to accomplish the relevant modification (e.g., a particular glycosylation) may direct selection.

In certain preferred embodiments of the invention, crop plants, or crop-related plants are utilized. In some particularly preferred embodiments, edible plants are utilized.

Preferred plants for use in accordance with the present invention include Angiosperms, Bryophytes (e.g., Hepaticae, Musci, etc.), Pteridophytes (e.g., ferns, horsetails, lycopods), Gymnosperms (e.g., conifers, cycase, Ginko, Gnetales), and Algae (e.g., Chlorophyceae, Phaeophyceae, Rhodophyceae, Myxophyceae, Xanthophyceae, and Euglenophyceae). Particularly preferred are members of the family Leguminosae (Fabaceae; e.g., pea, alfalfa, soybean); Gramineae (Poaceae; e.g., corn, wheat, rice); Solanaceae, particularly of the genus *Lycopersicon* (e.g., tomato), *Solanum* (e.g., potato, eggplant), *Capsium* (e.e., pepper), or *Nicotiana* (e.g., tobacco); Umbelliferae, particularly of the genus *Daucus* (e.g., carrot), *Apium* (e.g., celery), or *Rutaceae* (e.g., oranges); Compositae, particularly of the genus *Lactuca* (e.g., lettuce); Brassicaceae (Cruciferae), particularly of the genus *Brassica* or *Sinapis*. Particularly preferred Brassicaceae family members include *Brassica campestris, B. carinata, B. juncea, B. napus, B. nigra, B. oleraceae, B. tournifortii, Sinapis alba*, and *Raphanus sativus*.

III. Polynucleotides and Polypeptides of Interest

The teachings of the present invention may be employed to deliver to and/or express in plant cells any polynucleotide of interest. For example, protein-coding polynucleotides may express enzymes, antibodies, hormones, cytokines, regulatory factors, structural proteins, or any other protein or polypeptide of interest. Encoded proteins may be naturally-occurring proteins, or may be designed or engineered proteins, including for instance fusion proteins (e.g., fusion proteins incorporating part or all of a plant virus protein such as MP or CP). See, e.g., U.S. Pat. Nos. 6,448,070 and 6,660,500. Numerous types of fusion proteins may be encoded. A heterologous sequence may be fused to the 5' or 3' end of a plant virus protein or located internally. Numerous sequences of diverse origin may be included within a single fusion protein. The encoded protein may comprise a cleavage site, which may be encoded by the inserted polynucleotide or by the viral vector. See, e.g., U.S. Pat. No. 6,740,740. For example, the vector may comprise a portion that encodes a cleavage site upstream of a portion that encodes CP so that when a polynucleotide of interest is inserted between the CP promoter and the portion that encodes a cleavage site, the resulting open reading frame encodes a fusion protein containing a portion encoded by the polynucleotide of interest, a cleavage site, and part or all of the CP. Cleavage of the fusion protein at the cleavage site releases the encoded polypeptide of interest. The cleavage site may be a site for cleavage by chemical means (e.g., cyanogen bromide) or by enzymatic means (e.g., by a protease such as trypsin, chymotrypsin, thrombin, pepsin, *Staphylococcus aureus* V8 protease, and Factor Xa protease).

In certain embodiments of the invention the polynucleotide of interest comprises a portion encoding a tag, e.g., a 6×-His tag, HA tag, Myc tag, FLAG tag, etc. Such tags may simplify the detection, isolation and/or purification of the protein. In certain embodiments of the invention the tag is a cleavable tag, e.g., a tag cleavable by chemical means or by enzymatic means as described above. Including a cleavage site allows the tag to be readily be removed from the translated polypeptide, e.g., after purification, resulting in a protein with wild type sequence. It is to be understood that the tag and/or cleavage site may be present within a viral vector into which a particular polynucleotide of interest is to be inserted and need not be present within the inserted polynucleotide itself. Once the polynucleotide is inserted, the entire portion comprising the region(s) that encode the tag, cleavage site, and newly inserted polynucleotide is considered a polynucleotide of interest.

In some instances, it may be desirable to utilize the inventive system to express more than one polypeptide chain in the same clonal root or plant cell line or clonal plant (e.g., using two different viral vectors each of which directs expression of a polynucleotide, inserting two different polynucleotides into one viral vector, utilizing a transgenic plant that expresses one or more polynucleotides to generate a clonal root or plant cell line or clonal plant), for example in order to produce a multimeric protein or to simultaneously produce two different proteins such as a protein of interest and a detectable or selectable marker).

In certain preferred embodiments of the invention, a polynucleotide that encodes a therapeutically active protein is employed. Exemplary proteins that have been approved for therapeutic uses include, for example, insulin, human growth hormone, interferons, albumin, tPA, erythropoietin, interleukins, factor VIII, DNase, factor IX, PDGF, FSH, TNF receptor (soluble form), calcitonin, and a variety of immunoglobulins. Of course, the invention is not limited to such approved proteins, but encompasses expression of any polynucleotide(s), whether protein-coding or not, and particularly encompasses expression of any polynucleotide encoding any therapeutically active protein, whether prokaryotic or eukaryotic in origin, etc.

Generally, the pharmaceutical proteins of interest include, but are not limited to, hormones (insulin, thyroid hormone, catecholamines, gonadotrophines, trophic hormones, prolactin, oxytocin, dopamine, bovine somatotropin, leptins and the like), growth hormones (e.g., human grown hormone), growth factors (e.g., epidermal growth factor, nerve growth factor, insulin-like growth factor and the like), growth factor receptors, cytokines and immune system proteins (e.g., interleukins, colony stimulating factor (CSF), granulocyte colony stimulating factor (G-CSF), granulocyte-macrophage colony stimulating factor (GM-CSF), erythropoietin, tumor necrosis factor (TNF), interfersons, integrins, addressins, seletins, homing receptors, T cell receptors, immunoglobulins, soluble major histocompatibility complex antigens, immunologically active antigens such as bacterial, parasitic, or viral antigens or allergens), autoantigens, antibodies), enzymes (tissue plasminogen activator, streptokinase, cholesterol biosynthestic or degradative, steriodogenic enzymes, kinases, phosphodiesterases, methylases, de-methylases, dehydrogenases, cellulases, proteases, lipases, phospholipases, aromatases, cytochromes, adenylate or guanylaste cyclases, neuramidases and the like), receptors (steroid hormone receptors, peptide receptors), binding proteins (sterpod binding proteins, growth hormone or growth factor binding proteins and the like), transcription and translation factors, oncoproteins or proto-oncoproteins (e.g., cell cycle proteins), muscle proteins (myosin or tropomyosin and the like), myeloproteins, neuroactive proteins, tumor growth suppressing proteins (angiostatin or endostatin, both of which inhibit angiogenesis), anti-sepsis proteins (bectericidal permeability-increasing protein), structural proteins (such as collagen, fibroin, fibrinogen, elastin, tubulin, actin, and myosin), blood proteins (thrombin, serum albumin, Factor VII, Factor VIII, insulin, Factor IX, Factor X, tissue plasminogen activator, Protein C, von Willebrand factor, antithrombin III, glucocerebrosidase, erythropoietin granulocyte colony stimulating factor (GCSF) or modified Factor VIII, anticoagulants such as hirudin) and the like.

In one particular example, the present invention may be utilized to produce vaccine components. In general, it is desirable to include in vaccines proteins, or portions of proteins, to which a human or animal immune system is exposed when the human or animal is infected with a pathogen, or suffering some other undesirable event (e.g., development of a tumor). Thus, proteins or polypeptides that may be formulated in a vaccine include virtually any potentially antigenic protein or portion thereof, for example, viral coat proteins, viral fusion proteins, viral envelope proteins, viral glycoproteins, bacterial or fungal cell wall proteins, toxin proteins, parasite coat proteins, tumor-specific antigens, etc., or portions of any of the foregoing. See, e.g., WO9640229. Viruses of interest include HIV, respiratory syncytial virus (RSV), rabies virus, polio virus, pneumoviruses, metapneumoviruses, influenza viruses, poxviruses (including smallpox), rhinoviruses, coronaviruses, adenoviruses, herpesviruses, hantaviruses, Ebola virus, Yellow Fever virus, Dengue virus, hepatitis viruses (e.g., hepatitis A, B, C, D, E, F, or G virus) etc. Bacteria of interest include *Neisseria, Pneumococcus, Streptococcus, H. influenzae, Staphylococcus*, anthrax, etc. Parasites of interest include *Plasmodium, Leishmania, Toxoplasma, Ascaris*, hookworm and other nematodes, ameba, flukes, etc.

In other embodiments, the inventive system may be used to express a polynucleotide encoding an enzyme that synthesizes or modifies a biologically active agent. For instance, certain enzymes (e.g., polyketide synthases, polypeptide synthetases, terpene synthases, etc.) synthesize small molecules with interesting biological activities, including therapeutic activities (e.g., antibiotic, anticancer, immunosuppressive activities, etc.). Also, a large number of enzymes that modify protein or small molecule substrates (e.g., kinases, hydrolases, transferases, etc.) is known. See U.S. Pat. No. 6,500,644 for additional proteins that can be desirably expressed in plants using the inventive systems described herein.

In certain embodiments of the invention the polynucleotide encodes a component (e.g., an enzyme) in a biosynthetic pathway. Plants are a source of numerous natural products of use for medicinal and/or industrial purposes and others. It is of interest to increase the level or efficiency by which such products are produced. To this end, a polynucleotide of interest may encode a biosynthetic enzyme, e.g., an enzyme that catalyzes a rate-limiting step in a biosynthetic pathway, by which such natural product(s) are synthesized.

In other embodiments, the inventive system may be used to produce diagnostic or research reagents including, for example, antibodies.

In yet other embodiments of the invention the polynucleotide encodes a protein that enhances plant growth or survival in any of a variety of ways. For example, the protein may enhance the ability of the plant to extract nutrients from soil or culture medium, may confer resistance to an environmental condition such as temperature, salinity, etc., or may confer resistance to a pathogen such as a virus, bacterium, fungus, nematode, insect, etc. An example is the various plant peptides known as defensins (Thomma, B. P., et al., *Planta*, 216(2):193-202, 2002) Such proteins include both endogenous plant proteins (i.e., proteins that are naturally expressed in the plant from which the clonal root line, clonal plant cell line, or clonal plant is derived) and non-endogenous proteins.

In yet other embodiments, the inventive system may be utilized to produce nutritionally relevant proteins or other products. Nutritionally relevant proteins include, for example, proteins that are found naturally in foods consumed by humans or domesticated animals (e.g., cats, dogs). Other examples include proteins having a balanced amino acid composition, e.g., proteins having an amino acid composition such as those used for total parenteral nutrition (TPN), etc.

In still other embodiments, the inventive system may be utilized to express polynucleotides that do not necessarily encode proteins, for example to produce active RNA species, e.g., ribozymes or interfering RNAs that silence gene expression (either long double-stranded RNAs or short interfering RNAs (siRNAs), microRNAs or microRNA precursors, short hairpin RNAs (shRNAs), etc. See, e.g., U.S. Pat. Nos. 6,531,647; 6,635,805 and U.S. Pub. No. 20040019930. In some embodiments, ribozymes or interfering RNAs may be produced that target plant genes, so that an altered plant is created, for example that does not express a particular receptor for a plant pathogen, or a particular allergenic protein.

IV. Culturing or Growing Clonal Root Lines, Clonal Root Cell Lines, Clonal Plant Cell Lines, and Clonal Plants In general, standard methods known in the art may be used for culturing or growing the clonal root lines, clonal root cell lines, clonal plant cell lines, and clonal plants of the invention. A wide variety of culture media and bioreactors have been employed to culture hairy root cells, root cell lines, and plant cells. See, for example, Giri, A. and Narasu, M. L., *Biotechnol. Adv.* 18:1-22, 2000; Rao, S. R. and Ravishankar, G. A., *Biotechnol. Adv.* 20:101-153, 2002, and references in both of the foregoing, all of which are incorporated herein by reference. Clonal plants may be grown in any suitable manner.

V. Isolation and/or Formulation of Polynucleotide Expression Products

In many embodiments of the present invention, it will be desirable to isolate polynucleotide expression products from the plant tissue(s), e.g., roots, root cells, plants, plant cells, that express them. It may also be desirable to formulate such isolated products for their intended use (e.g., as a pharmaceutical or diagnostic agent, or as a reagent, etc.). In other embodiments, it will be desirable to formulate the products together with some or all of the plant tissues that express them.

Where it is desirable to isolate the expression product from some or all of the plant cells or tissues that express it, any available purification techniques may be employed. Those of ordinary skill in the art are familiar with a wide range of fractionation and separation procedures (see, for example, Scopes et al., *Protein Purification: Principles and Practice*, 3$^{rd}$ Ed., Janson et al., 1993; *Protein Purification: Principles, High Resolution Methods, and Applications*, Wiley-VCH, 1998; Springer-Verlag, NY, 1993; Roe, *Protein Purification Techniques*, Oxford University Press, 2001, each of which is incorporated herein by reference). Often, it will be desirable to render the product more than about 50%, preferably more than about 60%, 70%, 80%, 85%, 90%, 91%, 92%, 93%, 94%, 95%, 96%, 97%, 98%, or 99% pure. See, e.g., U.S. Pat. Nos. 6,740,740 and 6,841,659 for discussion of certain methods useful for purifying substances from plant tissues or fluids.

Where it is desirable to formulate the product together with the plant material, it will often be desirable to have utilized a plant that is not toxic to the relevant recipient (e.g., a human or other animal). Relevant plant tissue (e.g., cells, roots, leaves) may simply be harvested and processed according to techniques known in the art, with due consideration to maintaining activity of the expressed product. In certain embodiments of the invention, it is desirable to have expressed the polynucleotide in an edible plant (and, specifically in edible portions of the plant) so that the material can subsequently be eaten. For instance, where the polynucleotide encodes a nutritionally relevant protein, or a therapeutic protein that is active after oral delivery (when properly formulated), it may be desirable to produce the protein in an edible plant portion, and to formulate the expressed polynucleotide for oral delivery together with the some or all of the plant material with which the polynucleotide was expressed.

Where the polynucleotide encodes or produces a therapeutic agent, it may be formulated according to know techniques. For example, an effective amount of a pharmaceutically active product can be formulated together with one or more organic or inorganic, liquid or solid, pharmaceutically suitable carrier materials. A pharmaceutically active product produced according to the present invention may be employed in dosage forms such as tablets, capsules, troches, dispersions, suspensions, solutions, capsules, creams, ointments, aerosols, powder packets, liquid solutions, solvents, diluents, surface active agents, isotonic agents, thickening or emulsifying agents, preservatives, and solid bindings, as long as the biological activity of the protein is not destroyed by such dosage form.

Materials that can serve as pharmaceutically acceptable carriers include, but are not limited to sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such a propylene glycol, esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening agents, flavoring agents, and perfuming agents, preservatives, and antioxidants can also be present in the composition, according to the judgment of the formulator (see also *Remington's Pharmaceutical Sciences*, Fifteenth Edition, E. W. martin (Mack Publishing Co., Easton Pa., 1975). For example, the polynucleotide expression product may be provided as a pharmaceutical composition by means of conventional mixing granulating dragee-making, dissolving, lyophilizing, or similar processes.

In certain preferred embodiments, it may be desirable to prolong the effect of a pharmaceutical preparation by slowing the absorption of the pharmaceutically active product (e.g., protein) that is subcutaneously or intramuscularly injected. This may be accomplished by the use of a liquid suspension of crystalline or amorphous material with poor water solubility. The rate of absorption of the product then depends upon its rate of dissolution, which in turn, may depend upon size and form. Alternatively, delayed absorption of a parenterally administered product is accomplished by dissolving or suspending the product in an oil vehicle. Injectable depot forms are made by forming microcapsule matrices of the protein in biodegradable polymers such as polylactide-polyglycolide. Depending upon the ratio of product to polymer and the nature of the particular polymer employed, the rate of release can be controlled. Examples of other biodegradable polymers include poly(orthoesters) and poly(anhydrides). Depot injectable formulations may be prepared by entrapping the product in liposomes or microemulsions, which are compatible with body tissues.

Enterally administered preparations of pharmaceutically active products may be introduced in solid, semi-solid, suspension or emulsion form and may be compounded with any pharmaceutically acceptable carriers, such as water, suspending agents, and emulsifying agents. The expression products may also be administered by means of pumps or sustained-release forms, especially when administered as a preventive measure, so as to prevent the development of disease in a subject or to ameliorate or delay an already established disease.

Pharmaceutically active products, optionally together with plant tissue, are particularly well suited for oral administration as pharmaceutical compositions. Harvested plant material may be processed in any of a variety of ways (e.g., air drying, freeze drying, extraction etc.), depending on the properties of the desired therapeutic product and its desired form. In preferred embodiments, such compositions as described above are ingested orally alone or ingested together with food or feed or a beverage. Compositions for oral administration include plants; extractions of the plants, and proteins purified from infected plants provided as dry powders, foodstuffs, aqueous or non-aqueous solvents, suspensions, or emulsions. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medial parenteral vehicles including sodium chloride solution, Ringer's dextrose solution, dextrose plus sodium chloride solution, Ringer's solution containing lactose or fixed oils. Examples of dry powders include any plant biomass that has been dried, for example, freeze dried, air dried, or spray dried. For example, the plants may be air dried by placing them in a commercial air dryer at about 120 degrees Fahrenheit until the biomass contains less than 5% moisture by weight. The dried plants may be stored for further processing as bulk solids or further processed by grinding to a desired mesh sized powder. Alternatively, freeze-drying may be used for products that are sensitive to air-drying. Products may be freeze dried by placing them into a vacuum drier and dried frozen under a vacuum until the biomass contains less than about 5% moisture by weight. The dried material can be further processed as described herein.

Plant-derived material may be administered as or together with one or more herbal preparations. Useful herbal preparations include liquid and solid herbal preparations. Some examples of herbal preparations include tinctures, extracts (e.g., aqueous extracts, alcohol extracts), decoctions, dried preparations (e.g., air-dried, spray dried, frozen, or freeze-dried), powders (e.g., lyophilized powder), and liquid. Herbal preparations can be provided in any standard delivery vehicle, such as a capsule, tablet, suppository, liquid dosage, etc. Those skilled in the art will appreciate the various formulations and modalities of delivery of herbal preparations that may be applied to the present invention.

Those skilled in the art will also appreciate that a particularly preferred method of obtaining the desired pharmaceutically active products is by extraction. Plant material (e.g., roots, leaves, etc.) may be extracted to remove the desired products from the residual biomass, thereby increasing the concentration and purity of the product. Plants may also be extracted in a buffered solution. For example, the plant material may be transferred into an amount of ice-cold water at a ratio of one to one by weight that has been buffered with, e.g., phosphate buffer. Protease inhibitors can also be added as required. The plant material can be disrupted by vigorous blending or grinding while suspended in the buffer solution and the extracted biomass removed by filtration or centrifugation. The product carried in solution can be further purified by additional steps or converted to a dry powder by freeze-drying or precipitation. Extraction can also be carried out by pressing. Plants or roots can also be extracted by pressing in a press or by being crushed as they are passed through closely spaced rollers. The fluids expressed from the crushed plants or roots are collected and processed according to methods well known in the art. Extraction by pressing allows the release of the products in a more concentrated form. However, the overall yield of the product may be lower than if the product were extracted in solution.

Inventive root lines, cell lines, plants, extractions, powders, dried preparations and purified protein or nucleic acid products, etc., can also be in encapsulated form with or without one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active product may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

In other particularly preferred embodiments, a plant or portion thereof expressing a pharmaceutically active product according to the present invention, or biomass thereof, is administered orally as medicinal food. Such edible compositions are consumed by eating raw, if in a solid form, or by drinking, if in liquid form. In a preferred embodiment, the plant material is directly ingested without a prior processing step or after minimal culinary preparation. In an alternative embodiment, the plant biomass is processed and the material recovered after the processing step is ingested.

Processing methods preferably used in the present invention are methods commonly used in the food or feed industry. The final products of such methods still include a substantial amount of the expressed pharmaceutically active polynucleotide or polypeptide and are preferably conveniently eaten or drunk. The final product may also be mixed with other food or feed forms, such as salts, carriers, favor enhancers, antibiotics, and the like, and consumed in solid, semi-solid, suspension, emulsion, or liquid form. In another preferred embodiment, such methods include a conservation step, such as, e.g., pasteurization, cooking, or addition of conservation and preservation agents. Any plant is used and processed in the present invention to produce edible or drinkable plant matter. The amount of pharmaceutically active polynucleotide or polypeptide expression product in a plant-derived preparation may be tested by methods standard in the art, e.g., gel electrophoresis, ELISA, or Western blot analysis, using a probe or antibody specific for the product. This determination may be used to standardize the amount of polynucleotide or protein ingested. For example, the amount of therapeutically active product may be determined and regulated, for example, by mixing batches of product having different levels of product so that the quantity of material to be drunk or eaten to ingest a single dose can be standardized.

A pharmaceutically active polynucleotide or protein produced in a plant cell or tissue and eaten by a host is preferably absorbed by the digestive system. One advantage of the ingestion of plant tissue that has been only minimally processed is to provide encapsulation or sequestration of the polynucleotide or protein in cells of the plant. Thus, the product may receive at least some protection from digestion in the upper digestive tract before reaching the gut or intestine and a higher proportion of active product would be available for uptake.

The pharmaceutical compositions of the present invention can be administered therapeutically or prophylactically. In certain preferred embodiments, the compositions may be used to treat or prevent a disease. For example, any individual who suffers from a disease or who is at risk of developing a disease may be treated. It will be appreciated that an individual can be considered at risk for developing a disease without having been diagnosed with any symptoms of the disease. For example, if the individual has a particular genetic marker identified as being associated with increased risk for developing a particular disease, that individual will be considered at risk for developing the disease. Similarly, if members of an individual's family have been diagnosed with a particular disease, e.g., cancer, the individual may be considered to be at risk for developing that disease.

Liquid dosage forms for oral administration include, but are not limited to, pharmaceutically acceptable emulsions, microemulsions, solutions, suspensions, syrups, and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Compositions for rectal or vaginal administration are preferably suppositories which can be prepared by mixing the compositions of this invention with suitable non-irritating excipients or carriers such as cocoa butter, polyethylene glycol or a suppository wax which are solid at ambient temperature but liquid at body temperature and therefore melt in the rectum or vaginal cavity and release the active protein.

Dosage forms for topical or transdermal administration of a pharmaceutical composition of this invention include ointments, pastes, creams, lotions, gels, powders, solutions, sprays, inhalants or patches. The active product, or preparation thereof, is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a pharmaceutically active protein to the body. Such dosage forms can be made by suspending or dispensing the pharmaceutically active product in the proper medium. Absorption enhancers can also be used to increase the flux of the pharmaceutically active protein across the skin. The rate can be controlled by either providing a rate controlling membrane or by dispersing the pharmaceutically active protein in a polymer matrix or gel.

The compositions are administered in such amounts and for such time as is necessary to achieve the desired result. As described above, in certain embodiments of the present invention a "therapeutically effective amount" of a pharmaceutical composition is that amount effective for treating, attenuating, or preventing a disease in a host. Thus, the "amount effective to treat, attenuate, or prevent disease", as used herein, refers to a nontoxic but sufficient amount of the pharmaceutical composition to treat, attenuate, or prevent disease in any host. As but one example, the "therapeutically effective amount" can be an amount to treat, attenuate, or prevent diabetes, growth hormone deficiency, etc. As another example, the "therapeutically effective amount" can be an amount sufficient to cause an immune response in a subject, e.g., the production of antibodies that bind to a particular antigen. Preferably the antibodies protect against or reduce the severity of infection or protect against a disease or condition that may result from exposure to the antigen.

The exact amount required will vary from subject to subject, depending on the species, age, and general condition of the subject, the stage of the disease, the particular pharmaceutical mixture, its mode of administration, and the like. The infected plants of the invention and/or protein preparations thereof are preferably formulated in dosage unit form for ease of administration and uniformity of dosage. The expression "dosage unit form," as used herein, refers to a physically discrete unit of pharmaceutically active polynucleotide or polypeptide expression product appropriate for the patient to be treated. It will be understood, however, that the total daily usage of the compositions of the present invention is preferably decided by an attending physician within the scope of sound medical judgment. The specific therapeutically effective dose level for any particular patient or organism may depend upon a variety of factors including the disorder being treated and the severity of the disorder; the activity of the specific compound employed; the specific composition employed; the age, body weight, general health, sex of the patient, diet of the patient, pharmacokinetic condition of the patient, the time of administration, route of administration, and rate of excretion of the specific compound employed; the duration of the treatment; drugs used in combination or coincidental with the specific compound employed; and like factors well known in the medical arts.

It will also be appreciated that the pharmaceutical compositions of the present invention can be employed in combination therapies, that is, the pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anti-cancer agent), or they may achieve different effects.

EXAMPLES

Example 1

Construction of Recombinant Plant Virus Vectors

We employed vectors based on the Tobacco Mosaic Virus that are adapted for insertion of a polynucleotide of interest to create a vector for use in generating clonal root lines, clonal root cell lines, clonal plant cell lines, and/or clonal plants that express a polynucleotide of interest according to the present invention. FIG. 1 shows a schematic diagram of a TMV-based vector, D4, that was engineered to accept insertion of a polynucleotide of interest (Shivprasad et al., *Virology*, 255(2): 312-23, 1999), and illustrates insertion of various polynucleotides of interest into the vector. D4 contains a deletion of the TMV coat protein (CP) coding sequences but retains the TMV CP subgenomic promoter and the TMV 3' untranslated region (UTR), as indicated on the figure. The 126 and 183 kD proteins are required for TMV replication. The 30 kD protein is movement protein (MP), used for cell-to-cell movement. D4 contains Pac I and Xho I sites downstream of the CP subgenomic promoter, providing a site for convenient insertion of a polynucleotide of interest. Particular vectors created by inserting various polynucleotides of interest into D4 are described below.

D4C3GFP is a TMV-based expression vector that is deficient in CP production (Shivprasad et al., 1999: TTT-GFP) as a result of deletion of the TMV CP coding region and its replacement with the C3GFP gene, which is placed under the control of the TMV CP subgenomic promoter. The C3GFP gene was recloned into D4 by overlapping PCR to eliminate the Nco1 and Xho1 sites in the C3GFP nucleotide sequence to facilitate further cloning steps. A polylinker PstI-NotI-XhoI was introduced at the 3'end of C3GFP gene. The PCR product digested with PacI-XhoI was cloned into D4 resulting in D4C3GFP.

The primers we used to modify the C3GFP gene and eliminate Nco1 and Xho1 sites are:

```
1) C3GFP.Pac1.For(N)
GGGAG.ATCTT.AATTA.ATGGC.TAGCA.AAGGA.GAAGA.A    36 nt

2) C3GFP.Xho1.Rev(N)
CCCCT.CGAGC.GGCCG.CTGCA.GTTAT.TTGTA.GAGCT.     45 nt
CATCC.ATGCC

3) C3GFP.Nco1.For
GTTCC.CTGGC.CAACA.CTTGT.CAC                    23 nt

4) C3GFP.Nco1.Rev
TAGTG.ACAAG.TGTTG.GCCAG.GG                     22 nt

5) C3GFP.Xho1.For
GGACA.CAAAC.TGGAG.TACAA.CTATA                  25 nt

6) C3GFP.Xho1.Rev
AGTTA.TAGTT.GTACT.CCAGT.TTGTG                  25 nt 7) (BglII)-PacI
> AUG...HindIII...NcoI...NdeI...BsrGI...MluI...
XhoI...BamHI...MfeI(MunI)...SalI...SacI...TAA <
PstI...NotI...XhoI
```

Three constructs that contained full-length or portions of the 3'-untranslated region (3' UTR) of AlMV RNA3 were also generated. In each of these constructs, sequences encoding C3GFP under control of the subgenomic TMV CP promoter were present upstream of AlMV RNA3 3'-UTR sequences (either full-length or a portion of the UTR), to allow us to precisely identify the sequences of the AlMV RNA3 3' UTR required for assembly and movement of TMV genomic RNA (either in trans or in cis). The RNA3 sequences were inserted between the Not1 and XhoI sites of the new D4C3GFP vector as Not1-Sal1 fragments, resulting in the constructs SR25 (nts 1859-1941 of RNA3), SR26 (nts. 1859-1969 of RNA3) and SR27 (nts. 1859-2037 of RNA3, i.e., the entire 3' UTR). In addition to sequences from the AlMV RNA3 3' UTR, SR25, SR26, and SR27 also include sequences from the TMV 3' UTR (i.e., the UTR from the TMV genomic transcript) downstream of the inserted AlMV sequences. These sequences are TMV nucleotides 6192-6395, as in the D4 construct. The TMV-based viruses (SR25, SR26, and SR27) are defective in long-distance movement because the TMV coat protein is essential for effective phloem-mediated long distance transport and systemic infection of TMV.

The primers used to generate D4-based constructs with AlMV RNA3 3'-UTR sequences were:
1) SR-52 5' primer with Xho1-Pst1 sites at nt 1859 (plus sense) 5'-CCGCTCGAGCTGCAGTGTACCCCAT-TAATTTGG-3'
2) SR-53 3' primer at nt 1941 of AlMV RNA3 with Not1-Sal1 sites: minus sense 5'-CGGGTCGACGCGGCCGCGAAT-AGGACTTCATACCT-3'

3) SR-54 3' primer with Not1-Sal1 sites at nt 1969 of AlMV RNA3: minus sense 5'-CGGGTCGACGCGGCCGCAATAT-GAAGTCGATCCTA-3'
4) SR-55 3' primer with Not1-Sal1 sites at nt 2037 (minus sense) 5'-CGGGTCGACGCGGCCGCGCATCCCT-TAGGGGCATT-3'.

Viral vectors in which polynucleotides of interest (e.g., GFP, hGH, GCSF) are inserted into SR25, SR26, and/or SR27 are in the process of being tested for generation of clonal root lines, clonal plant cell lines, and clonal plants as described herein.

To generate TMV-based constructs suitable for expression of human growth hormone (hGH) we inserted the gene for hGH into the D4 vector between the Pac1 and Xho1 sites. An AUG was introduced in the 5' primer used to amplify the gene from a plasmid, and the amino acids KDEL were introduced at the 3' end of the coding sequence in order to enhance translation due to retention in the ER. For the experiments described herein, hGH was cloned without its native leader sequence, resulting in D4-hGH, which was used in the experiments described herein.

Primer SR22 (5'-CCG TTAATTAATG TTC CCA ACT ATT CCA) was used to clone hGH without its leader, and introducing a Pac1 site at the 5' end; primer SR23 (5'-CCG TTAATTAATG GCA ACT GGA TCA AGG) was used to clone hGH with its leader. Primer SR24 (5'-CGG CTC GAG TTA AAA ACC ACA TGA) was used to clone the hGH gene without KDEL and introducing a Xho1 site at the 3' end; primer SR25 (5'-CGG CTC GAG TTC ATC TTT AAA ACC TGA TCC) was used to clone the gene with KDEL.

To generate TMV-based constructs suitable for expression of human granulocyte colony stimulating factor (GCSF), we first synthesized the entire open reading frame (ORF) encoding GCSF, without the signal peptide. The sequence of the synthesized gene was optimized for expression in plants. The ORF was synthesized with Pac I and Xho I sites at the 5 and 3' ends respectively. The gene was excised by Pac I/Xho I digestion and ligated into the D4 vector, which was linearized using Pac I and Xho I. The resulting vector (D4-GCSF) was used for the experiments described herein.

Example 2

Generation and Testing of Clonal Root Lines Expressing GFP

Materials and Methods

Synthesis of viral transcripts and viral infection. In vitro transcripts of vector D4C3GFP, described above, which contains an open reading frame encoding GFP under control of the TMV CP subgenomic promoter, were synthesized using T7 polymerase. Approximately 10 μg of DNA was linearized with 30 units of KpnI overnight in a reaction volume of 100 μl. Four μl of the restriction digest was used to produce in vitro transcripts using the AmpliCap T7 High Yield message Maker Kit (Epicentre) according the manufacturers recommendations. Transcripts from one such reaction were used to infect six-week-old *Nicotiana benthamiana* plants by manually applying the transcripts dissolved in FES onto young, fully expanded leaves.

*Agrobacterium rhizogenes* stimulated root generation. *Agrobacterium rhizogenes* strain A4RSII was grown to $OD_{600}$ 0.8-1. Bacterial cells were pelleted and resuspended in MS-2 medium (MS salts, 2% sucrose, 10 mM MES, pH 5.5) to a final $OD_{600}$ of 0.5. Acetosyringone was added to a final concentration 200 μM 1 hour before transformation. Local or systemically infected leaves of *Nicotiana benthamiana* were harvested 5-14 days after inoculation with transcript. Leaves were surface sterilized for 6 min with 10% Clorox and washed several times with sterile distilled water.

Surface sterilized leaves of *N. benthamiana* were cut into pieces ~1 cm². They were dipped into bacterial suspension for 5 min, drained on filter paper and placed on the surface of solidified MS-2 medium. Plates were kept under dim light conditions at 24° C. for 48 hours. After 48 hours the excess Agrobacterial suspension was removed, and leaf explants were placed on solid hormone free $K_3$ (Kao K. N. and Michayluk M. R., *Plants*, 115:355-367, 1974.) modified according to Nagy and Maliga, (Nagy J. J. and Maliga P., *Z. Pflanzenphysiol.* 78:453-455, 1976) and Menczel et al. (Menczel L., Nagy F., Kiss L. R. and Maliga P., *Theor. Appl. Genet.* 59:191-195, 1981) medium. Plates were maintained at 25° C. with a 16 hr day/8 hr night light regime.

Three weeks after transformation, hairy roots were cut off and placed in a line on solid hormone free $K_3$ medium. Four to six days later, the most actively grown roots were isolated and transferred to liquid $K_3$ medium in individual Petri dishes. The roots were cultured on a rotary shaker at 24° C. and subcultured ~weekly by dissecting and harvesting a portion of the root mass and transferring the harvested roots to a Petri dish containing fresh $K_3$ medium. Roots were screened for the presence of the protein of interest by Western blot analysis and/or by fluorescence under UV light, depending on the particular polynucleotide of interest.

Western blot assays: For Western blot assays 10 mg of fresh root material was placed into an Eppendorf tube and homogenized in 50 ul of phosphate buffer, followed by the addition of 20 ul of 5× loading buffer and 10 minutes of boiling. After boiling, the homogenate was centrifuged for 5 to 10 minutes to clear the debris. Following centrifugation, 10 ul of sample was loaded on an SDS polyacrylamide gel, and proteins were separated by electrophoresis. Commercially available GFP protein (5 ng) (BD Biosciences Clontech) was loaded as a positive control. Leaf samples (10 mg) from *N. benthamiana* plants systemically infected with the same vector (D4C3GFP) were harvested at the time of peak expression, and an extract was prepared in an identical manner as described above for the root material and loaded on the gel for comparison with the root cell lines. Upon completion of electrophoresis proteins were electroblotted onto a nylon membrane, blocked using casein and reacted with GFP-specific antibodies (BD Biosciences Clontech). Proteins reacting with antibodies were visualized using a chemiluminescent substrate.

Results

FIGS. 6A-6E show the overall method used for generating the clonal root lines (see Description). FIG. 6G shows a photograph of a GFP-expressing clonal root line that was obtained by infecting *N. benthamiana* with viral vector D4C3GFP, harvesting leaf tissue from the infected region, infecting with *A. rhizogenes*, and culturing the pieces to allow development of hairy roots, which were then isolated and further cultured.

Figure 7:
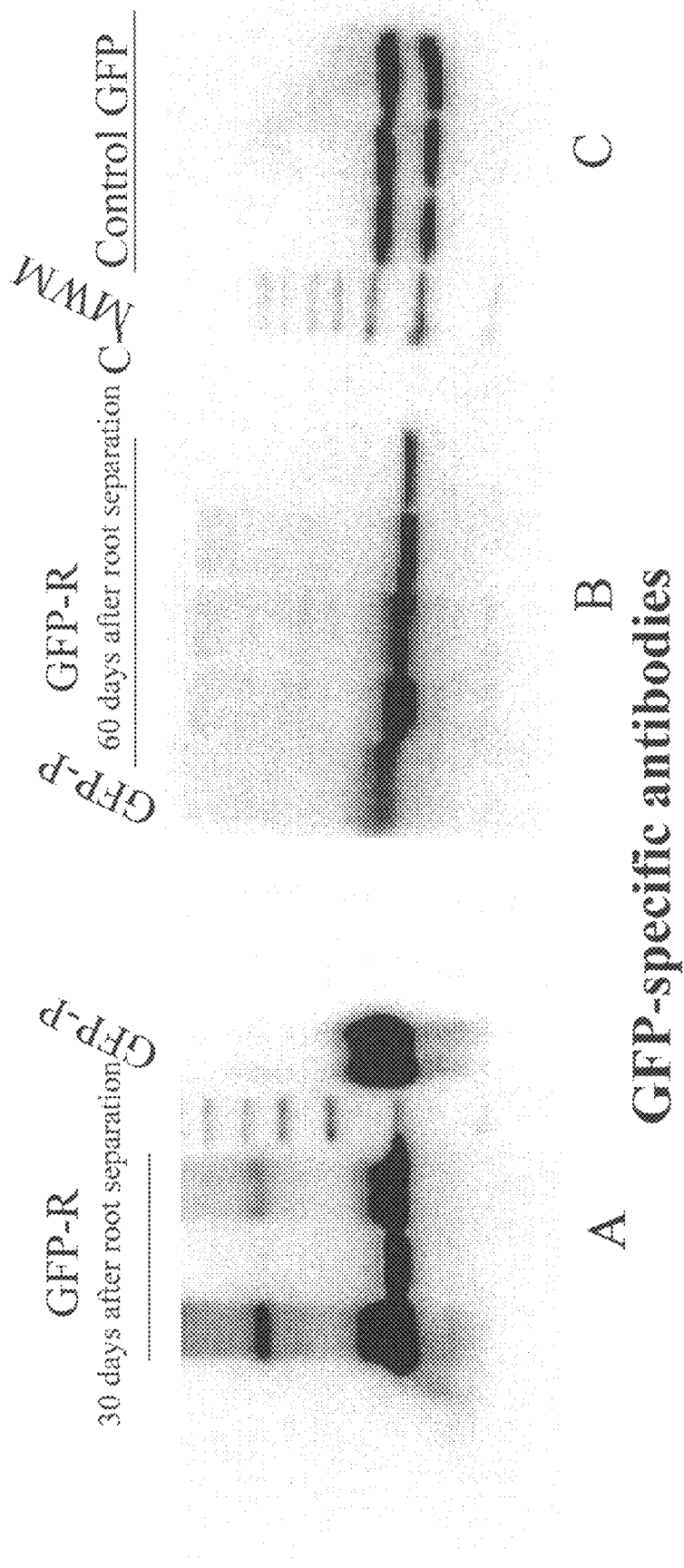
FIGS. 7A-7C show Western blot analyses demonstrating GFP production in 3 clonal root lines derived from plant cells into which a viral vector whose genome contains a gene that encodes GFP under control of the TMV CP promoter was introduced.

FIGS. 7A-7C show Western blot analyses demonstrating GFP production in 3 clonal root lines derived from plant cells into which a viral vector whose genome contains a gene that encodes GFP under control of the TMV CP promoter (D4C3GFP) was introduced. FIG. 7A shows GFP expression in the clonal root lines after 30 days of propagation in culture (i.e., 30 days after separation of the root from the leaf from which it was derived). FIG. 7B shows GFP expression in the clonal root lines after 60 days of propagation in culture (i.e., 60 days after separation of the root from the leaf from which it was derived). C- represents control lanes containing no protein. MWM represents molecular weight markers. GFP-R represents samples from clonal root lines. GFP-P represents GFP isolated from leaf tissue of a plant infected with the same construct used for generation of the clonal root lines. FIG. 7C is a control showing that the anti-GFP antibodies recognize commercially available GFP protein. These results demonstrate that the clonal root lines maintain high level expression of a protein of interest (GFP) over an extended period of time, indicating the stability of the viral transcript in the clonal root lines.

Figure 8:
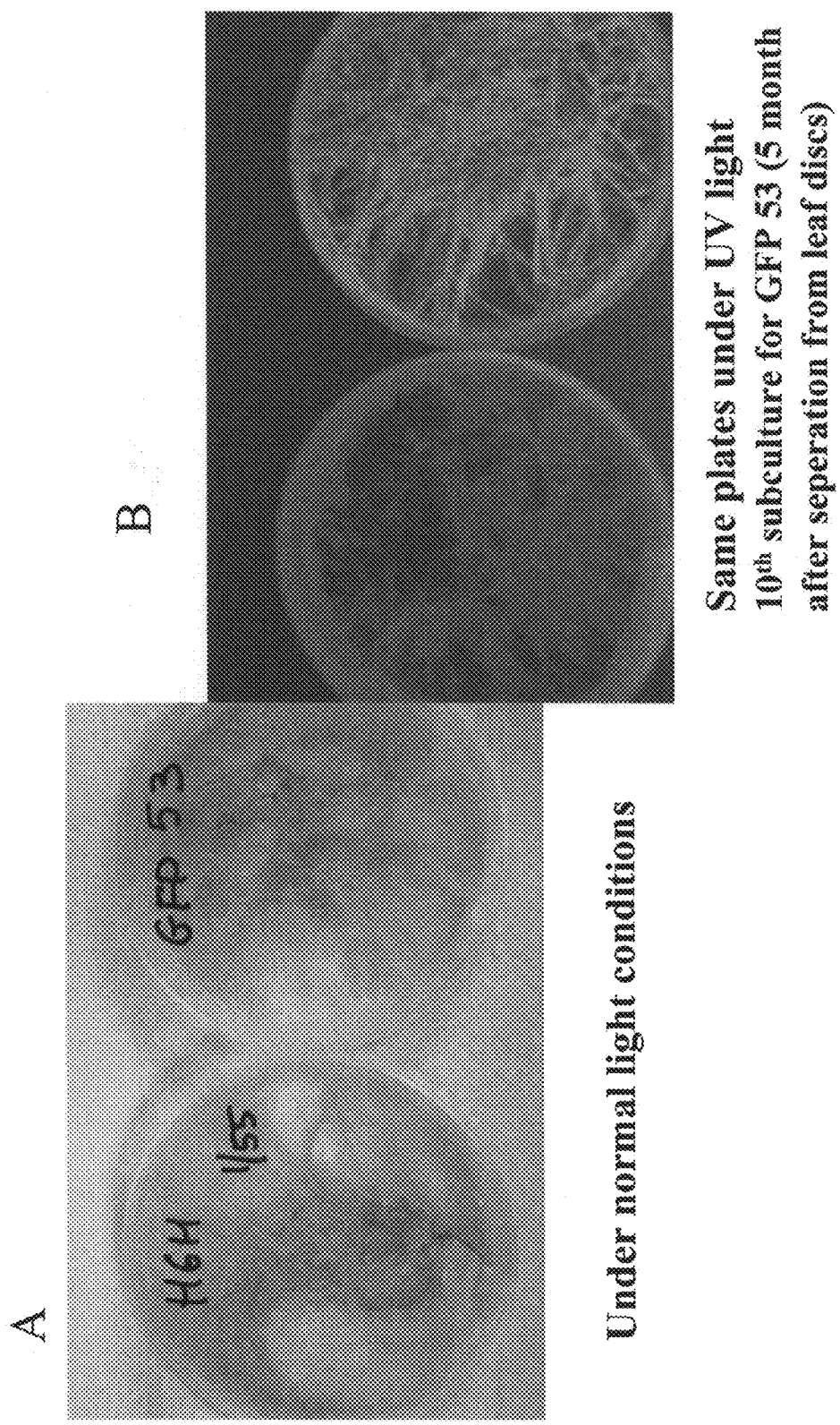
FIGS. 8A and 8B show photographs of clonal root lines producing hGH and GFP.

FIGS. 8A and 8B show photographs of clonal root lines producing hGH (see Example 4) or GFP. FIG. 8A shows a photograph of two clonal root lines taken under normal light conditions. The plate on the left shows a clonal root line derived from a plant cell into which a viral vector whose genome contains a gene that encodes human growth hormone (hGH) under control of the TMV CP promoter was introduced. The plate on the right shows a clonal root line derived from a plant cell into which a viral vector whose genome contains a gene that encodes green fluorescent protein (GFP) under control of the TMV CP promoter was introduced. FIG. 8B shows a photograph of the same clonal root lines as shown in FIG. 8A taken under UV light, demonstrating expression of GFP. These results demonstrate robust expression of GFP in the root mass and illustrate the convenience of fluorescence-based screening for expression of a polynucleotide of interest.

It is noted that Western analysis demonstrated expression of GFP throughout all portions of the root mass. However, when screened using a visual approach, expression generally appears stronger in the more mature portions of the root mass than in the growing tips, where cell division is proceeding rapidly. This appears to be due both to the time required for new cell to synthesize sufficient GFP for visibility and to the fact that when viewed from above, one is looking through multiple layers of cells in the thicker portion of the roots. It is also noted that the most mature portions of the roots may become somewhat "woody", which can obscure visual detection of GFP.

Example 3

Generation and Testing of Clonal Root Lines Expressing hGH

Figure 9:
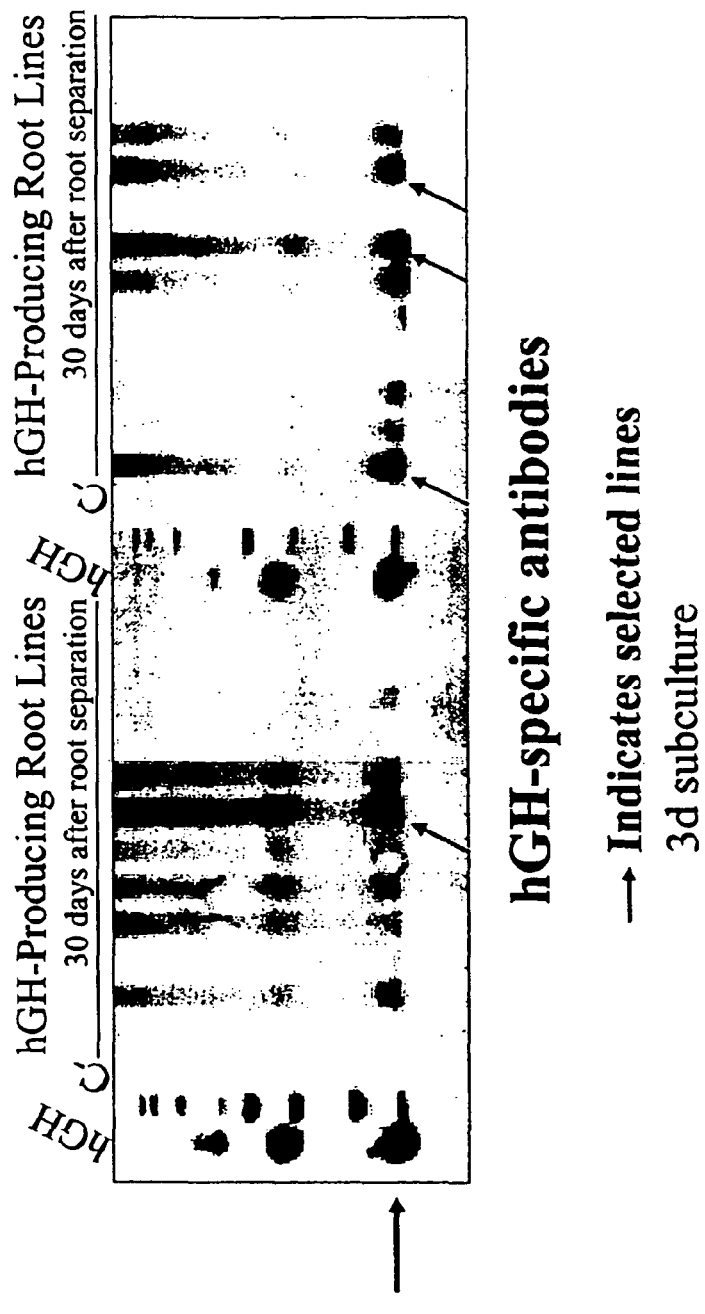
FIG. 9 shows a Western blot analysis to screen clonal root lines each derived from individual plant cells that were infected with a viral vector whose genome contains a gene that encodes human growth hormone (hGH) under control of the TMV CP promoter. Root lines were screened 30 days after separation of the root from the leaf from which it was derived. Root lines demonstrating high levels of expression are indicated with arrows. C− represents control lanes containing no protein. MWM represents molecular weight markers. hGH represents recombinant human growth hormone.
Figure 10:
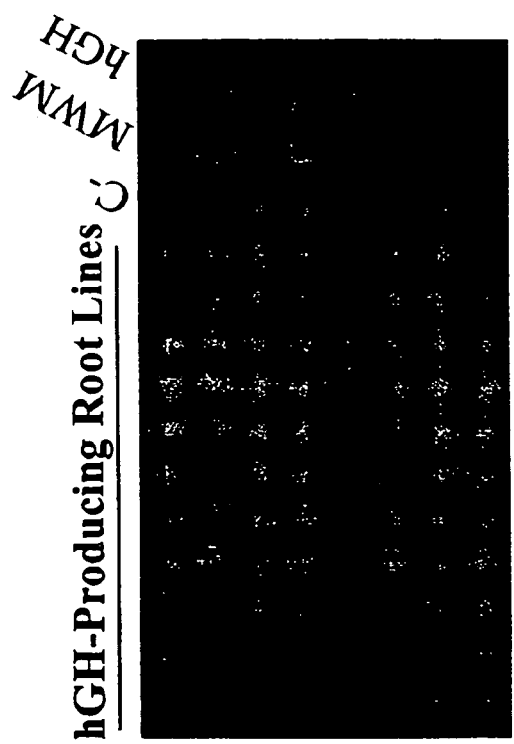
FIG. 10 shows a Western blot analysis demonstrating hGH production in selected clonal root lines derived from plant cells into which a viral vector whose genome contains a gene that encodes hGH under control of the TMV CP promoter was introduced. The analysis was performed following 10 subculturings after separation of the roots from the leaves from which they were derived. C- represents a control lane containing no protein. MWM represents molecular weight markers. hGH represents recombinant human growth hormone.

N. benthamiana plants were inoculated with a TMV-based vector, D4-hGH, containing an open reading frame encoding hGH under control of the TMV CP subgenomic promoter. Hairy roots were obtained and subcultured essentially as described in Example 2. Two weeks after separation from leaf discs, during the third round of subculture, the segments of roots were analyzed for hGH expression by Western blot assay (FIG. 9) essentially as described in Example 2. Five ng hGH protein (Research Diagnostics) was used as a control in all Western blots in which expression of hGH was tested. Anti-hGH antibodies were from Research Diagnostics. As can be seen from FIG. 9, up to 80% of the clonal root lines had detectable levels of hGH. We selected the highest producers and propagated them further. After 10 passages (subculturings), samples were taken and analyzed for hGH accumulation. FIG. 10 shows a Western blot, demonstrating that the clonal root lines maintained stable expression of hGH after 10 passages in which hGH expression in selected lines was several fold higher (250 ug/gram fresh root tissue) than that in leaves infected with the same virus construct (70 ug/gram fresh leaf tissue) when compared by Western blot.

FIGS. 8A and 8B show photographs of clonal root lines producing hGH and GFP. FIG. 8A shows a photograph of two clonal root lines taken under normal light conditions. The plate on the left shows a clonal root line derived from a plant cell into which a viral vector whose genome contains a gene that encodes human growth hormone (hGH) under control of the TMV CP promoter was introduced. The plate on the right shows a clonal root line derived from a plant cell into which a viral vector whose genome contains a gene that encodes green fluorescent protein (GFP) under control of the TMV CP promoter was introduced. FIG. 8B shows a photograph of the same clonal root lines as shown in FIG. 8A taken under UV light, demonstrating expression of GFP.

Example 4

Generation and Testing of Clonal Root Lines Expressing GCSF

Figure 11:
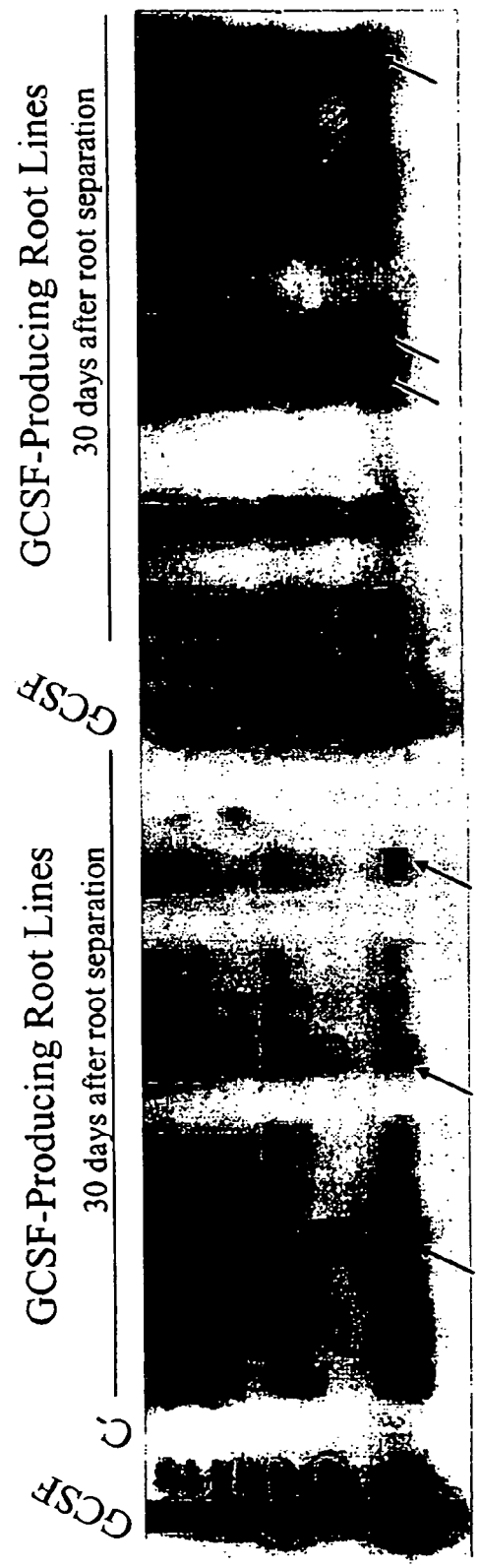
FIG. 11 shows Western blot analysis to screen clonal root lines each derived from individual plant cells that were infected with a viral vector whose genome contains a gene that encodes human growth hormone (GCSF) under control of the TMV CP promoter. Root lines were screened 30 days after separation of the root from the leaf from which it was derived. Root lines demonstrating high levels of expression are indicated with arrows. C- represents control lanes containing no protein. MWM represents molecular weight markers. GCSF represents recombinant human granulocyte colony stimulating factor.
Figure 12:
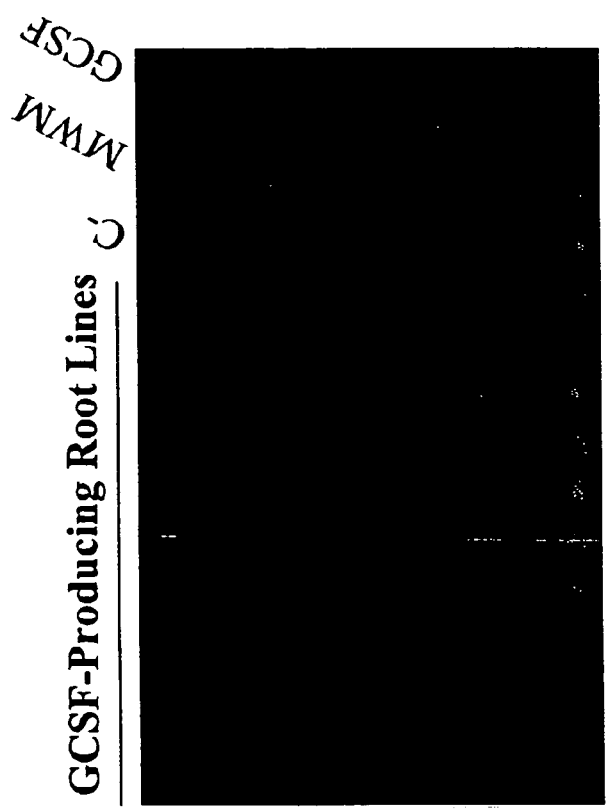
FIG. 12 shows a Western blot analysis demonstrating GCSF production in selected clonal root lines derived from plant cells into which a viral vector whose genome contains a gene that encodes GCSF under control of the TMV CP promoter was introduced. The analysis was performed following 10 subculturings after separation of the roots from the leaves from which they were derived. C- represents a control lane containing no protein. MWM represents molecular weight markers. GCSF represents recombinant human granulocyte colony stimulating factor.

N. benthamiana plants were inoculated with a TMV-based vector, D4-GCSF, containing an open reading frame encoding GCSF under control of the TMV CP subgenomic promoter, and hairy roots were obtained essentially as described in Example 2. Two weeks after separation from leaf discs the segments of roots were analyzed for GCSF expression by Western blot assay (FIG. 11). As can be seen from FIG. 11, up to 80% of the clonal root lines had detectable levels of GCSF. We selected the highest producers and propagated them further. After 10 passages (in which portions of the root mass were harvested and transferred to new Petri dishes containing fresh medium) samples were taken and analyzed for GCSF accumulation. FIG. 12 shows a Western blot, demonstrating that the clonal root lines maintained stable expression of GCSF after 10 passages (subculturings). Five ng recombinant GCSF produced using an E. coli expression system was used as a control in all Westerns in which expression of GCSF was tested. Anti-GCSF antibodies were from Oncogene Science.

Example 5

Generation and Testing of Clonal Plant Cell Lines Expressing GCSF

Cell culture and electroporation. Cell lines derived from Nicotiana tabacum cv Bright yellow (BY-2) were maintained in MS medium (Murashige T. and Skoog F., Physiol. Plant. 15:473-497, 1962) supplemented with 0.2 mg/l 2,4-D and 0.1 mg/l Kinetin, 20 mM MES, pH 5.6-5.8 on a shaker, 140 rpm at 25° C., and subcultured weekly. For electroporation, protoplasts were generated from cells that had been subcultured for 3-4 days. Cells were spun at 1000 rpm for 8 min, washed 2× with Mannitol 0.4M and MES 20 mM, pH 5.5. Cells were then taken to 30-50 ml with filter sterilized protoplasting solution: 0.4M mannitol, MES 20 mM, pH5.5, Cellulase Onozuka RS (Yakult Honsha Co.) 1%, Pectolyase Y23 (Seishin Pharmaceutical Co.) 0.1%. Cells were incubated in 250 ml flasks at 25° C. for 20-25 min. The protoplast solution was filtered through a 100/μm sieve, spun at 700 rpm for 6 min, and washed 2× with ice-cold 0.4M Mannitol. Protoplasts were counted using a hemacytometer and resuspended in electroporation buffer: 10 mM HEPES, 150 mM NaCl. 5 mM $CaCl_2$, 0.4M mannitol, pH 7.2 to a final concentration $1 \times 10^6$ protoplasts/ml.

Transcript (25-30 μl) was placed into an electroporation cuvette, 0.4 cm (Biorad) kept on ice, and after 10-15 min was mixed with 0.5 ml of protoplast suspension by Pasteur pipette and immediately used to electroporate cells. Electroporation was performed using a Biorad Gene Pulser at 250 volts and 175 capacitance. Electroporated protoplasts were resuspended in 8 ml of PBS buffer containing 0.4 M mannitol and maintained for formation of the cell wall.

Enrichment for stable producer cell lines. Within 4-5 days following electroporation, dividing cells were diluted and sampled (10 ul of infected cells into 100 ul of medium) to enrich for cells that expressed the polynucleotide of interest (target molecule) at high levels. The diluted cells were spotted onto individual sections of a Petri dish, as shown in FIG. 13E. Two to three weeks later each sample was tested by visual or other means (e.g., Western blot) for the presence of target molecule (e.g., GFP, GCSF, hGH, etc.). Stably infected cells producing target molecule were selected for further enrichment until producer cell line is obtained.

Results

Figure 14:
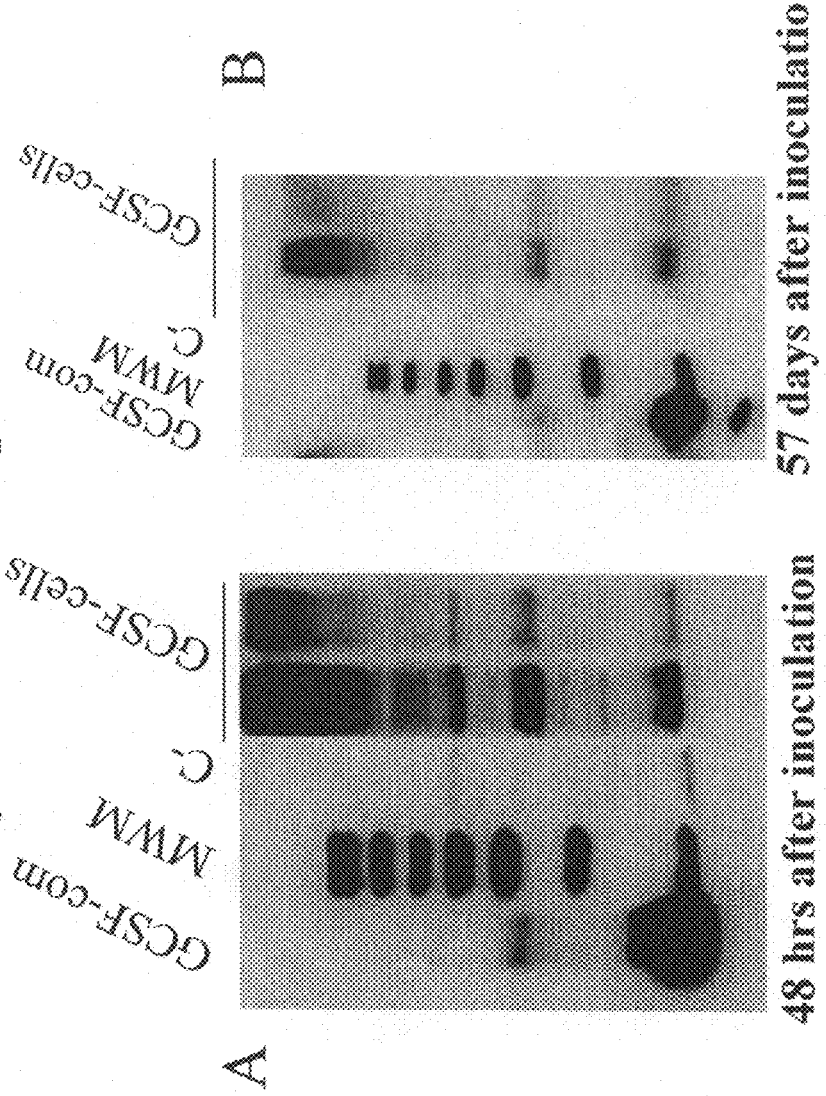
FIG. 14 shows Western blot analyses demonstrating GCSF production in a clonal plant cell line derived from a plant cell into which a viral vector whose genome contains a gene that encodes GCSF under control of the TMV CP promoter was introduced.

Clonal plant cell lines were derived by introducing a TMV-based viral vector containing an open reading frame that encodes GCSF under control of the TMV CP subgenomic promoter into BY-2 cells. The overall process is shown in FIG. 13. Enrichment for cells that express GCSF was performed using Western blot assays until populations of cells (either single clonal cell lines or populations containing several clonal cell lines) were obtained. FIG. 14 shows Western blot analyses demonstrating GCSF production in a plant cell population derived from plant cells into which a viral vector whose genome contains a gene that encodes GCSF under control of the TMV CP promoter was introduced. It is noted that the enriched plant cell population may contain either a single clonal cell line or multiple lines. Further enrichment, using more dilute samples, would result in clonal cell lines. FIG. 14A shows a Western blot performed 48 hours after introduction of the vector. FIG. 14B shows a Western blot performed using the same cell populations as shown in FIG. 14A performed after further maintaining the cells in culture, i.e., 57 days after inoculation. GCSF-COM indicates a lane in which recombinant GCSF protein was loaded as a positive control. MWM indicates molecular weight markers. C– indicates a lane in which plant extract made from plants not expressing GCSF was loaded.

Example 6

Generation and Testing of Clonal Cell Lines Expressing GFP

Results

Clonal plant cell lines were derived by introducing a TMV-based viral vector containing an open reading frame that encodes GFP under control of the TMV CP subgenomic promoter (D4C3GFP) into BY-2 cells essentially as described in Example 5. Enrichment for cells that express GFP was performed using a visual screen for fluorescence until populations of cells (either single clonal cell lines or populations containing several clonal cell lines) that stably express GFP were obtained. FIG. 13C shows a protoplast suspension containing cells into which the viral vector was introduced. FIG. 13E shows diluted samples from the suspension plated in individual droplets on Petri dishes. FIG. 13F shows the same Petri dishes as in FIG. 13E under UV light. Clonal plant cell lines expressing GFP are readily seen. It is noted that the droplets may contain either a single clonal plant cell line or multiple clonal plant cell lines. Single clonal plant cell lines (i.e, populations derived from a single ancestral cell) can be generated by further limiting dilution using standard methods for single cell cloning.

Figure 15:
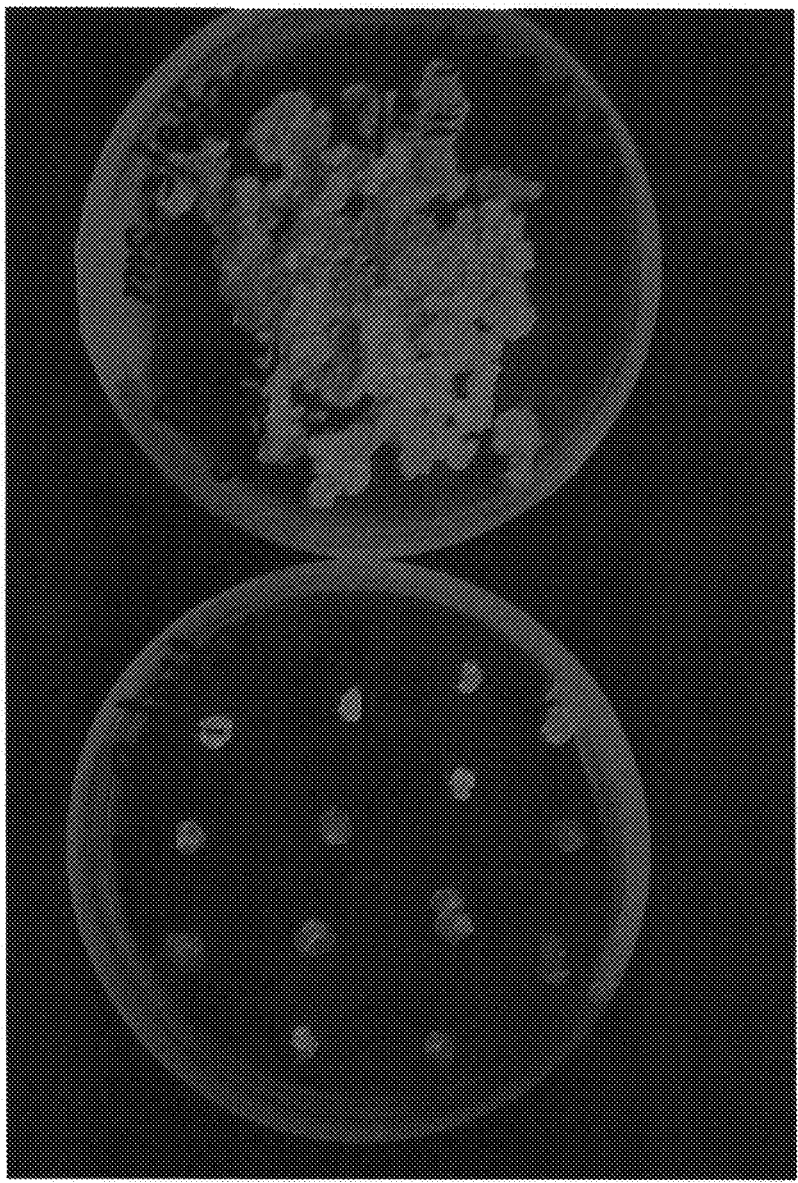
FIG. 15 shows GFP production in plant cell lines derived from plant cells into which a viral vector whose genome contains a gene that encodes GFP under control of the TMV CP promoter was introduced.

FIG. 15 shows GFP production in plant cell lines derived from plant cells into which D4C3GFP. FIG. 15A shows enrichment for plant cell lines that express GFP. FIG. 15B shows a callus obtained from a clonal plant cell line that contains a similar viral vector that does not encode GFP. The photographs were taken 3 months after the vector was introduced into the cells from which the clones in FIG. 15A were derived. Both photographs were taken under UV light.

Example 7

Generation and Testing of a Clonal Plant

Figure 16:
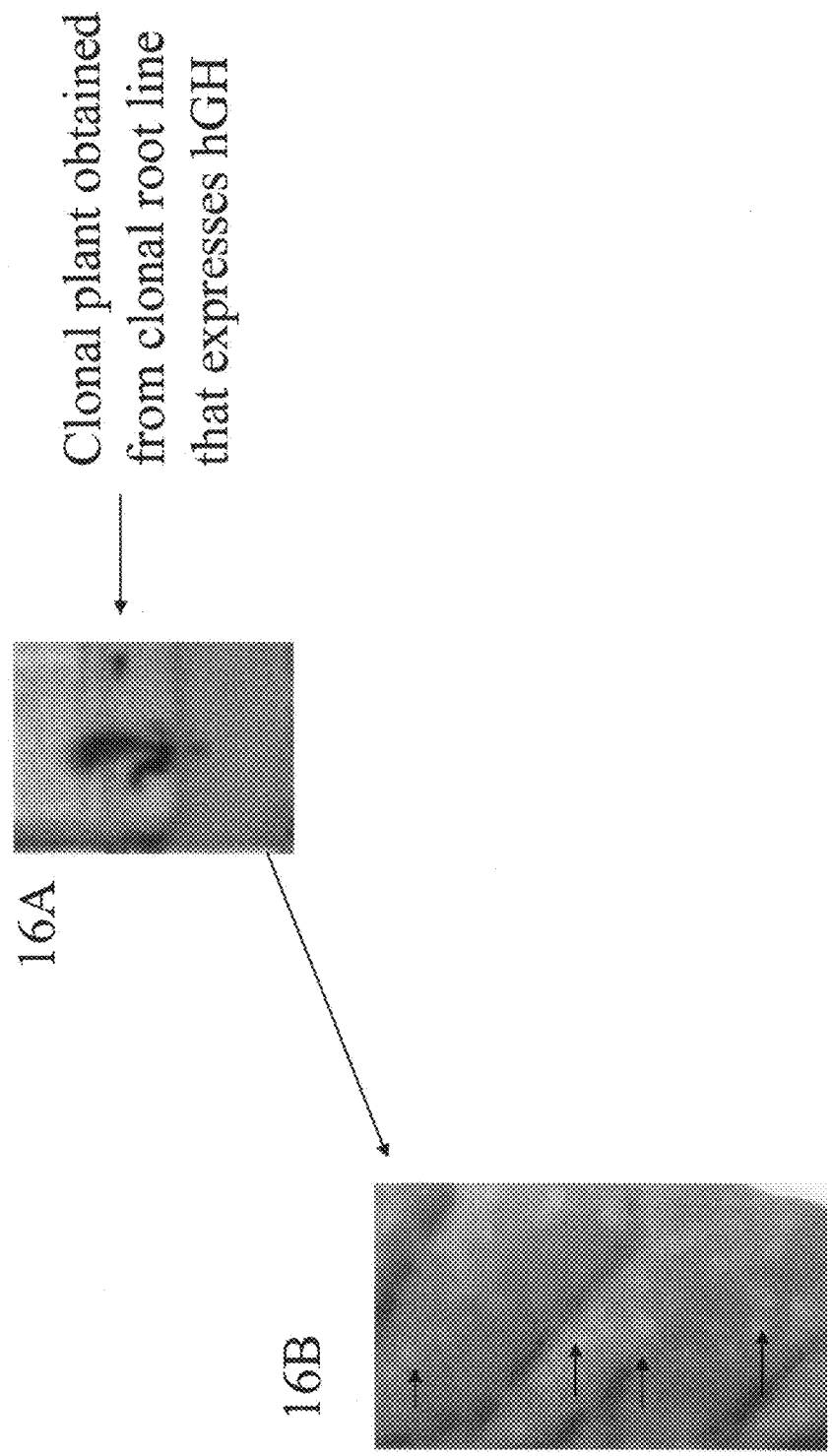
FIG. 16A shows a clonal plant that was obtained from a clonal root line derived from a plant cell into which a viral vector encoding hGH was introduced.
FIG. 16B shows lesion formation in a sensitive host plant that was inoculated with a small leaf sample from the clonal plant, indicating that the clonal plant regenerated from the clonal root line maintains active viral replication. To test if the plant maintains virus replication a small leaf sample was used to inoculate a tobacco variety that is a host for formation of local lesions. Formation of lesions within 2 days of inoculation (see arrows) indicates that the clonal plant line regenerated from a clonal root line maintains active virus replication.

Clonal root lines expressing hGH were obtained as described in Example 3. Root cells were isolated by enzymatic digestion and cultured as described in Peres et al., *Plant Cell, Tissue, and Organ Culture* 65, 37-44, 2001, to generate clonal plants. FIG. 16A shows a plant that was obtained from a clonal root line. To determine whether the plant contained the viral vector, a small leaf sample was used to inoculate a tobacco variety that is a sensitive host for formation of local lesions upon viral infection. Formation of lesions within 2 days of inoculation, as indicated by arrows in FIG. 16B, indicated that the clonal plant regenerated from the clonal root line maintains active viral replication, strongly suggesting that the clonal plant also expresses hGH. Additional experiments showed that this was indeed the case (data not shown).

Equivalents

Those skilled in the art will recognize, or be able to ascertain using no more than routine experimentation, many equivalents to the specific embodiments of the invention described herein. The scope of the present invention is not intended to be limited to the above Description, but rather is as set forth in the following claims.

We claim:

1. A clonal entity derived from a plant or portion thereof, wherein the cells of the clonal entity originate from a cell comprising (i) a self-replicating, episomal viral RNA vector maintained extrachromosomally, which RNA vector comprises a polynucleotide of interest that is not naturally associated with the viral vector sequences; and (ii) an Ri T-DNA or portion thereof sufficient to generate hairy roots, wherein the cell was infected with the viral RNA vector prior to introduction of the Ri T-DNA or portion thereof, wherein the cells of the clonal entity stably comprise the self-replicating, episomal viral RNA vector and the Ri T-DNA or portion thereof.

2. The clonal entity of claim 1, wherein the clonal entity is a clonal root line.

3. The clonal root line of claim 2, wherein the viral RNA is derived from Tobacco Mosaic Virus (TMV) or Alfalfa Mosaic Virus (AlMV).

4. The clonal root line of claim 2, wherein the polynucleotide of interest is operably linked to a coat protein (CP) promoter, a movement protein (MP) promoter, an inducible promoter, or a transactivator promoter.

5. The clonal entity in claim 1, wherein the clonal entity is a clonal root cell line.

6. The clonal root cell line of claim 5, wherein the viral RNA is derived from TMV or AlMV.

7. The clonal root cell line of claim 5, wherein the polynucleotide of interest is operably linked to a CP promoter, an MP promoter, an inducible promoter, or a transactivator promoter.

8. The clonal entity in claim 1, wherein the clonal entity is a clonal plant cell line.

9. The clonal plant cell line of claim 8, wherein the viral RNA is derived from TMV or AlMV.

10. The clonal plant cell line of claim 8, wherein the polynucleotide of interest is operably linked to a CP promoter, an MP promoter, an inducible promoter, or a transactivator promoter.

11. The clonal entity in claim 1, wherein the clonal entity is a clonal plant.

12. The clonal plant cell line of claim 11, wherein the viral RNA is derived from TMV or AlMV.

13. The clonal plant cell line of claim 11, wherein the polynucleotide of interest is operably linked to a CP promoter, an MP promoter, an inducible promoter, or a transactivator promoter.

14. A method of obtaining a clonal entity that stably contains an expressible polynucleotide of interest, comprising the steps of:
   (i) introducing into a plant or portion thereof a self-replicating, extrachromosomal episomal viral RNA vector that comprises the polynucleotide of interest, wherein the polynucleotide of interest is not naturally associated with the viral vector sequences; and
   (ii) subsequently introducing an Ri T-DNA or portion thereof sufficient to generate hairy roots into the plant or portion thereof, to generate a clonal entity from the plant;
   wherein the cells of the clonal entity originate from a cell comprising the self-replicating, episomal viral RNA vector; and wherein the cells of the clonal entity stably comprise the self-replicating, episomal viral RNA vector and the Ri T-DNA or portion thereof.

15. A method of producing a polynucleotide or polypeptide, comprising the steps of;
   (i) generating a clonal entity derived from a plant, wherein the cells of the clonal entity originate from a cell comprising a self-replicating, episomal viral RNA vector maintained extrachromosomally, which RNA vector comprises a polynucleotide of interest that is not naturally associated with the viral vector sequences; wherein said generating comprises introducing into said cell comprising a self-replicating, episomal viral RNA vector an Ri T-DNA or portion thereof sufficient to generate hairy roots;
   wherein the clonal entity contains the self-replicating, episomal viral RNA vector and the Ri T-DNA or portion thereof, and wherein the clonal entity stably contains and/or expresses the polynucleotide of interest;
   (ii) maintaining the clonal entity in culture if the clonal entity is a clonal root line, clonal root cell line, or clonal plant cell line; or growing the clonal entity if the clonal entity is a clonal plant;
   (iii) harvesting cells or culture medium if the clonal entity is a clonal root line, clonal root cell line, or clonal plant cell line; or harvesting plant tissue if the clonal entity is a clonal plant; and
   (iv) isolating or purifying from the harvested cells, culture medium or plant tissue the polynucleotide of interest or a polypeptide encoded thereby.

16. A method comprising:
   (i) obtaining a clonal entity from a plant, which clonal entity originates from a cell comprising (a) a self-replicating, episomal viral RNA vector maintained extrachromosomally, which RNA vector comprises a polynucleotide of interest that is not naturally associated with the viral vector sequences, and (b) an Ri T-DNA or portion thereof sufficient to generate hairy roots; wherein the cell was infected with the viral RNA vector prior to introduction of the Ri T-DNA or portion thereof; and
   (ii) maintaining the clonal entity wherein the cells of the clonal entity stably comprise the self-replicating, episomal viral RNA vector and the Ri T-DNA or portion thereof; so that the polynucleotide of interest is stably expressed.

17. The method of claim 16 wherein the polynucleotide of interest encodes, or is the complement of a polynucleotide that encodes, a polypeptide of interest.

18. The clonal entity of claim 1, wherein the viral RNA is derived from TMV or AlMV.

19. The clonal entity of claim 1, wherein the polynucleotide of interest is operably linked to a CP promoter, an MP promoter, an inducible promoter, or a transactivator promoter.

20. The clonal entity of claim 1, wherein the viral vector lacks sequences coding for a functional coat protein, functional movement protein, or both.

21. The clonal entity of claim 18, wherein the viral vector lacks sequences coding for a functional coat protein, functional movement protein, or both.

22. The method of claim 14, wherein the clonal entity is a clonal root line.

23. The method of claim 22, wherein the viral RNA is derived from TMV or AlMV.

24. The method of claim 22, wherein the viral vector lacks sequences coding for a functional coat protein, functional movement protein, or both.

25. The method of claim 15, wherein the clonal entity is a clonal root line.

26. The method of claim 25, wherein the viral RNA is derived from TMV or AlMV.

27. The method of claim 26, wherein the viral vector lacks sequences coding for a functional coat protein, functional movement protein, or both.

28. The method of claim 16, wherein the clonal entity is a clonal root line.

29. The method of claim 28, wherein the viral RNA is derived from TMV or AlMV.

30. The method of claim 29, wherein the viral vector lacks sequences coding for a functional coat protein, functional movement protein, or both.

31. The method of claim 14, wherein step (ii) comprises contacting the plant or portion thereof with an *Agrobacterium* that is a causative agent of hairy root disease.

32. The method of claim 15, wherein said introducing comprises contacting the plant or a portion thereof with an *Agrobacterium* that is a causative agent of hairy root disease.

\* \* \* \* \*

UNITED STATES PATENT AND TRADEMARK OFFICE
CERTIFICATE OF CORRECTION

PATENT NO. : 8,148,608 B2
APPLICATION NO. : 11/061980
DATED : April 3, 2012
INVENTOR(S) : Vidadi Yusibov It is certified that error appears in the above-identified patent and that said Letters Patent is hereby corrected as shown below:

Title page, Column 2 (other publications), line 1, please delete "Terrms" and insert --Terms--, therefor.

Column 48, line 23, please delete "of;" and insert --of:--, therefor.

Signed and Sealed this
Fifth Day of June, 2012

David J. Kappos
*Director of the United States Patent and Trademark Office*

SEQUENCE LISTING

```
<160> NUMBER OF SEQ ID NOS: 14

<210> SEQ ID NO 1
<211> LENGTH: 36
<212> TYPE: DNA
<213> ORGANISM: Artificial
<220> FEATURE:
<223> OTHER INFORMATION: Primers to modify the C3GFP gene and eliminate
      NcoI and XhoI

<400> SEQUENCE: 1
gggagatctt aattaatggc tagcaaagga gaagaa                              36
```

<210> SEQ ID NO 2
<211> LENGTH: 45
<212> TYPE: DNA
<213> ORGANISM: Artificial
<220> FEATURE:
<223> OTHER INFORMATION: Primers to modify the C3GFP gene and eliminate
      Nco1 and Xho1

<400> SEQUENCE: 2
cccctcgagc ggccgctgca gttatttgta gagctcatcc atgcc           45

<210> SEQ ID NO 3
<211> LENGTH: 23
<212> TYPE: DNA
<213> ORGANISM: Artificial
<220> FEATURE:
<223> OTHER INFORMATION: Primers to modify the C3GFP gene and eliminate
      Nco1 and Xho1

<400> SEQUENCE: 3
gttccctggc caacacttgt cac                                   23

<210> SEQ ID NO 4
<211> LENGTH: 22
<212> TYPE: DNA
<213> ORGANISM: Artificial
<220> FEATURE:
<223> OTHER INFORMATION: Primers to modify the C3GFP gene and eliminate
      Nco1 and Xho1

<400> SEQUENCE: 4
tagtgacaag tgttggccag gg                                    22

<210> SEQ ID NO 5
<211> LENGTH: 25
<212> TYPE: DNA
<213> ORGANISM: Artificial
<220> FEATURE:
<223> OTHER INFORMATION: Primers to modify the C3GFP gene and eliminate
      Nco1 and Xho1

<400> SEQUENCE: 5
ggacacaaac tggagtacaa ctata                                 25

<210> SEQ ID NO 6
<211> LENGTH: 25
<212> TYPE: DNA
<213> ORGANISM: Artificial
<220> FEATURE:
<223> OTHER INFORMATION: Primers to modify the C3GFP gene and eliminate
      Nco1 and Xho1

<400> SEQUENCE: 6
agttatagtt gtactccagt ttgtg                                 25

<210> SEQ ID NO 7
<211> LENGTH: 33
<212> TYPE: DNA
<213> ORGANISM: Artificial
<220> FEATURE:
<223> OTHER INFORMATION: primer with Xho1-Pst1 sites at nt 1859 (plus
      sense)

<400> SEQUENCE: 7
ccgctcgagc tgcagtgtac cccattaatt tgg                        33

-continued

```
<210> SEQ ID NO 8
<211> LENGTH: 35
<212> TYPE: DNA
<213> ORGANISM: Artificial
<220> FEATURE:
<223> OTHER INFORMATION: primer at nt 1941 of A1MV RNA3 with Not1-Sal1
      sites: minus sense

<400> SEQUENCE: 8
cgggtcgacg cggccgcgaa taggacttca tacct                              35

<210> SEQ ID NO 9
<211> LENGTH: 35
<212> TYPE: DNA
<213> ORGANISM: Artificial
<220> FEATURE:
<223> OTHER INFORMATION: primer with Not1-Sal1 sites at nt 1969 of A1MV
      RNA3: minus sense

<400> SEQUENCE: 9
cgggtcgacg cggccgcaat atgaagtcga tccta                              35

<210> SEQ ID NO 10
<211> LENGTH: 35
<212> TYPE: DNA
<213> ORGANISM: Artificial
<220> FEATURE:
<223> OTHER INFORMATION: primer with Not1-Sal1 sites at nt 2037 (minus
      sense)

<400> SEQUENCE: 10
cgggtcgacg cggccgcgca tcccttaggg gcatt                              35

<210> SEQ ID NO 11
<211> LENGTH: 28
<212> TYPE: DNA
<213> ORGANISM: Artificial
<220> FEATURE:
<223> OTHER INFORMATION: Was used to clone hGH without its leader, and
      introducing a Pac1 site at the 5' end.

<400> SEQUENCE: 11
ccgttaatta atgttcccaa ctattcca                                      28

<210> SEQ ID NO 12
<211> LENGTH: 28
<212> TYPE: DNA
<213> ORGANISM: Artificial
<220> FEATURE:
<223> OTHER INFORMATION: Primer SR23 was used to clone hGH with its
      leader.

<400> SEQUENCE: 12
ccgttaatta atggcaactg gatcaagg                                      28

<210> SEQ ID NO 13
<211> LENGTH: 24
<212> TYPE: DNA
<213> ORGANISM: Artificial
<220> FEATURE:
<223> OTHER INFORMATION: Primer SR24 was used to clone the hGH gene
      without KDEL and introducing a Xho1 site at the 3' end.

<400> SEQUENCE: 13
cggctcgagt taaaaccac atga                                           24

<210> SEQ ID NO 14
<211> LENGTH: 30
```

```
<212> TYPE: DNA
<213> ORGANISM: Artificial
<220> FEATURE:
<223> OTHER INFORMATION: Primer SR25 was used to clone the gene with
      KDEL.

<400> SEQUENCE: 14
cggctcgagt tcatctttaa aacctgatcc                                      30
```